United States Patent

Grammenos et al.

Patent Number: 5,254,717
Date of Patent: Oct. 19, 1993

[54] IMINO-SUBSTITUTED PHENYL DERIVATIVES, THE PREPARATION THEREOF AND FUNGICIDES CONTAINING THESE

[75] Inventors: Wassilios Grammenos; Albrecht Harreus, both of Ludwigshafen; Hubert Sauter; Beate Hellendahl, both of Mannheim; Reinhard Doetzer, Weinheim; Eberhard Ammermann, Ludwigshafen; Gisela Lorenz, Neustadt, all of Fed. Rep. of Germany

[73] Assignee: BASF Aktiengesellschaft, Ludwigshafen, Fed. Rep. of Germany

[21] Appl. No.: 825,378

[22] Filed: Jan. 24, 1992

[30] Foreign Application Priority Data

Feb. 20, 1991 [DE] Fed. Rep. of Germany ......... 405160

[51] Int. Cl.$^5$ ............. C07C 229/34; C07C 37/50
[52] U.S. Cl. ......................... 560/35; 544/224; 544/332; 546/306; 548/235; 558/391; 560/13; 560/34; 562/439; 562/440
[58] Field of Search ............... 560/35, 34, 16; 514/539, 564, 538, 533, 378, 521, 275, 247, 353; 562/440, 439; 548/235; 558/391; 544/224, 332; 546/306

[56] References Cited

U.S. PATENT DOCUMENTS

| | | | |
|---|---|---|---|
| 4,829,085 | 5/1989 | Wenderoth et al. | 560/35 |
| 4,956,387 | 9/1990 | Wenderoth et al. | 560/35 |
| 4,999,042 | 3/1991 | Anthony et al. | 560/35 |
| 5,112,862 | 5/1992 | Wenderoth et al. | 514/539 |
| 5,115,866 | 5/1992 | Wenderoth et al. | 514/539 |

FOREIGN PATENT DOCUMENTS 0370629 5/1990 European Pat. Off.
0415569 3/1991 European Pat. Off.

Primary Examiner—José G. Dees
Assistant Examiner—B. Frazier
Attorney, Agent, or Firm—Oblon, Spivak, McClelland, Maier & Neustadt

[57] ABSTRACT

Compound of the formula I

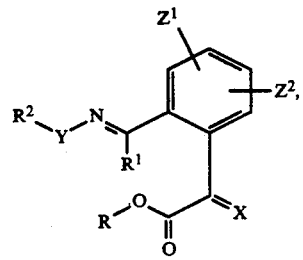

where
R is hydrogen or alkyl,
$R^1$ is hydrogen, alkyl, haloalkyl or aryl,
$Z^1$ and $Z^2$ are hydrogen, halogen, alkoxy, alkenyloxy, cyano, nitro, haloalkyl, haloalkenyloxy, alkenyl, haloalkoxy, alkyl or alkynyl,
Y is O or $NR^3$, where $R^3$ is hydrogen or alkyl,
$R^2$ is H, alkyl, cycloalkyl, alkenyl, aryl, alkynyl, cycloalkenyl, arylalkyl, aryloxyalkyl, hetaryl, hetarylalkyl, hetaryloxyalkyl, acyl, arylalkenyl, hetarylalkenyl, heterocyclyl, arylcarbonyl, hetarylcarbonyl or alkoxycarbonylalkyl,
Y and $R^2$ may form a ring, and
X is $CH_2$, CH-alkyl, CH-alkoxy, CH-alkylthio, N-alkoxy or NOH,
and fungicides containing these compounds.

7 Claims, No Drawings

IMINO-SUBSTITUTED PHENYL DERIVATIVES, THE PREPARATION THEREOF AND FUNGICIDES CONTAINING THESE

The present invention relates to novel substituted oxime ethers, hydrazones and fungicides which contain these compounds.

The use of phenylacrylic acid enol ethers as fungicides has been disclosed (EP 370 629). However, their effect is unsatisfactory.

We have now found, surprisingly, that substituted oxime ethers and hydrazones of the formula I

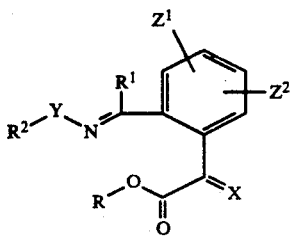

where

R is hydrogen or $C_1$–$C_6$-alkyl;

$R^1$ is hydrogen, $C_1$–$C_4$-allcyl, $C_1$–$C_4$-haloalkyl or unsubstituted or substituted aryl, $Z^1$ and $Z^2$ are identical or different and each is hydrogen, halogen, $C_1$–$C_4$-alkoxy, $C_2$–$C_4$-alkenyloxy, cyano, nitro, $C_1$–$C_4$-haloalkyl, $C_2$–$C_4$-haloalkenyloxy, $C_2$–$C_4$-alkenyl, $C_1$–$C_4$-haloalkoxy, $C_1$–$C_6$-alkyl or $C_2$–$C_4$-alkynyl, Y is oxygen (—O—), nitrogen, (—NH—) or $C_1$–$C_6$-alkyl ($R^3$)-substituted nitrogen (—N($R^3$)—);

$R^2$ is hydrogen, unsubstituted or substituted alkyl, unsubstituted or substituted cycloalkyl, unsubstituted or substituted alkenyl, unsubstituted or substituted aryl, unsubstituted or substituted alkynyl, unsubstituted or substituted cycloalkenyl, unsubstituted or substituted arylalkyl, unsubstituted or substituted aryloxyalkyl, unsubstituted or substituted hetaryl, unsubstituted or substituted hetarylalkyl, unsubstituted or substituted hetaryloxyalkyl, unsubstituted or substituted acyl, unsubstituted or substituted arylalkenyl, unsubstituted or substituted hetarylalkenyl, unsubstituted or substituted heterocyclyl, unsubstituted or substituted heterocyclyloxy, unsubstituted or substituted arylcarbonyl, unsubstituted or substituted hetarylcarbonyl or $C_1$–$C_4$-alkoxycarbonyl-$C_1$–$C_4$-alkyl, where Y and $R^2$ may form a ring which may be substituted if Y is —NH— or —$NR^3$—;

X is $CH_2$, CH—$C_1$–$C_4$-alkyl, CH—$C_1$–$C_4$-alkoxy, CH-Cl-C4-alkylthio, N—$C_1$–$C_4$-alkoxy or NOH, have a good fungicidal action.

We have also found that compounds of the formula I have a good insecticidal, nematicidal and acaricidal action. The fungicidal action is preferred.

With a view to their biological activity for controlling fungal pests, suitable compounds I are those where, for example:

X is $C_1$–$C_4$-alkylidene such as methylene, ethylidene, n- or iso-propylidene, n-, iso- or sec-butylidene;

$C_1$–$C_4$-alkoxymethylene such as methoxy-, ethoxy-, n- or iso-propoxy, n-, iso-, sec- or tert-butoxymethylene;

$C_1$–$C_4$-alkylthiomethylene such as methyl-, ethyl-, n- or iso-propyl, n-, iso-, sec- or tert-butylthiomethylene;

$C_1$–$C_4$-alkoxyimino such as methoxy-, ethoxy-, n- or isopropoxy, n-, iso-, sec- or tert-butoxyimino;

$z^1$ and $Z^2$ are each halogen such as fluorine, chlorine, bromine and iodine or, for example, methyl, methoxy, cyano and nitro;

R and $R^3$ are each hydrogen;

$C_1$–$C_6$-alkyl such as methyl, ethyl, propyl, 1-methylethyl, butyl, 1-methylpropyl, 2-methylpropyl, 1, 1-dimethylethyl, pentyl, 1-methylbutyl, 2-methylbutyl, 3-methylbutyl, 2,2-dimethylpropyl, 1-ethylpropyl, hexyl, 1, 1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1, 3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

$R^1$ is hydrogen;

$C_1$–$C_4$-alkyl such as methyl, ethyl, propyl, 1-methylethyl, butyl, 1-methylpropyl, 2-methylpropyl and 1,1-dimethylethyl;

$C_1$–$C_4$-haloalkyl, especially $C_1$–$C_2$-haloalkyl such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

unsubstituted or substituted aryl such as phenyl, naphthyl and anthryl, preferably phenyl and naphthyl, especially phenyl;

$R^2$ is hydrogen;

$C_1$–$C_6$-alkyl as mentioned above;

$C_1$–$C_4$-haloalkyl as mentioned above;

unsubstituted or substituted $C_3$–$C_{15}$-alkenyl, especially $C_3$-$C_6$-alkenyl such as 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1, 3-dimethyl-2-butenyl, 1,3-dimethyl3-butenyl, 2,2-dimethyl-3-butenyl, 2,3-dimethyl-2-butenyl, 2,3-dimethyl-3-butenyl, 3,3-dimethyl-2-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl; unsubstituted or substituted $C_3$–$C_8$-alkynyl, especially $C_3$–$C_6$-alkynyl such as 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl;

unsubstituted or substituted $C_3$-$C_7$-cycloalkyl such as cyclopropyl, cyclobutyl, cyclopentyl, cyclohexyl, cycloheptyl and cyclooctyl;

$C_1$-$C_4$-alkoxycarbonyl-$C_1$-$C_4$-alkyl such as methoxycarbonylmethyl, ethoxycarbonylmethyl, propyloxycarbonylmethyl, 1-methylethyloxycarbonylmethyl, butyloxycarbonylmethyl, 1-methylpropyloxycarbonylmethyl and 1,1-dimethylethyloxycarbonylmethyl;

unsubstituted or substituted $C_5$-$C_8$-cycloalkenyl such as 1-cyclopentenyl, 2-cyclopentenyl, 3-cyclopentenyl, 1-cyclohexenyl, 2-cyclohexenyl, 3-cyclohexenyl, 1-cycloheptenyl, 2-cycloheptenyl, 3-cycloheptenyl, 4-cycloheptenyl, 1-cyclooctenyl, 2-cyclooctenyl, 3-cyclooctenyl and 1-cyclooctenyl;

unsubstituted or substituted aryl (eg. phenyl, naphthyl and anthryl);

unsubstituted or substituted aryl-$C_1$-$C_4$-alkyl (eg. benzyl, 1-phenethyl, 2-phenethyl, 1-phenylpropyl, 2-phenylpropyl, 3-phenylpropyl, 2-methyl-3-phenylpropyl, 2-methyl-2-phenylpropyl and 4-phenylbutyl);

unsubstituted or substituted acyl, especially $C_1$-$C_4$-alkylcarbonyl such as acetyl, propionyl, butyryl, phenylacetyl and chloroacetyl;

unsubstituted or substituted arylcarbonyl such as benzoyl and 2,4-dichlorobenzoyl;

unsubstituted or substituted hetarylcarbonyl such as 2-pyridylcarbonyl;

unsubstituted or substituted aryl-$C_1$-$C_4$-alkenyl (eg. 1-phenylethenyl, 2-phenyl-1-propenyl, 2,2-diphenylethenyl, 1-methyl-2-phenylethenyl and 1-phenylbutenyl);

unsubstituted or substituted aryloxy-$C_1$-$C_4$-alkyl such as phenoxymethyl, phenoxyethyl and phenoxypropyl;

unsubstituted or substituted hetaryl (eg. 2-pyridyl, 3-pyridyl, 4-pyridyl, 3-pyridazinyl, 4-pyridazinyl, 1-pyrazolyl, 3-pyrazolyl, 4-pyrazolyl, 2-pyrazinyl, 2-pyrimidinyl, 4-pyrimidinyl, 5-pyrimidinyl, 1-indazolyl, 3-indazolyl, 2-furyl, 3-furyl, 1-pyrrolyl, 2-pyrrolyl, 3-pyrrolyl, 2-thienyl, 3-thienyl, 1-imidazolyl, 2-imidazolyl, 4-imidazolyl, 5-imidazolyl, 2-isoindolyl, 1-indolyl, 1-indazolyl, 1,2-benzothiazol-3-yl, 1,3-benzothiazol-2-yl, 3-isoxazolyl, 4-isoxazolyl, 5-isoxazolyl, 3-isothiazolyl, 4-isothiazolyl, 5-isothiazolyl, 1,2-benzoxazol-3-yl, 1,3-benzoxazol-2-yl, 1,2,4-triazolyl, 1,3,4-triazolyl, 7-purinyl, 2-quinolyl, 3-quinolyl, 4-quinolyl, 1-isoquinolyl, 3-isoquinolyl, 4-isoquinolyl, 2-benzofuran-yl, 3-benzofuranyl, 1-isobenzofuranyl, 1,2,4-triazin-3-yl and 1,3,5-triazin-2-yl;

unsubstituted or substituted hetaryl-$C_1$-$C_4$-alkyl (eg. 2-pyridylmethyl, 3-pyridylmethyl);

unsubstituted or substituted hetaryl-$C_2$-$C_4$-alkenyl (eg. 2-(2-furyl)ethenyl, 2-(2-thienyl)ethenyl, 2-(3-pyridyl)ethenyl;

unsubstituted or substituted heterocyclyl (eg. oxiranyl, 1-aziridinyl, 1-azetidinyl, 1-pyrrolidinyl, 2-tetrahydrofuryl, 2-tetrahydropyranyl, 3-tetrahydropyranyl, 1-piperidinyl, 1-morpholinyl, 1-piperazinyl, 1,3-dioxanyl, 3-tetrahydrothiopyranyl).

The unsubstituted or substituted radicals contain besides hydrogen, for example, the following radicals: halogen such as fluorine, chlorine, bromine and iodine; $C_1$-$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

$C_1$-$C_6$-alkyloxy such as methyloxy, ethyloxy, propyloxy, 1-methylethyloxy, butyloxy, 1-methylpropyloxy, 2-methylpropyloxy, 1,1-dimethylethyloxy, pentyloxy, 1-methylbutyloxy, 2-methylbutyloxy, 3-methylbutyloxy, 1,1-dimethylpropyloxy, 1,2-dimethylpropyloxy, 2,2-dimethylpropyloxy, 1-ethylpropyloxy, hexyloxy, 1-methylpentyloxy, 2-methylpentyloxy, 3-methylpentyloxy, 4-methylpentyloxy, 1,1-dimethylbutyloxy, 1,2-dimethylbutyloxy, 1,3-dimethylbutyloxy, 2,2-dimethylbutyloxy, 2,3-dimethylbutyloxy, 3,3-dimethylbutyloxy, 1-ethylbutyloxy, 2-ethylbutyloxy, 1,1,2-trimethylpropyloxy, 1,2,2-trimethylpropyloxy, 1-ethyl-1-methylpropyloxy and 1-ethyl-2-methylpropyloxy;

$C_1$-$C_6$-alkylthio such as methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

$C_1$-$C_4$-haloalkyl, especially $C_1$-$C_2$-haloalkyl such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

$C_1$-$C_4$-haloalkoxy, especially $C_1$-$C_2$-haloalkyloxy such as chloromethyloxy, dichloromethyloxy, trichloromethyloxy, fluoromethyloxy, difluoromethyloxy, trifluoromethyloxy, chlorofluoromethyloxy, dichlorofluoromethyloxy, chlorodifluoromethyloxy, 1-fluoroethyloxy, 2-fluoroethyloxy, 2,2-difluoroethyloxy, 2,2,2-trifluoroethyloxy, 2-chloro-2-fluoroethyloxy, 2-chloro-2,2-difluoroethyloxy, 2,2-dichloro-2-fluoroethyloxy, 2,2,2-trichloroethyloxy and pentafluoroethyloxy;

$C_2$–$C_6$-alkenyloxy such as ethenyloxy, 1-propenyloxy, 2-propenyloxy, 1-methylethenyloxy, 1-butenyloxy, 2-butenyloxy, 3-butenyloxy, 1-methyl-1-propenyloxy, 2-methyl-1-propenyloxy, 1-methyl-2-propenyloxy, 2-methyl-2-propenyloxy, 1-pentenyloxy, 2-pentenyloxy, 3-pentenyloxy, 4-pentenyloxy, 1-methyl-1-butenyloxy, 2-methyl-1-butenyloxy, 3-methyl-1-butenyloxy, 1-methyl-2-butenyloxy, 2-methyl-2-butenyloxy, 3-methyl-2-butenyloxy, 1-methyl-3-butenyloxy, 2-methyl-3-butenyloxy, 3-methyl-3-butenyloxy, 1,1-dimethyl-2-propenyloxy, 1,2-dimethyl-1-propenyloxy, 1,2-dimethyl-2-propenyloxy, 1-ethyl-1-propenyloxy, 1-ethyl-2-propenyloxy, 1-hexenyloxy, 2-hexenyloxy, 3-hexenyloxy, 4-hexenyloxy, 5-hexenyloxy, 1-methyl-1-pentenyloxy, 2-methyl-1-pentenyloxy, 3-methyl-1-pentenyloxy, 4-methyl-1-pentenyloxy, 1-methyl-2-pentenyloxy, 2-methyl-2-pentenyloxy, 3-methyl-2-pentenyloxy, 4-methyl-2-pentenyloxy, 1-methyl-3-pentenyloxy, 2-methyl-3-pentenyloxy, 3-methyl-3-pentenyloxy, 4-methyl-3-pentenyloxy, 1-methyl-4-pentenyloxy, 2-methyl-4-pentenyloxy, 3-methyl-4-pentenyloxy, 4-methyl-4-pentenyloxy, 1,1-dimethyl-2-butenyloxy and 1,1-dimethyl-3-butenyloxy; cyano; cyanato, thiocyanate; nitro; amino; hydroxyl; carboxyl;

$C_1$–$C_6$-alkylamino such as methylamino, ethylamino, propylamino, 1-methylethylamino, butylamino, 1-methylpropylamino, 2-methylpropylamino, 1,1-dimethylethylamino, pentylamino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutylamino, 3,3-dimethylbutylamino, 1-ethylbutylamino, 2-ethylbutylamino, 1,1,2-trimethylpropylamino, 1,2,2-trimethylpropylamino, 1-ethyl-1-methylpropylamino and 1-ethyl-2-methylpropylamino;

di-$C_1$–$C_6$-alkylamino, especially di -alkylamino such as N,N-dimethylamino, N,N-diethylamino, N,N-dipropylamino, N,N-di-(1-methylethyl) amino, N,N-dibutylamino, N,N-di-(1-methylpropyl) amino, N,N-di-(2-methylpropyl) amino, N,N-di(1,1-dimethylethyl)amino, N-ethyl-N-methylamino, N-methyl-N-propylamino, N-methyl-N- (1-methylethyl) amino, N-butyl-N-methylamino, N-methyl-N- (1-methylpropyl) amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(l-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(l-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butylN-(1,1-dimethylethyl)amino, N-(1-methylpropyl)-N-(2-methylpropyl)amino, N-(1,1-dimethylethyl)-N-(l-methylpropyl)amino and N-(1,1-dimethylethyl)-N-(2-methylpropyl)amino;

phenyl, phenoxy, phenylthio and phenylamino, each of which in turn can carry from one to five halogens as mentioned above;

and/or from one to five $C_1$–$C_6$-alkoxy groups as mentioned above;

and/or from one to five $C_1$–$C_6$-alkylthio groups as mentioned above;

and/or from one to five $C_1$–$C_4$-haloalkyl groups as mentioned above;

and/or from one to four $C_1$–$C_6$-alkoxyiminomethyl groups such as methoxyiminomethyl, ethoxyiminomethyl, n-propoxyiminomethyl, n-butoxyiminomethyl, n-pentoxyiminomethyl, n-hexoxyiminomethyl, allyloxyiminomethyl, benzyloxyiminomethyl, isopropoxyiminomethyl, isobutoxyiminomethyl and tert-butoxyiminomethyl, and/or from one to four $C_1$–$C_6$-alkoxyiminoethyl groups such as methoxyiminoethyl, 1-ethoxyiminoethyl, 1-n-propoxyiminoethyl, 1-n-butoxyiminoethyl, 1-n-pentoxyiminoethyl, 1-n-hexoxyiminoethyl, 1-allyloxyiminoethyl, 1-benzyloxyiminoethyl, phenyl, phenoxy and benzyloxy;

and/or one $C_1$–$C_4$-alkyliminomethyl group such as methyliminomethyl and ethyliminomethyl;

and/or from one to four $C_3$–$C_6$-cycloalkyl groups such as cyclopropyl, cyclobutyl, cyclopentyl and cyclohexyl.

The preparation of the novel compounds of the formula I may result in mixtures of E and Z isomers at the C=C and C=N double bonds. These mixtures can be fractionated into the individual components in a conventional manner by crystallization or chromatography.

The present invention embraces both the individual isomers and mixtures thereof, and all of these can be used as fungicides.

The compounds of the formula I as claimed in claim 1 are prepared, for example, as described in Scheme 1 ($Z^1$ and $Z^2$ equal H).

Scheme 1

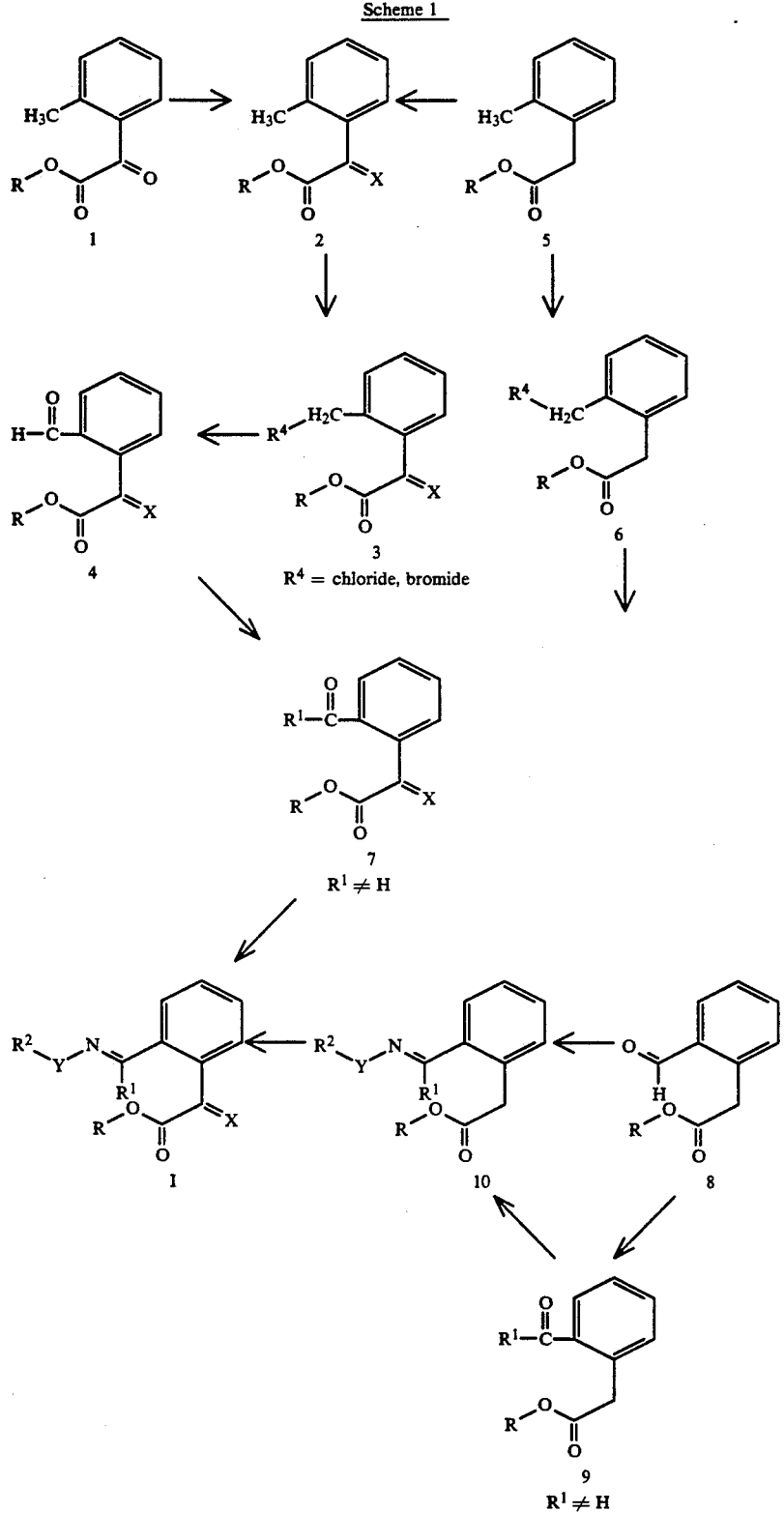

The compounds of the formula I where X=CH₂ or CHalkoxy can be prepared, for example, from the keto esters 1 by a Wittig or Wittig-Horner reaction (cf. EP 348766, DE 3705389, EP 178826).

The compounds of the formula I where X=N—O-alkyl can be prepared from 1 a) by reaction with O-alkylhydroxylamine hydrochloride or b) with hydroxylamine hydrochloride and subsequent alkylation with an alkylating agent (eg. alkyl iodide, dialkyl sulfate etc.) (cf. DE 3623921).

It is likewise possible to use a method similar to that in EP 254 426 and convert a phenylacetic ester of the formula 8 or 9 with a base (eg. NaOMe, NaH, K tertbutylate etc.) in a solvent (eg. diethyl ether, toluene, tert-butanol etc.) into its anion and convert the latter with a suitable nitrosating agent (eg. methyl nitrite, amyl nitrite, tert-butyl nitrite etc.) into the oxime which is then alkylated with an alkylating agent (eg. alkyl iodide, dialkyl sulfate).

Compounds of the formula I with $X=CH_2$ or CH-alkyl can be prepared, for example, from 8 or 9 by condensation with formaldehyde ($X=CH_2$, cf. DE 3317356) or with aldehydes ($X=$CH-alkyl, cf. D. M. Brown, J. Chem. Soc. 1948, 2147).

Compounds of the formula I where $X=$CH—S-alkyl can be prepared by the methods in EP 244077 or 310954.

The intermediates of the formulae 3 and 6 can be prepared from the compounds 2 and 5 by halogenation of the latter by conventional methods, eg. with chlorine, bromine, n-bromosuccinimide in an inert solvent (eg. $CCl_4$, cyclohexane) irradiating with, for example, an Hg vapor lamp, or using free radical initiators such as dibenzoyl peroxide.

Benzaldehydes of the formulae 4 and 8 are either known ($X=$CHOCH$_3$, cf. EP 88 300 280) or can be prepared by oxidation of the benzyl halides 3 or 6, eg. with N-methylmorpholine N-oxide in an inert solvent such as $CCl_4$ or cyclohexane. The benzaldehydes of the formulae 4 and 8 can also be prepared by treating the corresponding benzal halides with an oxidizing agent such as silver nitrate in methanol or ethylene glycol monomethyl ether [cf. J. Am. Chem. Soc. 78 (1956) 1689].

The compounds of the formulae 7 and 9 can be prepared, for example, as described in Scheme 2.

Scheme 2

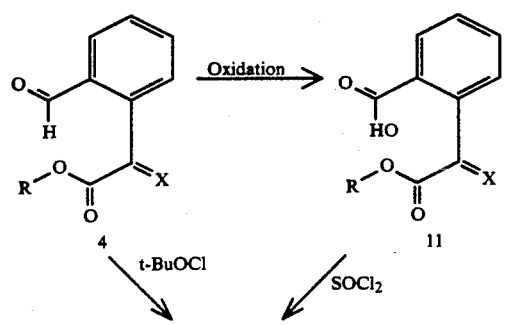

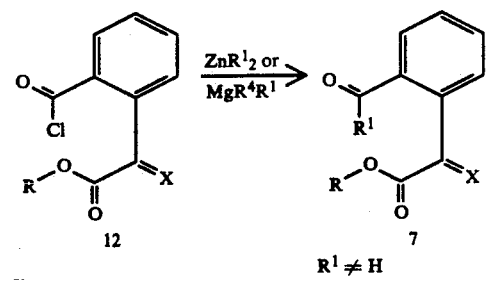

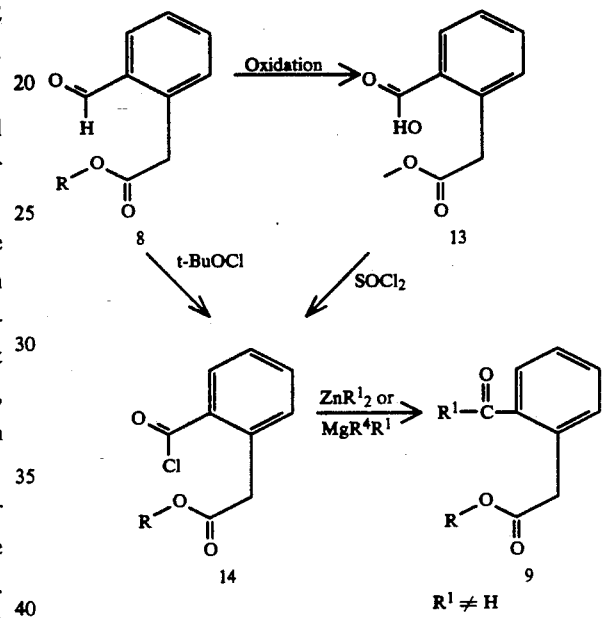

The benzaldehydes 4 and 8 can be converted in a conventional manner into the carboxylic acids 11 and 13 [cf. Organikum, 15th edition, 447 (1977)].

The chlorides 12 and 14 can be prepared from the resulting carboxylic acids 11 and 13 in a conventional manner [cf. Organikum, 15th edition, 526 et seq. (1977)].

Alternatively, the chlorides 12 and 14 can also be obtained directly from the benzaldehydes 4 and 8 by treatment thereof with, for example, t-BuOCl in an inert solvent such as $CCl_4$ [cf. D. Ginsburg, J. Amer. Chem. Soc. 73 (1951) 702]. The ketones 7 and 9 are obtained, for example, from the chlorides 12 and 14 by reaction with organozinc compounds of the type $ZnR^1_2$ (cf. Org. React. 8 (1954) 28).

Compounds of the formulae V, VI, VII, VIII, IX and X according to the invention are prepared, for example, as described in Scheme 3.

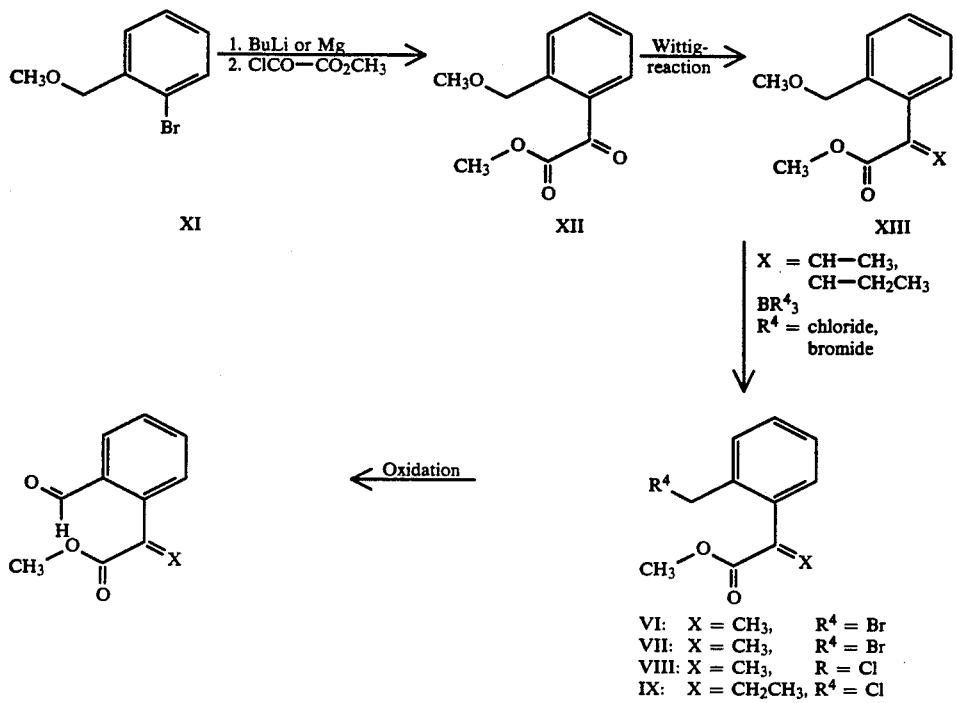

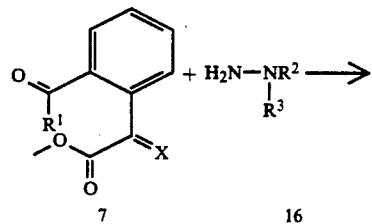

The intermediates of the formula XIII where X=CH₃ or CH₂CH₃ can be prepared from the keto esters XII by Wittig or Wittig-Horner reaction (cf. EP 348766).

The intermediates of the formulae V-IX can be prepared from XIII by reaction with BCl₃ or BBr₃ in an inert solvent (eg. CCl₄, CH₂Cl₂, cyclohexane) [cf. Synthesis (1983) 249 et seq.].

The novel compounds of the formula I can be prepared in such a way that the novel carbonyl compounds of the formula 7 are reacted with a substituted hydroxylamine of the formula 15 or hydrazine of the formula 16 or with an acid addition salt (eg. hydrochloride or hydrobromide) of 15 or 16.

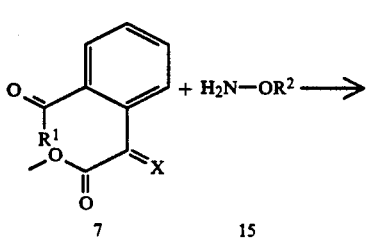

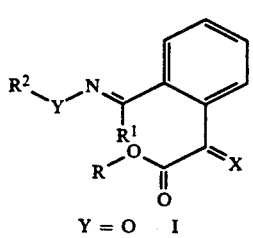

The reaction can be carried out in an inert solvent or diluent (eg. methanol, ethanol, toluene) or in a two-phase system (eg. toluene/water). It may also be advantageous to add a base (eg. triethylamine, sodium carbonate, potassium carbonate, sodium bicarbonate, potassium bicarbonate, sodium hydroxide, potassium hydroxide) to the reaction mixture.

An alternative procedure for the preparation of I is as follows (Scheme 4, $Z^1$, $Z^2$=H).

Scheme 4
(Y = O)

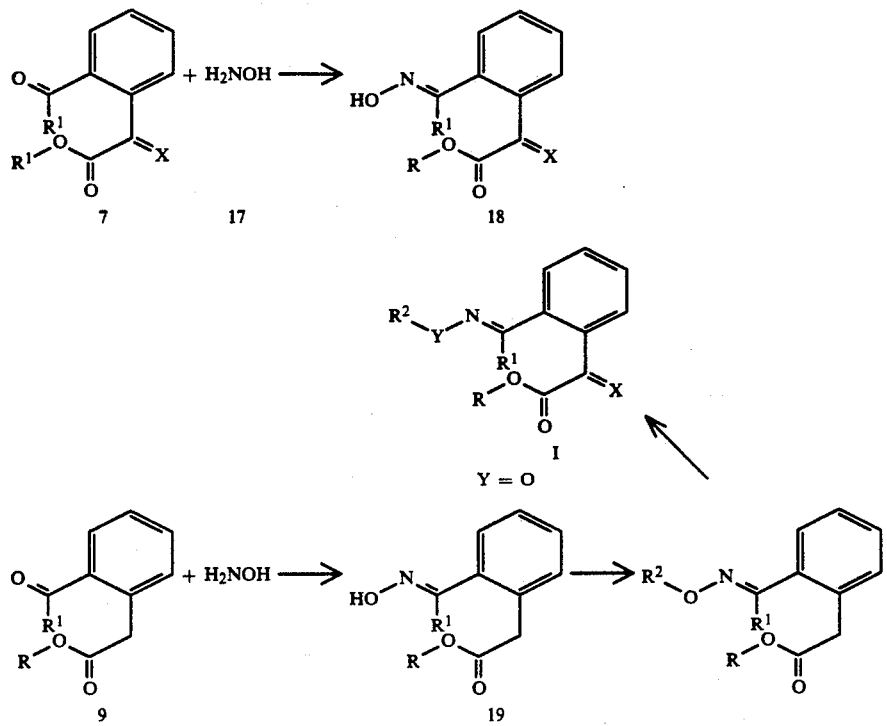

The oximes 18 and 19 (cf. Scheme 4) required for the preparation of compounds of the formula I (Y=O) can be prepared from the corresponding carbonyl compounds 7 and 9 in a conventional manner (cf. Houben-Weyl, Vol. 10/4 (1968)) by reaction with the hydroxylamine 17.

The reaction can be carried out in an inert solvent or diluent (eg. methanol, ethanol, toluene) or in a two-phase system (eg. toluene/water). It may also be advantageous to add a base (eg. triethylamine, sodium carbonate, potassium carbonate, sodium bicarbonate, potassium bicarbonate, sodium hydroxide, potassium hydroxide) to the reaction mixture.

The subsequent alkylation of the oximes 18 and 19 is carried out in a conventional manner using a base (eg. NaOMe, NaH, KOtBu in a solvent such as diethyl ether, toluene, dimethylformamide etc.) (cf. DE 3623921).

Hydroxylamines of the formula 15 ($H_2N$—$OR^2$) are either known or can be prepared by methods similar to those disclosed in Houben-Weyl X/1, 1192, 1183.

Hydrazine derivatives of the formula 16

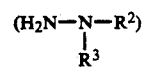

are either known or can likewise be prepared by methods similar to those disclosed in Houben-Weyl X/2, 271, 280, 740.

Another way of obtaining compounds of the formula I is described in Scheme 5 ($Z^1$, $Z^2$=H, $R^5$=methyl, ethyl).

Scheme 5

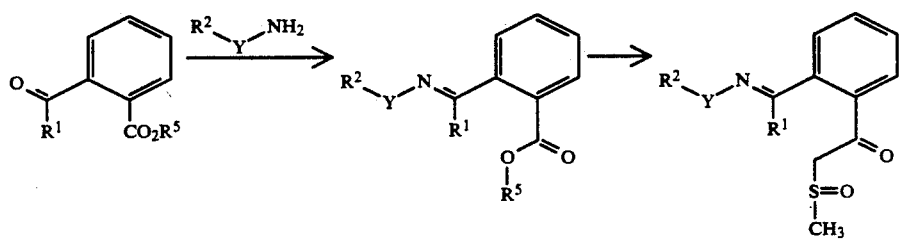

Scheme 5

-continued

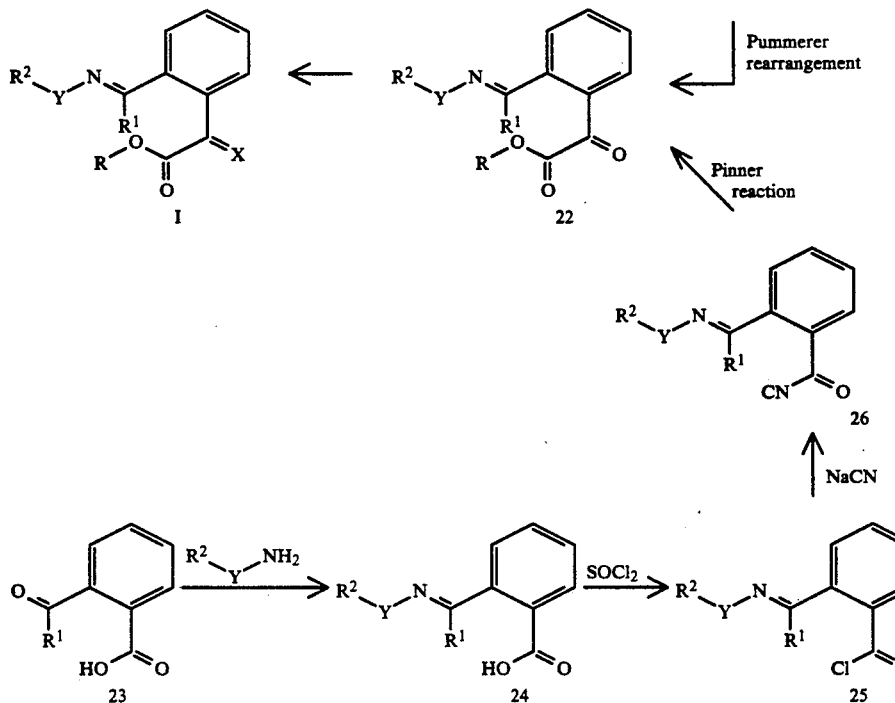

The β-keto sulfoxides 21 can be obtained from the carboxylic esters of the formula 20 by the formation of an adduct with dimethyl sulfoxide in the presence of a strong base (eg. NaOCH₃, KOtBu) (cf. J. Amer. Chem. Soc. 88 (1966) 5498) and are brominated and then boiled with an alcohol (eg. methanol, ethanol) in the presence of an acid to give, in a Pumaerer rearrangement, the α-keto esters 22 (Synthesis (1982) 47).

Alternatively, the α-keto esters of the formula 22 can be obtained by Pinner reaction of the acyl cyanides of the formula 26 (cf. S. Hünig et al. Ang. Chemie 94 (1982) 1).

The carboxylic acids 24 are converted into the acyl cyanides 26 in a conventional manner (cf. Organikum, 16th edition, Berlin 1986, 423 et seq. and J. M. Photis, Tetr. Lett. 21 (1980) 3539–3540).

The intermediates of the formula 19 can be prepared from o-hydroxyphenyl ketones of the formula 27 as described in Tete. Letters (1990) 6781 (Scheme 6).

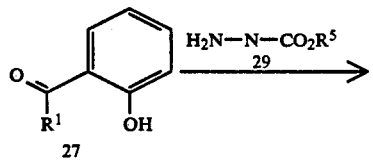

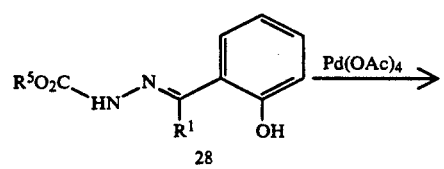

-continued

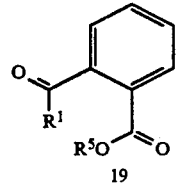

The following methods and Examples are intended to illustrate the preparation of the novel active ingredients and novel intermediates.

METHOD 1

Preparation of methyl alpha-(2-formylphenyl)-β-methoxyacrylate 35.5 g (0.125 mol) of methyl alpha-(2-bromomethylphenyl)-β-methoxyacrylate are dissolved in 500 ml of $CCl_4$. 43.4 g (0.321 mol) of methylmorpholine N-oxide monohydrate are added, and the mixture is refluxed for 20 hours. The solid is filtered off and the $CCl_4$ phase is washed with water, with 2 N hydrochloric acid and again with water, dried and concentrated. 18.5 g (67%) of product are obtained as a reddish brown oil.

$^1$H-NMR (CDCl3): 3.7(s,3H); 3.8(s,3H); 7.2≈7.6(m,4H); 7.9(m,1H); 10.0 ppm (s,1H).

METHOD 2

Preparation of methyl 2-formylphenylglyoxylate O-methyloxime 20 g (0.070 mol) of methyl 2-(bromomethyl)phenylglyoxylate O-methyloxime, 32 g (0.237 mol) of N-methylmorpholine N-oxide monohydrate and 300 ml of $CCl_4$ are mixed and heated to reflux. After refluxing for 9 hours, the mixture is filtered, and the organic phase is washed with water and with 2 N hydrochloric acid, dried and concentrated. The residue is recrystallized from pentane. 9.0 g of product (58%) are obtained as colorless crystals.

$^1$H-NMR (CDCl$_3$): 3.9(s,3H); 4.0(s,3H); 7.39-8.0(m,4H); 9.98 ppm (s,1H).

Method 3

Preparation of 1-bromo-2-methoxymethylbenzene 685 g (2.74 mol) of o-bromobenzyl bromide are refluxed together with 2.74 mol of a 30% strength sodium methylate solution in methanol for 15 hours. The mixture is cooled and then concentrated, the residue is taken up in ethyl acetate, and the solution is washed with water. The organic phase is dried over sodium sulfate and then concentrated. 478.2 g (87%) of product are obtained as a colorless liquid.

$^1$H-NMR (CDCl$_3$):3.5(s,3H) ; 4.58(s,2H);7.08-7.6 ppm (m,4H).

METHOD 4

Preparation of methyl 2-methoxymethylphenylglyoxylate

A Grignard solution is prepared from 12.0 g (0.46 mol) of magnesium turnings and 99.5 g (0.5 mol) of 1-bromo-2-methoxymethylbenzene in 500 ml of THF (tetrahydrofuran) and then 500 ml of 1 N ethereal zinc chloride solution are added dropwise. The mixture is refluxed for 1 hour and then a solution of 61.2 g (0.5 mol) of methyl oxalyl chloride in 100 ml of THF is added at −10° C. The mixture is allowed to reach room temperature (20° C.), is stirred for a further 20 hours at room temperature and then hydrolyzed with ammonium chloride solution. After extraction with ether, the combined ether phases are washed with water, dried and concentrated. 60 g of product (57.7%) are obtained as a mobile liquid.

$^1$H-NMR (CDCl$_3$):3.38(s,3H); 3.98(s,3H); 4.8(s,2H); 7.3-7.7 ppm (m,4H).

METHOD 5

Preparation of methyl 2-methoxymethylphenyl-β-methylacrylate 37.1 g (100 mmol) of ethyltriphenylphosphonium bromide are introduced under nitrogen into 300 ml of absolute tetrahydrofuran. At 5° C., 11.2 g (0.1 mol) of potassium t-butanolate are added. After stirring at 5° C. for one hour, 20.8 g (100 mmol) of methyl 2-methoxymethylphenylglyoxylate in 100 ml of tetrahydrofuran are added dropwise. The mixture is stirred at 5° C. for one hour and at 25° C. for one hour, 200 ml of water are added, the mixture is extracted with methylene chloride and the organic phases are washed with water. After drying over sodium sulfate, the solvent is removed under reduced pressure. The residue is purified by chromatography on a silica gel column (methyl tert-butyl ether/n-hexane=⅓). 17.2 g (78%) of the abovementioned ester are obtained as an oil (Z/E isomer=1/9).

$^1$H-NMR (CDCl$_3$):1.8(d,3H); 3.3(s,3H); 3.7(s,3H); 4.3(d,2H); 7.05(m,1H); 7.2-7.6 ppm (m,4H).

METHOD 6

Preparation of methyl 2-bromomethylphenyl-β-methylacrylate 105.3 ml (140 mmol) of a 1.33 N boron trobromide solution in methylene chloride are added dropwise to 31 g (140 mmol) of methyl 2-methoxymethylphenyl-β-methylacrylate in 500 ml of methylene chloride at 0° C., and the mixture is then refluxed for three hours. Subsequently 5 ml of methanol are added, and the mixture is stirred at room temperature for a further 5 hours and hydrolyzed with 3% strength sodium hydroxide solution. The organic phases are then washed with water, dried over sodium sulfate and concentrated. 31.0 g of the abovementioned benzyl bromide are obtained as a yellowish oil (compound VI).

$^1$H-NMR (CDCl$_3$) 1.65(d,3H); 3.7(s,3H); 4.28(d,2H); 7.05(m,1H); 7.2-7.6 ppm (m,4H).

EXAMPLE 1

Preparation of methyl 2-(2-methylbenzyloximinomethyl)phenylglyoxylate O-methyloxime 4 g (29 mmol) of 0-(2-methylbenzyl)hydroxylamine are added to a solution of 6 g (27 mmol) of methyl 2-formylphenylglyoxylate O-methyloxime in 150 ml of methanol, and the mixture is stirred at 65° C. for 8 hours. It is then allowed to cool to room temperature and is taken up in ethyl acetate, and the organic phase is washed with water. Drying over sodium sulfate and removal of the solvent result in 9 g (98%) of the abovementioned oxime ether in the form of yellowish crystals (compound No. 1.35, Table I).

Melting point 80°-83° C. $^1$H-NMR ( CDCl$_3$ ):2.4(s,3H); 3.8(s,3H); 3.98(s,3H); 5.2(s,2H); 7.05-7.8(m,8H), 8.05 ppm (s,1H).

EXAMPLE 2

Preparation of the phenylhydrazone of methyl alpha-(2-formylphenyl)-β-methoxyacrylate A solution of 3.5 g (16 mmol) of methyl alpha-(2-formylphenyl)-β-methoxyacrylate in 5 ml of methanol is added dropwise at 25° C. to a solution of 1.5 g (14 mmol) of phenylhydrazine in 20 ml of methanol, and the mixture is then stirred at 25° C. for 20 hours. The product is filtered off with suction, carefully washed with ether and dried. 3.4 g (79%) of the abovementioned compound are obtained in the form of pale beige crystals (compound No. 5.20, Table V).

Melting point 210° C. (decomposition)

$^1$H-NMR (DMSO): 3.65(s,3H); 3.85(s,3H); 7.8(s,1H); 7.8(m,1H); 6.75-7.95(m,9H); 10.45 ppm (s,1H).

The compounds listed in the following tables can be prepared in a corresponding manner.

TABLE I

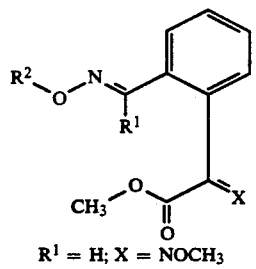

$R^1 = H; X = NOCH_3$

| Comp. no. | $R^2$ | IR (cm$^{-1}$) |
|---|---|---|
| 1.1 | H | 1726, 1442, 1320, 1225, 1205, 1062, 1018, 970, 958, 757 |
| 1.2 | $CH_3$ | 1728, 1493, 1215, 1073, 1053, 1019 |
| 1.3 | $CH_3CH_2$ | |
| 1.4 | $CH_3CH_2CH_2$ | |
| 1.5 | $CH_2\!=\!CH\!-\!CH_2$ | |
| 1.6 | $CH_3\!-\!CH\!\equiv\!CH$ | |
| 1.7 | $CH_3\!-\!CH\!=\!CH\!-\!CH(CH_3)$ | |
| 1.8 | $HC\!\equiv\!C\!-\!\underset{\underset{CH_3}{\vert}}{C}\!=\!CH\!-\!CH_2$ | 1728, 1438, 1214, 1072, 1043, 1019, 960 |
| 1.9 | $HC\!\equiv\!C\!-\!CH_2$ | 1727, 1438, 1313, 1220, 1072, 1046, 1011 |
| 1.10 | $CH_3\!-\!O\!-\!CH_2\!-\!CH_2$ | |
| 1.11 | $C_2H_5\!-\!O\!-\!CH_2\!-\!CH_2$ | |
| 1.12 | $Cl\!-\!CH_2\!-\!CH_2$ | |
| 1.13 | Cyclo-$C_3H_5\!-\!CH_2$ | |
| 1.14 | $CH_3\!-\!CH\!=\!CH\!-\!CH_2$ | |
| 1.15 | $CH_2\!=\!CH\!-\!CH_2\!-\!CH_2$ | |
| 1.16 | $CH_3\!-\!C\!\equiv\!C\!-\!CH_2$ | |
| 1.17 | $CH_3CH_2\!-\!C\!\equiv\!C\!-\!CH_2$ | |
| 1.18 | $CH_3\!-\!(CH_2)_3$ | 1729, 1438, 1324, 1215, 1071, 1044, 1019, 960 |
| 1.19 | $CH_3\!-\!(CH_2)_4$ | |
| 1.20 | $(CH_3)_3C$ | 1728, 1213, 1071, 1019, 961 |
| 1.21 | Cyclo-$C_6H_{11}$ | |
| 1.22 | 2-$CH_3$-Cyclo-$C_6H_{10}$ | |
| 1.23 | $C_6H_5\!-\!CH_2$ | |
| 1.24 | 2-F—$C_6H_4$—$CH_2$ | |
| 1.25 | 3-F—$C_6H_4$—$CH_2$ | |
| 1.26 | 4-F—$C_6H_4$—$CH_2$ | |
| 1.27 | 2-Cl—$C_6H_4$—$CH_2$ | |
| 1.28 | 3-Cl—$C_6H_4$—$CH_2$ | 1727, 1436, 1213, 1071, 1019, 959 |
| 1.29 | 4-Cl—$C_6H_4$—$CH_2$ | 1728, 1492, 1437, 1218, 1071, 1015, 988, 959 |
| 1.30 | 2,3-$Cl_2$—$C_6H_3$—$CH_2$ | |
| 1.31 | 2,4-$Cl_2$—$C_6H_3$—$CH_2$ | |
| 1.32 | 2,5-$Cl_2$—$C_6H_3$—$CH_2$ | |
| 1.33 | 2,6-$Cl_2$—$C_6H_3$—$CH_2$ | |
| 1.34 | 3,4-$Cl_2$—$C_6H_3$—$CH_2$ | |
| 1.35 | 2-$CH_3$—$C_6H_4$—$CH_2$ | 1723, 1212, 1071, 1042, 1013, 958 |
| 1.36 | 3-$CH_3$—$C_6H_4$—$CH_2$ | 1728, 1437, 1213, 1072, 1019, 959 |
| 1.37 | 4-$CH_3$—$C_6H_4$—$CH_2$ | 1728, 1437, 1219, 1070, 1018, 959, 755 |
| 1.38 | 2,3-$(CH_3)_2$—$C_6H_3$—$CH_2$ | |
| 1.39 | 2,4-$(CH_3)_2$—$C_6H_3$—$CH_2$ | |
| 1.40 | 2,5-$(CH_3)_2$—$C_6H_3$—$CH_2$ | |
| 1.41 | 3,4-$(CH_3)_2$—$C_6H_3$—$CH_2$ | |
| 1.42 | 3,5-$(CH_3)_2$—$C_6H_3$—$CH_2$ | |
| 1.43 | 4,5-$(CH_3)_2$—$C_6H_3$—$CH_2$ | |
| 1.44 | 2,3,4-$(CH_3)_3$—$C_6H_2$—$CH_2$ | |
| 1.45 | 2,4,5-$(CH_3)_3$—$C_6H_2$—$CH_2$ | |
| 1.46 | 2,4,6-$(CH_3)_3$—$C_6H_2$—$CH_2$ | |
| 1.47 | 2,3,6-$(CH_3)_3$—$C_6H_2$—$CH_2$ | |
| 1.48 | 2-$CF_3$—$C_6H_4$—$CH_2$ | |
| 1.49 | 3-$CF_3$—$C_6H_4$—$CH_2$ | |
| 1.50 | 4-$CF_3$—$C_6H_4$—$CH_2$ | |
| 1.51 | 2-$CH_3$-3-$CF_3$—$C_6H_3$—$CH_2$ | |
| 1.52 | 2-$CH_3$-4-$CF_3$—$C_6H_3$—$CH_2$ | |
| 1.53 | 2-$CF_3$-3-$CH_3$—$C_6H_3$—$CH_2$ | |
| 1.54 | 2-$CF_3$-4-$CH_3$—$C_6H_3$—$CH_2$ | |
| 1.55 | 2-$CF_3$-5-$CH_3$—$C_6H_3$—$CH_2$ | |
| 1.56 | 2-$CH_3$-5-$CF_3$—$C_6H_3$—$CH_2$ | |
| 1.57 | 2-Br—$C_6H_4$—$CH_2$ | |
| 1.58 | 3-Br—$C_6H_4$—$CH_2$ | |
| 1.59 | 4-Br—$C_6H_4$—$CH_2$ | |
| 1.60 | 2-(iso-Propyl)-$C_6H_4$—$CH_2$ | |
| 1.61 | 3-(iso-Propyl)-$C_6H_4$—$CH_2$ | |
| 1.62 | 4-(iso-Propyl)-$C_6H_4$—$CH_2$ | |
| 1.63 | 2-(iso-Propyl)-3-Cl—$C_6H_3$—$CH_2$ | |

TABLE I-continued

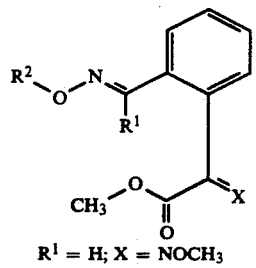

$R^1 = H; X = NOCH_3$

| Comp. no. | $R^2$ | IR (cm$^{-1}$) |
|---|---|---|
| 1.64 | 2-(iso-Propyl)-4-Cl—C$_6$H$_3$—CH$_2$ | |
| 1.65 | 2-(iso-Propyl)-5-Cl—C$_6$H$_3$—CH$_2$ | |
| 1.66 | 2-CH$_3$-3-(iso-Propyl)-C$_6$H$_3$—CH$_2$ | |
| 1.67 | 2-CH$_3$-4-(iso-Propyl)-C$_6$H$_3$—CH$_2$ | |
| 1.68 | 2-CH$_3$-5-(iso-Propyl)-C$_6$H$_3$—CH$_2$ | |
| 1.69 | 2-t-C$_4$H$_9$—C$_6$H$_4$—CH$_2$ | |
| 1.70 | 3-t-C$_4$H$_9$—C$_6$H$_4$—CH$_2$ | |
| 1.71 | 4-t-C$_4$H$_9$—C$_6$H$_4$—CH$_2$ | |
| 1.72 | 2-CH$_3$-3-t-C$_4$H$_9$—C$_6$H$_3$—CH$_2$ | |
| 1.73 | 2-CH$_3$-4-t-C$_4$H$_9$—C$_6$H$_3$—CH$_2$ | |
| 1.74 | 2-CH$_3$-5-t-C$_4$H$_9$—C$_6$H$_3$—CH$_2$ | |
| 1.75 | 3-CH$_3$-4-t-C$_4$H$_9$—C$_6$H$_3$—CH$_2$ | |
| 1.76 | 3-CH$_3$-5-t-C$_4$H$_9$—C$_6$H$_3$—CH$_2$ | |
| 1.77 | 2-Cl-3-t-C$_4$H$_9$—C$_6$H$_3$—CH$_2$ | |
| 1.78 | 2-Cl-4-t-C$_4$H$_9$—C$_6$H$_3$—CH$_2$ | |
| 1.79 | 2-Cl-5-t-C$_4$H$_9$—C$_6$H$_3$—CH$_2$ | |
| 1.80 | 3-Cl-4-t-C$_4$H$_9$—C$_6$H$_3$—CH$_2$ | |
| 1.81 | 3-Cl-5-t-C$_4$H$_9$—C$_6$H$_3$—CH$_2$ | |
| 1.82 | 2-OCH$_3$—C$_6$H$_4$—CH$_2$ | |
| 1.83 | 3-OCH$_3$—C$_6$H$_4$—CH$_2$ | |
| 1.84 | 4-OCH$_3$—C$_6$H$_4$—CH$_2$ | |
| 1.85 | 2-CH$_3$-3-OCH$_3$—C$_6$H$_3$—CH$_2$ | |
| 1.87 | 2-CH$_3$-5-OCH$_3$—C$_6$H$_3$—CH$_2$ | |
| 1.88 | 3-CH$_3$-4-OCH$_3$—C$_6$H$_3$—CH$_2$ | |
| 1.89 | 3-CH$_3$-5-OCH$_3$—C$_6$H$_3$—CH$_2$ | |
| 1.90 | 2-Cl-3-OCH$_3$—C$_6$H$_3$—CH$_2$ | |
| 1.91 | 2-Cl-4-OCH$_3$—C$_6$H$_3$—CH$_2$ | |
| 1.92 | 2-Cl-5-OCH$_3$—C$_6$H$_3$—CH$_2$ | |
| 1.93 | 2-OCH$_3$-3-Cl—C$_6$H$_3$—CH$_2$ | |
| 1.94 | 2-OCH$_3$-4-Cl—C$_6$H$_3$—CH$_2$ | |
| 1.95 | 2-OCH$_3$-5-Cl—C$_6$H$_3$—CH$_2$ | |
| 1.96 | 2-CH$_3$-4-(Cyclohexyl)-C$_6$H$_3$—CH$_2$ | |
| 1.97 | 2-CH$_3$-4-C$_6$H$_5$—C$_6$H$_3$—CH$_2$ | |
| 1.98 | 2-CH$_3$-3-Br-C$_6$H$_3$—CH$_2$ | |
| 1.99 | 2-CH$_3$-4-Br-C$_6$H$_3$—CH$_2$ | |
| 1.100 | 2-CH$_3$-5-Br-C$_6$H$_3$—CH$_2$ | |
| 1.101 | 2-CH$_3$-3-(Methoxyiminomethyl)-C$_6$H$_3$—CH$_2$ | |
| 1.102 | 2-Methoxyiminomethyl-C$_6$H$_4$—CH$_4$ | |
| 1.103 | 3-Methoxyiminomethyl-C$_6$H$_4$—CH$_4$ | |
| 1.104 | 2-CH$_3$-4-(Methoxyiminomethyl)-C$_6$H$_3$—CH$_2$ | |
| 1.105 | 2-Phenyl-C$_6$H$_4$—CH$_2$ | |
| 1.106 | 3-Phenyl-C$_6$H$_4$—CH$_2$ | |
| 1.107 | 4-Phenyl-C$_6$H$_4$—CH$_2$ | |
| 1.108 | 2-Phenoxy-C$_6$H$_4$—CH$_2$ | |
| 1.109 | 3-Phenoxy-C$_6$H$_4$—CH$_2$ | |
| 1.110 | 4-Phenoxy-C$_6$H$_4$—CH$_2$ | |
| 1.111 | 2-Benzyloxy-C$_6$H$_4$—CH$_2$ | |
| 1.112 | 3-Benzyloxy-C$_6$H$_4$—CH$_2$ | |
| 1.113 | 4-Benzyloxy-C$_6$H$_4$—CH$_2$ | |
| 1.114 | 1-Naphthyl-CH$_2$ | 1727, 1437, 1219, 1070, 1018, 793 |
| 1.115 | 2-Naphthyl-CH$_2$ | 1724, 1334, 1211, 1070, 1012, 959, 753 |
| 1.116 | 9-Anthryl-CH$_2$ | |
| 1.117 | 2-CH$_3$-3-C$_6$H$_5$O—C$_6$H$_3$—CH$_2$ | |
| 1.118 | 2-CH$_3$-4-C$_6$H$_5$O—C$_6$H$_3$—CH$_2$ | |
| 1.119 | 2-CH$_3$-5-C$_6$H$_5$O—C$_6$H$_3$—CH$_2$ | |
| 1.120 | 3-CH$_3$-4-C$_6$H$_5$O—C$_6$H$_3$—CH$_2$ | |
| 1.121 | 4-CH$_3$-5-C$_6$H$_5$O—C$_6$H$_3$—CH$_2$ | |
| 1.122 | 2-Cl-3-C$_6$H$_5$O—C$_6$H$_3$—CH$_2$ | |
| 1.123 | 2-Cl-4-C$_6$H$_5$O—C$_6$H$_3$—CH$_2$ | |
| 1.124 | 2-Cl-5-C$_6$H$_5$O—C$_6$H$_3$—CH$_2$ | |
| 1.125 | 3-Cl-4-C$_6$H$_5$O—C$_6$H$_3$—CH$_2$ | |
| 1.126 | 3-Cl-5-C$_6$H$_4$O—C$_6$H$_3$—CH$_2$ | |
| 1.127 | 2-CH$_3$-4-CO$_2$CH$_3$—C$_6$H$_3$—CH$_2$ | |
| 1.128 | 2-CH$_3$-5-CO$_2$CH$_3$—C$_6$H$_3$—CH$_2$ | |
| 1.129 | C$_6$H$_5$—CH(CH$_3$) | |
| 1.130 | 2-F—C$_6$H$_4$—CH(CH$_3$) | |
| 1.131 | 2-F—C$_6$H$_4$—CH(CH$_3$) | |

TABLE I-continued

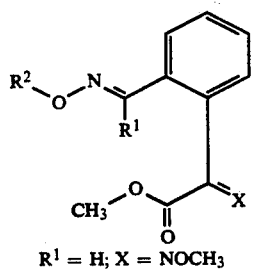

$R^1 = H; X = NOCH_3$

| Comp. no. | $R^2$ | IR (cm$^{-1}$) |
|---|---|---|
| 1.132 | 4-F—C$_6$H$_4$—CH(CH$_3$) | |
| 1.133 | 2-Cl—C$_6$H$_4$—CH(CH$_3$) | |
| 1.134 | 3-Cl—C$_6$H$_4$—CH(CH$_3$) | |
| 1.135 | 4-Cl—C$_6$H$_4$—CH(CH$_3$) | |
| 1.136 | 2,3-Cl$_2$—C$_6$H$_3$—CH(CH$_3$) | |
| 1.137 | 2,4-Cl$_2$—C$_6$H$_3$—CH(CH$_3$) | |
| 1.138 | 2,5-Cl$_2$—C$_6$H$_3$—CH(CH$_3$) | |
| 1.139 | 2,6-Cl$_2$—C$_6$H$_3$—CH(CH$_3$) | |
| 1.140 | 3,4-Cl$_2$—C$_6$H$_3$—CH(CH$_3$) | |
| 1.141 | 2-CH$_3$—C$_6$H$_4$—CH(CH$_3$) | |
| 1.142 | 3-CH$_3$—C$_6$H$_4$—CH(CH$_3$) | |
| 1.143 | 4-CH$_3$—C$_6$H$_4$—CH(CH$_3$) | |
| 1.144 | 2,3-(CH$_3$)$_2$—C$_6$H$_3$—CH(CH$_3$) | |
| 1.145 | 2,4-(CH$_3$)$_2$—C$_6$H$_3$—CH(CH$_3$) | |
| 1.146 | 2,5-(CH$_3$)$_2$—C$_6$H$_3$—CH(CH$_3$) | |
| 1.147 | 3,4-(CH$_3$)$_2$—C$_6$H$_3$—CH(CH$_3$) | |
| 1.148 | 3,5-(CH$_3$)$_2$—C$_6$H$_3$—CH(CH$_3$) | |
| 1.149 | 4,5-(CH$_3$)$_2$—C$_6$H$_3$—CH(CH$_3$) | |
| 1.150 | 2,3,4-(CH$_3$)$_3$—C$_6$H$_3$—CH(CH$_3$) | |
| 1.151 | 2,4,5-(CH$_3$)$_3$—C$_6$H$_3$—CH(CH$_3$) | |
| 1.152 | 2,4,6-(CH$_3$)$_3$—C$_6$H$_3$—CH(CH$_3$) | |
| 1.153 | 2,2,6-(CH$_3$)$_3$—C$_6$H$_3$—CH(CH$_3$) | |
| 1.154 | 2-CF$_3$—C$_6$H$_4$—CH(CH$_3$) | |
| 1.155 | 2-CF$_3$—C$_6$H$_4$—CH(CH$_3$) | |
| 1.156 | 4-CF$_3$—C$_6$H$_4$—CH(CH$_3$) | |
| 1.157 | 2-CH$_3$-3-CF$_3$—C$_6$H$_3$—CH(CH$_3$) | |
| 1.158 | 2-CH$_3$-4-CF$_3$—C$_6$H$_3$—CH(CH$_3$) | |
| 1.159 | 2-CF$_3$-3-CH$_3$—C$_6$H$_3$—CH(CH$_3$) | |
| 1.160 | 2-CF$_3$-4-CH$_3$—C$_6$H$_3$—CH(CH$_3$) | |
| 1.161 | 2-CF$_3$-5-CH$_3$—C$_6$H$_3$—CH(CH$_3$) | |
| 1.162 | 2-CH$_3$-5-CF$_3$—C$_6$H$_3$—CH(CH$_3$) | |
| 1.163 | 2-Br—C$_6$H$_4$—CH(CH$_3$) | |
| 1.164 | 3-Br—C$_6$H$_4$—CH(CH$_3$) | |
| 1.165 | 4-Br—C$_6$H$_4$—CH(CH$_3$) | |
| 1.166 | 2-(iso-Propyl)-C$_6$H$_4$—CH(CH$_3$) | |
| 1.167 | 3-(iso-Propyl)-C$_6$H$_4$—CH(CH$_3$) | |
| 1.168 | 4-(iso-Propyl)-C$_6$H$_4$—CH(CH$_3$) | |
| 1.169 | 2-(iso-Propyl)-3-Cl—C$_6$H$_3$—CH(CH$_3$) | |
| 1.170 | 2-(iso-Propyl)-4-Cl—C$_6$H$_3$—CH(CH$_3$) | |
| 1.171 | 2-(iso-Propyl)-5-Cl—C$_6$H$_3$—CH(CH$_3$) | |
| 1.172 | 2-CH$_3$-3-(iso-Propyl)-C$_6$H$_3$—CH(CH$_3$) | |
| 1.173 | 2-CH$_3$-4-(iso-Propyl)-C$_6$H$_3$—CH(CH$_3$) | |
| 1.174 | 2-CH$_3$-5-(iso-Propyl)-C$_6$H$_3$—CH(CH$_3$) | |
| 1.175 | 2-t-C$_4$H$_9$—C$_6$H$_4$—CH—(CH$_3$) | |
| 1.176 | 3-t-C$_4$H$_9$—C$_6$H$_4$—CH—(CH$_3$) | |
| 1.177 | 4-t-C$_4$H$_9$—C$_6$H$_4$—CH(CH$_3$) | |
| 1.178 | 2-CH$_3$-3-t-C$_4$H$_9$—C$_6$H$_3$—CH(CH$_3$) | |
| 1.179 | 2-CH$_3$-4-t-C$_4$H$_9$—C$_6$H$_3$—CH(CH$_3$) | |
| 1.180 | 2-CH$_3$-5-t-C$_4$H$_9$—C$_6$H$_3$—CH(CH$_3$) | |
| 1.181 | 3-CH$_3$-4-t-C$_4$H$_9$—C$_6$H$_3$—CH(CH$_3$) | |
| 1.182 | 3-CH$_3$-5-t-C$_4$H$_9$—C$_6$H$_3$—CH(CH$_3$) | |
| 1.183 | 2-Cl-3-t-C$_4$H$_9$—C$_6$H$_3$—CH(CH$_3$) | |
| 1.184 | 2-Cl-4-t-C$_4$H$_9$—C$_6$H$_3$—CH(CH$_3$) | |
| 1.185 | 2-Cl-5-t-C$_4$H$_9$—C$_6$H$_3$—CH(CH$_3$) | |
| 1.186 | 3-Cl-4-t-C$_4$H$_9$—C$_6$H$_3$—CH(CH$_3$) | |
| 1.187 | 3-Cl-5-t-C$_4$H$_9$—C$_6$H$_3$—CH(CH$_3$) | |
| 1.188 | 2-OCH$_3$—C$_6$H$_4$—CH$_2$—CH(CH$_3$) | |
| 1.189 | 3-OCH$_3$—C$_6$H$_4$—CH$_2$—CH(CH$_3$) | |
| 1.190 | 4-OCH$_3$—C$_6$H$_4$—CH$_2$—CH(CH$_3$) | |
| 1.191 | 2-CH$_3$-3-OCH$_3$—C$_6$H$_3$—CH(CH$_3$) | |
| 1.192 | 2-CH$_3$-4-OCH$_3$—C$_6$H$_3$—CH(CH$_3$) | |
| 1.193 | 2-CH$_3$-5-OCH$_3$—C$_6$H$_3$—CH(CH$_3$) | |
| 1.194 | 3-CH$_3$-5-OCH$_3$—C$_6$H$_3$—CH(CH$_3$) | |
| 1.195 | 3-CH$_3$-5-OCH$_3$—C$_6$H$_3$—CH(CH$_3$) | |
| 1.196 | 2-Cl-3-OCH$_3$—C$_6$H$_3$—CH(CH$_3$) | |
| 1.197 | 2-Cl-4-OCH$_3$—C$_6$H$_3$—CH(CH$_3$) | |
| 1.198 | 2-Cl-5-OCH$_3$—C$_6$H$_3$—CH(CH$_3$) | |

TABLE I-continued

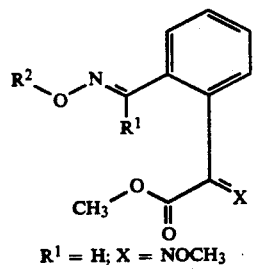

$R^1 = H; X = NOCH_3$

| Comp. no. | $R^2$ | IR (cm$^{-1}$) |
|---|---|---|
| 1.199 | 2-OCH$_3$-3-Cl—C$_6$H$_3$—CH(CH$_3$) | |
| 1.200 | 2-OCH$_3$-4-Cl—C$_6$H$_3$—CH(CH$_3$) | |
| 1.201 | 2-OCH$_3$-5-Cl—C$_6$H$_3$—CH(CH$_3$) | |
| 1.202 | 2-CH$_3$-4-(Cyclohexyl)-C$_6$H$_3$—CH(CH$_3$) | |
| 1.203 | 2-CH$_3$-4-C$_6$H$_5$—C$_6$H$_3$—CH(CH$_3$) | |
| 1.204 | 2-CH$_3$-3-Br—C$_6$H$_3$—CH(CH$_3$) | |
| 1.205 | 2-CH$_3$-4-Br—C$_6$H$_3$—CH(CH$_3$) | |
| 1.206 | 3-CH$_3$-5-Br—C$_6$H$_3$—CH(CH$_3$) | |
| 1.207 | 2-CH$_3$-3-(Methoxyiminomethyl)-C$_6$H$_3$—CH(CH$_3$) | |
| 1.208 | 2-Methoxyiminomethyl-C$_6$H$_4$—CH(CH$_3$) | |
| 1.209 | 3-Methoxyiminomethyl-C$_6$H$_4$—CH(CH$_3$) | |
| 1.210 | 2-CH$_3$-4-(Methoxyiminomethyl)-C$_6$H$_3$—CH(CH$_3$) | |
| 1.211 | 2-Phenyl-C$_6$H$_4$—CH(CH$_3$) | |
| 1.212 | 3-Phenyl-C$_6$H$_4$—CH(CH$_3$) | |
| 1.213 | 4-Phenyl-C$_6$H$_4$—CH(CH$_3$) | |
| 1.214 | 2-Phenoxy-C$_6$H$_4$—CH(CH$_3$) | |
| 1.215 | 3-Phenoxy-C$_6$H$_4$—CH(CH$_3$) | |
| 1.216 | 4-Phenoxy-C$_6$H$_4$—CH(CH$_3$) | |
| 1.217 | 2-Benzyloxy-C$_6$H$_4$—CH(CH$_3$) | |
| 1.218 | 3-Benzyloxy-C$_6$H$_4$—CH(CH$_3$) | |
| 1.219 | 4-Benzyloxy-C$_6$H$_4$—CH(CH$_3$) | |
| 1.220 | 1-Naphthyl-CH(CH$_3$) | |
| 1.221 | 2-Naphthyl-CH(CH$_3$) | |
| 1.222 | 9-Anthryl-CH(CH$_3$) | |
| 1.223 | 2-CH$_3$-3-C$_6$H$_5$O—C$_6$H$_3$—CH(CH$_3$) | |
| 1.224 | 2-CH$_3$-4-C$_6$H$_5$O—C$_6$H$_3$—CH(CH$_3$) | |
| 1.225 | 2-CH$_3$-5-C$_6$H$_5$O—C$_6$H$_3$—CH(CH$_3$) | |
| 1.226 | 3-CH$_3$-4-C$_6$H$_5$O—C$_6$H$_3$—CH(CH$_3$) | |
| 1.227 | 4-CH$_3$-5-C$_6$H$_5$O—C$_6$H$_3$—CH(CH$_3$) | |
| 1.228 | 2-Cl-3-C$_6$H$_5$O—C$_6$H$_3$—CH(CH$_3$) | |
| 1.229 | 2-Cl-4-C$_6$H$_5$O—C$_6$H$_3$—CH(CH$_3$) | |
| 1.230 | 2-Cl-5-C$_6$H$_5$O—C$_6$H$_3$—CH(CH$_3$) | |
| 1.231 | 3-Cl-4-C$_6$H$_5$O—C$_6$H$_3$—CH(CH$_3$) | |
| 1.232 | 3-Cl-5-C$_6$H$_5$O—C$_6$H$_3$—CH(CH$_3$) | |
| 1.233 | 2-CH$_3$-4-CO$_2$CH$_3$—C$_6$H$_3$—CH(CH$_3$) | |
| 1.234 | 2-CH$_3$-5-CO$_2$CH$_3$—C$_6$H$_3$—CH(CH$_3$) | |
| 1.235 | C$_6$H$_5$—(CH$_2$)$_2$ | |
| 1.236 | 2-F—C$_6$H$_4$—(CH$_2$)$_2$ | |
| 1.237 | 2-F—C$_6$H$_4$—(CH$_2$)$_2$ | |
| 1.238 | 4-F—C$_6$H$_4$—(CH$_2$)$_2$ | |
| 1.239 | 2-Cl—C$_6$H$_4$—(CH$_2$)$_2$ | |
| 1.240 | 3-Cl—C$_6$H$_4$—(CH$_2$)$_2$ | |
| 1.241 | 4-Cl—C$_6$H$_4$—(CH$_2$)$_2$ | |
| 1.242 | 2,3-Cl$_2$—C$_6$H$_3$—(CH$_2$)$_2$ | |
| 1.243 | 2,4-Cl$_2$—C$_6$H$_3$—(CH$_2$)$_2$ | |
| 1.244 | 2,5-Cl$_2$—C$_6$H$_3$—(CH$_2$)$_2$ | |
| 1.245 | 2,6-Cl$_2$—C$_6$H$_3$—(CH$_2$)$_2$ | |
| 1.246 | 3,4-Cl$_2$—C$_6$H$_3$—(CH$_2$)$_2$ | |
| 1.247 | 2-CH$_3$—C$_6$H$_4$—(CH$_2$)$_2$ | |
| 1.248 | 3-CH$_3$—C$_6$H$_4$—(CH$_2$)$_2$ | |
| 1.249 | 4-CH$_3$—C$_6$H$_4$—(CH$_2$)$_2$ | |
| 1.250 | 2,3-(CH$_3$)$_2$—C$_6$H$_3$—(CH$_2$)$_2$ | |
| 1.251 | 2,4-(CH$_3$)$_2$—C$_6$H$_3$—(CH$_2$)$_2$ | |
| 1.252 | 2,5-(CH$_3$)$_2$—C$_6$H$_3$—(CH$_2$)$_2$ | |
| 1.253 | 3,4-(CH$_3$)$_2$—C$_6$H$_3$—(CH$_2$)$_2$ | |
| 1.254 | 3,5-(CH$_3$)$_2$—C$_6$H$_3$—(CH$_2$)$_2$ | |
| 1.255 | 4,5-(CH$_3$)$_2$—C$_6$H$_3$—(CH$_2$)$_2$ | |
| 1.256 | 2,3,4-(CH$_3$)$_2$—C$_6$H$_2$—(CH$_2$)$_2$ | |
| 1.257 | 2,4,5-(CH$_3$)$_3$—C$_6$H$_2$—(CH$_2$)$_2$ | |
| 1.258 | 2,4,6-(CH$_3$)$_3$—C$_6$H$_2$—(CH$_2$)$_2$ | |
| 1.259 | 2,2,6-(CH$_3$)$_3$—C$_6$H$_2$—(CH$_2$)$_2$ | |
| 1.260 | 2-CF$_3$—C$_6$H$_4$—(CH$_2$)$_2$ | |
| 1.261 | 2-CF$_3$—C$_6$H$_4$—(CH$_2$)$_2$ | |
| 1.262 | 4-CF$_3$—C$_6$H$_4$—(CH$_2$)$_2$ | |
| 1.263 | 2-CH$_3$-3-CF$_3$—C$_6$H$_3$—(CH$_2$)$_2$ | |
| 1.264 | 2-CH$_3$-4-CF$_3$—C$_6$H$_3$—(CH$_2$)$_2$ | |
| 1.265 | 2-CF$_3$-3-CH$_3$—C$_6$H$_3$—(CH$_2$)$_2$ | |

TABLE I-continued

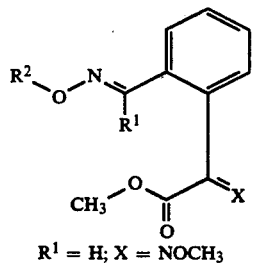

$R^1 = H; X = NOCH_3$

| Comp. no. | $R^2$ | IR (cm$^{-1}$) |
|---|---|---|
| 1.266 | 2-CF$_3$-4-CH$_3$—C$_6$H$_3$—(CH$_2$)$_2$ | |
| 1.267 | 2-CF$_3$-5-CH$_3$—C$_6$H$_3$—(CH$_2$)$_2$ | |
| 1.268 | 2-CH$_3$-5-CH$_3$—C$_6$H$_3$—(CH$_2$)$_2$ | |
| 1.269 | 2-Br—C$_6$H$_4$—(CH$_2$)$_2$ | |
| 1.270 | 3-Br—C$_6$H$_4$—(CH$_2$)$_2$ | |
| 1.271 | 4-Br—C$_6$H$_4$—(CH$_2$)$_2$ | |
| 1.272 | 2-(iso-Propyl)-C$_6$H$_4$—(CH$_2$)$_2$ | |
| 1.273 | 3-(iso-Propyl)-C$_6$H$_4$—(CH$_2$)$_2$ | |
| 1.274 | 4-(iso-Propyl)-C$_6$H$_4$—(CH$_2$)$_2$ | |
| 1.275 | 2-(iso-Propyl)-3-Cl—C$_6$H$_3$—(CH$_2$)$_2$ | |
| 1.276 | 2-(iso-Propyl)-4-Cl—C$_6$H$_3$—(CH$_2$)$_2$ | |
| 1.277 | 2-(iso-Propyl)-5-Cl—C$_6$H$_3$—(CH$_2$)$_2$ | |
| 1.278 | 2-CH$_3$-3-(iso-Propyl)-C$_6$H$_3$—(CH$_2$)$_2$ | |
| 1.279 | 2-CH$_3$-4-(iso-Propyl)-C$_6$H$_3$—(CH$_2$)$_2$ | |
| 1.280 | 2-CH$_3$-5-(iso-Propyl)-C$_6$H$_3$—(CH$_2$)$_2$ | |
| 1.281 | 2-t-C$_4$H$_9$—C$_6$H$_4$—(CH$_2$)$_2$ | |
| 1.282 | 3-t-C$_4$H$_9$—C$_6$H$_4$—(CH$_2$)$_2$ | |
| 1.283 | 4-t-C$_4$H$_9$—C$_6$H$_4$—(CH$_2$)$_2$ | |
| 1.284 | 2-CH$_3$-3-t-C$_4$H$_9$—C$_6$H$_3$—(CH$_2$)$_2$ | |
| 1.285 | 2-CH$_3$-4-t-C$_4$H$_9$—C$_6$H$_3$—(CH$_2$)$_2$ | |
| 1.286 | 2-CH$_3$-5-t-C$_4$H$_9$—C$_6$H$_3$—(CH$_2$)$_2$ | |
| 1.287 | 3-CH$_3$-4-t-C$_4$H$_9$—C$_6$H$_3$—(CH$_2$)$_2$ | |
| 1.288 | 3-CH$_3$-5-t-C$_4$H$_9$—C$_6$H$_3$—(CH$_2$)$_2$ | |
| 1.289 | 2-Cl-3-t-C$_4$H$_9$—C$_6$H$_3$—(CH$_2$)$_2$ | |
| 1.290 | 2-Cl-4-t-C$_4$H$_9$—C$_6$H$_3$—(CH$_2$)$_2$ | |
| 1.291 | 2-Cl-5-t-C$_4$H$_9$—C$_6$H$_3$—(CH$_2$)$_2$ | |
| 1.292 | 3-Cl-4-t-C$_4$H$_9$—C$_6$H$_3$—(CH$_2$)$_2$ | |
| 1.293 | 3-Cl-5-t-C$_4$H$_9$—C$_6$H$_3$—(CH$_2$)$_2$ | |
| 1.294 | 2-OCH$_3$—C$_6$H$_4$—(CH$_2$)$_2$ | |
| 1.295 | 3-OCH$_3$—C$_6$H$_4$—(CH$_2$)$_2$ | |
| 1.296 | 4-OCH$_3$—C$_6$H$_4$—(CH$_2$)$_2$ | |
| 1.297 | 2-CH$_3$-3-OCH$_3$—C$_6$H$_3$—(CH$_2$)$_2$ | |
| 1.298 | 2-CH$_3$-4-OCH$_3$—C$_6$H$_3$—(CH$_2$)$_2$ | |
| 1.299 | 2-CH$_3$-5-OCH$_3$—C$_6$H$_3$—(CH$_2$)$_2$ | |
| 1.300 | 3-CH$_3$-4-OCH$_3$—C$_6$H$_3$—(CH$_2$)$_2$ | |
| 1.301 | 3-CH$_3$-5-OCH$_3$—C$_6$H$_3$—(CH$_2$)$_2$ | |
| 1.302 | 2-Cl-3-OCH$_3$—C$_6$H$_3$—(CH$_2$)$_2$ | |
| 1.303 | 2-Cl-4-OCH$_3$—C$_6$H$_3$—(CH$_2$)$_2$ | |
| 1.304 | 2-Cl-5-OCH$_3$—C$_6$H$_3$—(CH$_2$)$_2$ | |
| 1.305 | 2-OCH$_3$-3-Cl—C$_6$H$_3$—(CH$_3$)$_2$ | |
| 1.306 | 2-OCH$_3$-4-Cl—C$_6$H$_3$—(CH$_3$)$_2$ | |
| 1.307 | 2-OCH$_3$-5-Cl—C$_6$H$_3$—(CH$_3$)$_2$ | |
| 1.308 | 2-CH$_3$-4-(Cyclohexyl)-C$_6$H$_3$—(CH$_2$)$_2$ | |
| 1.309 | 2-CH$_3$-4-C$_6$H$_5$—C$_6$H$_3$—(CH$_2$)$_2$ | |
| 1.310 | 2-CH$_3$-3-Br—C$_6$H$_3$—(CH$_2$)$_2$ | |
| 1.311 | 2-CH$_3$-4-Br—C$_6$H$_3$—(CH$_2$)$_2$ | |
| 1.312 | 2-CH$_3$-5-Br—C$_6$H$_3$—(CH$_2$)$_2$ | |
| 1.313 | 2-CH$_3$-3-(Methoxyiminomethyl)-C$_6$H$_3$—(CH$_2$)$_2$ | |
| 1.314 | 2-Methoxyiminomethyl-C$_6$H$_4$—(CH$_2$)$_2$ | |
| 1.315 | 3-Methoxyiminomethyl-C$_6$H$_4$—(CH$_2$)$_2$ | |
| 1.316 | 2-CH$_3$-4-(Methoxyiminomethyl)-C$_6$H$_3$—(CH$_2$)$_2$ | |
| 1.317 | 2-Phenyl-C$_6$H$_4$-(CH$_2$)$_2$ | |
| 1.318 | 3-Phenyl-C$_6$H$_4$-(CH$_2$)$_2$ | |
| 1.319 | 4-Phenyl-C$_6$H$_4$-(CH$_2$)$_2$ | |
| 1.320 | 2-Phenoxy-C$_6$H$_4$—(CH$_2$)$_2$ | |
| 1.321 | 3-Phenoxy-C$_6$H$_4$—(CH$_2$)$_2$ | |
| 1.322 | 4-Phenoxy-C$_6$H$_4$—(CH$_2$)$_2$ | |
| 1.323 | 2-Benzyloxy-C$_6$H$_4$—(CH$_2$)$_2$ | |
| 1.324 | 3-Benzyloxy-C$_6$H$_4$—(CH$_2$)$_2$ | |
| 1.325 | 4-Benzyloxy-C$_6$H$_4$—(CH$_2$)$_2$ | |
| 1.326 | 1-Naphthyl-(CH$_2$)$_2$ | 1727, 1497, 1217, 1070, 1045, 1020 |
| 1.327 | 2-Naphthyl-(CH$_2$)$_2$ | |
| 1.328 | 9-Anthryl-(CH$_2$)$_2$ | |
| 1.329 | 2-CH$_3$-3-C$_6$H$_5$O—C$_6$H$_3$—(CH$_2$)$_2$ | |
| 1.330 | 2-CH$_3$-4-C$_6$H$_5$O—C$_6$H$_3$—(CH$_2$)$_2$ | |
| 1.331 | 2-CH$_3$-5-C$_6$H$_5$O—C$_6$H$_3$—(CH$_2$)$_2$ | |
| 1.332 | 3-CH$_3$-4-C$_6$H$_5$O—C$_6$H$_3$—(CH$_2$)$_2$ | |

TABLE I-continued

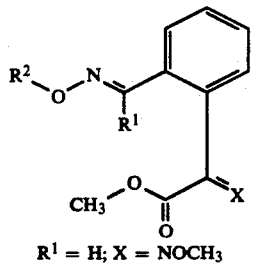

$R^1 = H; X = NOCH_3$

| Comp. no. | $R^2$ | IR (cm$^{-1}$) |
|---|---|---|
| 1.333 | 4-CH$_3$-5-C$_6$H$_5$O—C$_6$H$_3$—(CH$_2$)$_2$ | |
| 1.334 | 2-Cl-3-C$_6$H$_5$O—C$_6$H$_3$—(CH$_2$)$_2$ | |
| 1.335 | 2-Cl-4-C$_6$H$_5$O—C$_6$H$_3$—(CH$_2$)$_2$ | |
| 1.336 | 2-Cl-5-C$_6$H$_5$O—C$_6$H$_3$—(CH$_2$)$_2$ | |
| 1.337 | 3-Cl-4-C$_6$H$_5$O—C$_6$H$_3$—(CH$_2$)$_2$ | |
| 1.338 | 3-Cl-5-C$_6$H$_5$O—C$_6$H$_3$—(CH$_2$)$_2$ | |
| 1.339 | 2-CH$_3$-4-CO$_2$CH$_3$—C$_6$H$_3$—(CH$_2$)$_2$ | |
| 1.340 | 2-CH$_3$-5-CO$_2$CH$_3$—C$_6$H$_3$—(CH$_2$)$_2$ | |
| 1.341 | C$_6$H$_5$—CH=CH—CH$_2$ | 1725, 1214, 1071, 1025, 959 |
| 1.342 | 2-F—C$_6$H$_4$—CH=CH—CH$_2$ | |
| 1.343 | 2-F—C$_6$H$_4$—CH=CH—CH$_2$ | |
| 1.344 | 4-F—C$_6$H$_4$—CH=CH—CH$_2$ | |
| 1.345 | 2-Cl—C$_6$H$_4$—CH=CH—CH$_2$ | |
| 1.346 | 3-Cl—C$_6$H$_4$—CH=CH—CH$_2$ | |
| 1.347 | 4-Cl—C$_6$H$_4$—CH=CH—CH$_2$ | 1722, 1490, 1211, 1070, 1012, 933 |
| 1.348 | 2,3-Cl$_2$—C$_6$H$_4$—CH=CH—CH$_2$ | |
| 1.349 | 2,4-Cl$_2$—C$_6$H$_4$—CH=CH—CH$_2$ | |
| 1.350 | 2,5-Cl$_2$—C$_6$H$_4$—CH=CH—CH$_2$ | |
| 1.351 | 2,6-Cl$_2$—C$_6$H$_4$—CH=CH—CH$_2$ | |
| 1.352 | 3,4-Cl$_2$—C$_6$H$_4$—CH=CH—CH$_2$ | |
| 1.353 | 2-CH$_3$—C$_6$H$_4$—CH=CH—CH$_2$ | |
| 1.354 | 3-CH$_3$—C$_6$H$_4$—CH=CH—CH$_2$ | |
| 1.355 | 4-CH$_3$—C$_6$H$_4$—CH=CH—CH$_2$ | |
| 1.356 | 2,3-(CH$_3$)$_2$—C$_6$H$_3$—CH=CH—CH$_2$ | |
| 1.357 | 2,4-(CH$_3$)$_2$—C$_6$H$_3$—CH=CH—CH$_2$ | |
| 1.358 | 2,5-(CH$_3$)$_2$—C$_6$H$_3$—CH=CH—CH$_2$ | |
| 1.359 | 3,4-(CH$_3$)$_2$—C$_6$H$_3$—CH=CH—CH$_2$ | |
| 1.360 | 3,5-(CH$_3$)$_2$—C$_6$H$_3$—CH=CH—CH$_2$ | |
| 1.361 | 4,5-(CH$_3$)$_2$—C$_6$H$_3$—CH=CH—CH$_2$ | |
| 1.362 | 2,3,4-(CH$_3$)$_3$—C$_6$H$_3$—CH=CH—CH$_2$ | |
| 1.363 | 2,4,5-(CH$_3$)$_3$—C$_6$H$_3$—CH=CH—CH$_2$ | |
| 1.364 | 2,4,6-(CH$_3$)$_3$—C$_6$H$_3$—CH=CH—CH$_2$ | |
| 1.365 | 2,3,6-(CH$_3$)$_3$—C$_6$H$_3$—CH=CH—CH$_2$ | |
| 1.366 | 2-CF$_3$—C$_6$H$_4$—CH=CH—CH$_2$ | |
| 1.367 | 3-CF$_3$—C$_6$H$_4$—CH=CH—CH$_2$ | |
| 1.368 | 4-CF$_3$—C$_6$H$_4$—CH=CH—CH$_2$ | |
| 1.369 | 2-CH$_3$-3-CF$_3$—C$_6$H$_3$—CH=CH—CH$_2$ | |
| 1.370 | 2-CH$_3$-4-CF$_3$—C$_6$H$_3$—CH=CH—CH$_2$ | |
| 1.371 | 2-CF$_3$-3-CH$_3$—C$_6$H$_3$—CH=CH—CH$_2$ | |
| 1.372 | 2-CF$_3$-4-CH$_3$—C$_6$H$_3$—CH=CH—CH$_2$ | |
| 1.373 | 2-CF$_3$-5-CH$_3$—C$_6$H$_3$—CH=CH—CH$_2$ | |
| 1.374 | 2-CH$_3$-5-CF$_3$—C$_6$H$_3$—CH=CH—CH$_2$ | |
| 1.375 | C$_6$H$_5$—(CH$_2$)$_3$ | |
| 1.376 | C$_6$H$_5$—(CH$_2$)$_4$ | |
| 1.377 | C$_6$H$_5$—CH$_2$CH=CH—CH$_2$ | |
| 1.378 | 4-F—C$_6$H$_4$—CH=CH—(CH$_2$)$_2$ | |
| 1.379 | CH$_3$O—CO—CH$_2$ | 1760, 1737, 1438, 1217, 1097, 1069, 1020 |
| 1.380 | CH$_3$CH$_2$O—CO—CH$_2$ | |
| 1.381 | CH$_3$—CO—CH$_2$—CH$_2$ | |
| 1.382 | t-C$_4$H$_9$O—CO—(CH$_2$)$_3$ | |
| 1.383 | t-C$_4$H$_9$O—CO—(CH$_2$)$_2$ | |
| 1.384 | t-C$_4$H$_9$O—CO—CH$_2$ | 1749, 1729, 1226, 1159, 1069, 1020 |
| 1.385 | n-C$_4$H$_9$O—CO—CH$_2$ | |
| 1.386 | iso-C$_4$H$_9$O—CO—CH$_2$ | |
| 1.387 | n-C$_3$H$_7$O—CO—CH$_2$ | |
| 1.388 | sec.-C$_4$H$_9$O—CO—CH$_2$ | |
| 1.389 | C$_6$H$_5$—CO—CH$_2$ | |
| 1.390 | 2-CH$_3$—C$_6$H$_4$O—CO—CH$_2$ | |
| 1.391 | 3-CH$_3$—C$_6$H$_4$O—CO—CH$_2$ | |
| 1.392 | 4-CH$_3$—C$_6$H$_4$O—CO—CH$_2$ | |
| 1.393 | 2-Cl—C$_6$H$_4$O—CO—CH$_2$ | |
| 1.394 | 3-Cl—C$_6$H$_4$O—CO—CH$_2$ | |
| 1.395 | 4-Cl—C$_6$H$_4$O—CO—CH$_2$ | |
| 1.396 | C$_6$H$_5$—C(CH$_3$)=CH—CH$_2$ | 1728, 1444, 1323, 1218, 1071, 1019 |

TABLE I-continued
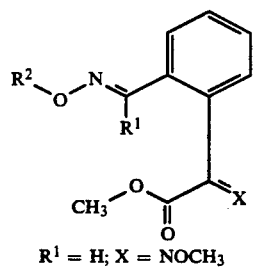
$R^1 = H; X = NOCH_3$
| Comp. no. | $R^2$ | IR (cm$^{-1}$) |
|---|---|---|
| 1.397 | 2-pyridyl-CH$_2$ | |
| 1.398 | (3-Cl-2-pyridyl)-CH$_2$ | |
| 1.399 | (4-Cl-2-pyridyl)-CH$_2$ | |
| 1.400 | (3-CH$_3$-2-pyridyl)-CH$_2$ | |
| 1.401 | (4-CH$_3$-2-pyridyl)-CH$_2$ | |
| 1.402 | (3-CF$_3$-2-pyridyl)-CH$_2$ | |
| 1.403 | (3-Br-2-pyridyl)-CH$_2$ | |
| 1.404 | (4-Br-2-pyridyl)-CH$_2$ | |
| 1.405 | (3-F-2-pyridyl)-CH$_2$ | |
| 1.406 | 3-pyridyl-CH$_2$ | |

TABLE I-continued
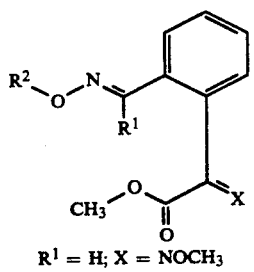
$R^1 = H; X = NOCH_3$
| Comp. no. | R² | IR (cm⁻¹) |
|---|---|---|
| 1.407 | 3-methyl-2-chloropyridin-yl-CH₂ | |
| 1.408 | pyrazin-2-yl-CH₂ | |
| 1.409 | quinoxalin-2-yl-CH₂ | |
| 1.410 | pyridazin-3-yl-CH₂ | |
| 1.411 | 4-chloro-3-methylpyridin-2-yl-CH₂ | |
| 1.412 | 3-chloro-4-methylpyridin-2-yl-CH₂ | |
| 1.413 | 3-bromo-4-methylpyridin-2-yl-CH₂ | |
| 1.414 | 3-chloro-6-methylpyridin-2-yl-CH₂ | |
| 1.415 | 3-bromo-6-methylpyridin-2-yl-CH₂ | |
| 1.416 | 3,6-dimethylpyridin-2-yl-CH₂ | |

TABLE I-continued
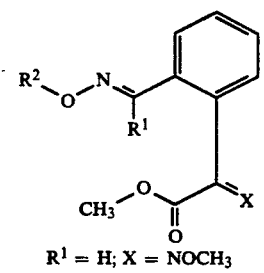
$R^1 = H; X = NOCH_3$
| Comp. no. | $R^2$ | IR (cm$^{-1}$) |
|---|---|---|
| 1.417 | 4-CH₃, 6-CH₃-pyridin-2-yl-CH₂ | |
| 1.418 | 4-CF₃, 3-Cl-pyridin-2-yl-CH₂ | |
| 1.419 | 3-Cl, 6-Cl-pyridin-2-yl-CH₂ | |
| 1.420 | 4-Cl, 3-Cl-pyridin-2-yl-CH₂ | |
| 1.421 | 3-Cl, 2-CH₃-pyridin-6-yl-CH₂ | |
| 1.422 | 4-OCH₃, 3-Cl-pyridin-2-yl-CH₂ | |
| 1.423 | 3-F, 6-Cl-pyridin-2-yl-CH₂ | |
| 1.424 | 4-Br, 6-O₂N-pyridin-2-yl-CH₂ | |
| 1.425 | furan-2-yl-CH₂ | |
| 1.426 | furan-3-yl-CH₂ | |

TABLE I-continued
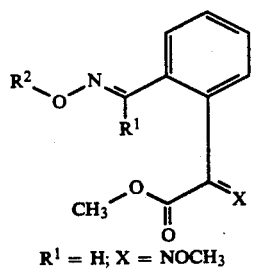
$R^1 = H; X = NOCH_3$
| Comp. no. | R² | IR (cm⁻¹) |
|---|---|---|
| 1.427 | 3-chloro-5-(CH₂–)-furan | |
| 1.428 | 2-(CH₂–)-pyrrole | |
| 1.429 | 3-(CH₂–)-pyrrole | |
| 1.430 | 1-methyl-2-(CH₂–)-pyrrole | |
| 1.431 | 1-methyl-3-(CH₂–)-pyrrole | |
| 1.432 | 2-(CH₂–)-benzofuran | |
| 1.433 | 2-(CH₂–)-benzothiophene | |
| 1.434 | 3-(CH₂–)-pyrazole | |
| 1.435 | 5-(CH₂–)-isoxazole | |
| 1.436 | 4-chloro-5-(CH₂–)-isoxazole | |
| 1.437 | 3-chloro-5-(CH₂–)-isoxazole | |

TABLE I-continued
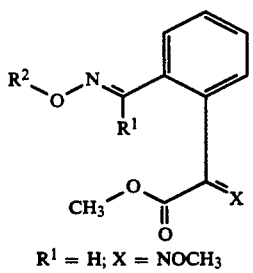
$R^1 = H; X = NOCH_3$
| Comp. no. | $R^2$ | IR (cm$^{-1}$) |
|---|---|---|
| 1.438 | 4-methyl-5-methylene-isoxazol-3-yl | |
| 1.439 | 3-methyl-5-methylene-isoxazol-5-yl | |
| 1.440 | 4-chloro-3-methyl-5-methylene-isoxazol-5-yl | |
| 1.441 | 3-chloro-4-methyl-5-methylene-isoxazol-5-yl | |
| 1.442 | thien-2-ylmethyl | |
| 1.443 | thien-3-ylmethyl | |
| 1.444 | 3-chlorothien-2-ylmethyl | |
| 1.445 | 4-chlorothien-2-ylmethyl | |
| 1.446 | indol-2-ylmethyl | |
| 1.447 | isothiazol-3-ylmethyl | |
| 1.448 | 4-chloroisothiazol-3-ylmethyl | |

TABLE I-continued
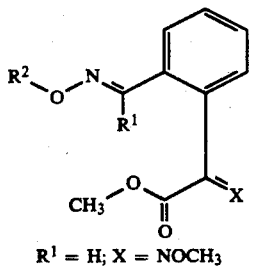
$R^1 = H; X = NOCH_3$
| Comp. no. | R² | IR (cm⁻¹) |
|---|---|---|
| 1.449 | 3-chloroisothiazol-5-ylmethyl | |
| 1.450 | 2-(benzoyl)oxazol-4-ylmethyl (phenyl variant) | |
| 1.451 | 2-(2-methylbenzoyl)oxazol-4-ylmethyl | |
| 1.452 | 5-chlorothiophen-2-ylmethyl | |
| 1.453 | 2-(3-methylbenzoyl)oxazol-4-ylmethyl | |
| 1.454 | 2-(4-methylbenzoyl)oxazol-4-ylmethyl | |
| 1.455 | 2-(2-fluorobenzoyl)oxazol-4-ylmethyl | |
| 1.456 | 2-(2-methyl-4-fluorobenzoyl)oxazol-4-ylmethyl | |
| 1.457 | 2-(2-methyl-4-chlorobenzoyl)oxazol-2-yl | |

TABLE I-continued
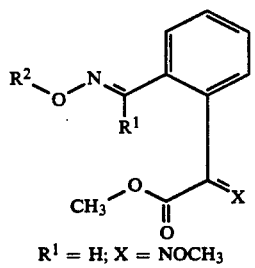
$R^1 = H; X = NOCH_3$
| Comp. no. | $R^2$ | IR (cm$^{-1}$) |
|---|---|---|
| 1.458 | (4-F-C6H4-C(=O)-N=C(CH2)-) | 1728, 1610, 1499, 1223, 1069, 1019 |
| 1.459 | (5-CH3-2-Cl-C6H3-C(=O)-N=C(CH2)-) | |
| 1.460 | (2-CH3-4-iPr-C6H3-C(=O)-N=C(CH2)-) | |
| 1.461 | (2,4-(CH3)2-C6H3-C(=O)-N=C(CH2)-) | |
| 1.462 | N≡C—CH$_2$ | 1728, 1439, 1324, 1310, 1218, 1067, 1017, 960, 768 |
| 1.463 | t-BuO—CH$_2$—CH=CH—CH$_2$ | 1743, 1728, 1221, 1197, 1070, 1044, 1020 |
| 1.464 | (CH$_3$)$_2$—C=CH—CH$_2$—CH$_2$—C(CH$_3$)=CH—CH$_2$ | 1744, 1729, 1438, 1221, 1212, 1071, 1019 |
| 1.465 | (CH$_3$)$_2$CH—C=CH—CH$_2$—CH$_2$—C(CH$_3$)=CH—CH$_2$ | 1744, 1729, 1438, 1221, 1212, 1071, 1019 |
TABLE II
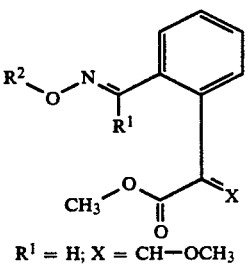
$R^1 = H; X = CH—OCH_3$
| Comp. no. | $R^2$ | IR (cm$^{-1}$) |
|---|---|---|
| 2.1 | H | |
| 2.2 | CH$_3$ | |
| 2.3 | CH$_3$CH$_2$ | |

-continued

| | |
|---|---|
| 2.4 | CH₃CH₂CH₂ |
| 2.5 | CH₂=CH—CH₂ |
| 2.6 | CH₃—CH≡CH |
| 2.7 | CH₃—CH(CH₃) |
| 2.8 | HC≡C—C(CH₃)=CHCH" |
| 2.9 | HC≡C—CH₂ |
| 2.10 | CH₃—O—CH₂—CH₂ |
| 2.11 | C₂H₅—O—CH₂—CH₂ |
| 2.12 | Cl—CH₂—CH₂ |
| 2.13 | Cyclo-C₃H₅—CH₂ |
| 2.14 | CH₃—CH=CH—CH₂ |
| 2.15 | CH₂=CH—CH₂—CH₂ |
| 2.16 | CH₃—C≡C—CH₂ |
| 2.17 | CH₃CH₂—C≡C—CH₂ |
| 2.18 | CH₃—(CH₂)₃ |
| 2.19 | CH₃—(CH₂)₄ |
| 2.20 | (CH₃)₃C |
| 2.21 | Cyclo-C₆H₁₁ |
| 2.22 | 2-CH₃-Cyclo-C₆H₁₀ |
| 2.23 | C₆H₅—CH₂ |
| 2.24 | 2-F—C₆H₄—CH₂ |
| 2.25 | 3-F—C₆H₄—CH₂ |
| 2.26 | 4-F—C₆H₄—CH₂ |
| 2.27 | 2-Cl—C₆H₄—CH₂ |
| 2.28 | 3-Cl—C₆H₄—CH₂ |
| 2.29 | 4-Cl—C₆H₄—CH₂ |
| 2.30 | 2,3-Cl₂—C₆H₃—CH₂ |
| 2.31 | 2,4-Cl₂—C₆H₃—CH₂ |
| 2.32 | 2,5-Cl₂—C₆H₃—CH₂ |
| 2.33 | 2,6-Cl₂—C₆H₃—CH₂ |
| 2.34 | 3,4-Cl₂—C₆H₃—CH₂ |
| 2.35 | 2-CH₃—C₆H₄—CH₂ |
| 2.36 | 3-CH₃—C₆H₄—CH₂ |
| 2.37 | 4-CH₃—C₆H₄—CH₂ |
| 2.38 | 2,3-(CH₃)₂—C₆H₃—CH₂ |
| 2.39 | 2,4-(CH₃)₂—C₆H₃—CH₂ |
| 2.40 | 2,5-(CH₃)₂—C₆H₃—CH₂ |
| 2.41 | 3,4-(CH₃)₂—C₆H₃—CH₂ |
| 2.42 | 3,5-(CH₃)₂—C₆H₃—CH₂ |
| 2.43 | 4,5-(CH₃)₂—C₆H₃—CH₂ |
| 2.44 | 2,3,4-(CH₃)₃—C₆H₂—CH₂ |
| 2.45 | 2,4,5-(CH₃)₃—C₆H₂—CH₂ |
| 2.46 | 2,4,6-(CH₃)₃—C₆H₂—CH₂ |
| 2.47 | 2,3,6-(CH₃)₃—C₆H₂—CH₂ |
| 2.48 | 2-CF₃—C₆H₄—CH₂ |
| 2.49 | 3-CF₃—C₆H₄—CH₂ |
| 2.50 | 4-CF₃—C₆H₄—CH₂ |
| 2.51 | 2-CH₃-3-CF₃—C₆H₃—CH₂ |
| 2.52 | 2-CH₃-4-CF₃—C₆H₃—CH₂ |
| 2.53 | 2-CF₃-3-CH₃—C₆H₃—CH₃ |
| 2.54 | 2-CF₃-4-CH₃—C₆H₃—CH₂ |
| 2.55 | 2-CF₃-5-CH₃—C₆H₃—CH₂ |
| 2.56 | 2-CH₃-5-CF₃—C₆H₃—CH₂ |
| 2.57 | 2-Br—C₆H₄—CH₂ |
| 2.58 | 3-Br—C₆H₄—CH₂ |
| 2.59 | 4-Br—C₆H₄—CH₂ |
| 2.60 | 2-(iso-Propyl)-C₆H₄—CH₂ |
| 2.61 | 3-(iso-Propyl)-C₆H₄—CH₂ |
| 2.62 | 4-(iso-Propyl)-C₆H₄—CH₂ |
| 2.63 | 2-(iso-Propyl)-3-Cl—C₆H₃—CH₂ |
| 2.64 | 2-(iso-Propyl)-4-Cl—C₆H₃—CH₂ |
| 2.65 | 2-(iso-Propyl)-5-Cl—C₆H₃—CH₂ |
| 2.66 | 2-CH₃-3-(iso-Propyl)-C₆H₃—CH₂ |
| 2.67 | 2-CH₃-4-(iso-Propyl)-C₆H₃—CH₂ |
| 2.68 | 2-CH₃-5-(iso-Propyl)-C₆H₃—CH₂ |
| 2.69 | 2-t-C₄H₉—C₆H₄—CH₂ |
| 2.70 | 3-t-C₄H₉—C₆H₄—CH₂ |
| 2.71 | 4-t-C₄H₉—C₆H₄—CH₂ |
| 2.72 | 2-CH₃-3-t-C₄H₉—C₆H₃—CH₂ |
| 2.73 | 2-CH₃-4-t-C₄H₉—C₆H₃—CH₂ |
| 2.74 | 2-CH₃-5-t-C₄H₉—C₆H₃—CH₂ |
| 2.75 | 3-CH₃-4-t-C₄H₉—C₆H₃—CH₂ |
| 2.76 | 3-CH₃-5-t-C₄H₉—C₆H₃—CH₂ |
| 2.77 | 2-Cl-3-t-C₄H₉—C₆H₃—CH₂ |
| 2.78 | 2-Cl-4-t-C₄H₉—C₆H₃—CH₂ |
| 2.79 | 2-Cl-5-t-C₄H₉—C₆H₃—CH₂ |
| 2.80 | 3-Cl-4-t-C₄H₉—C₆H₃—CH₂ |
| 2.81 | 3-Cl-5-t-C₄H₉—C₆H₃—CH₂ |
| 2.82 | 2-OCH₃—C₆H₄—CH₂ |
| 2.83 | 3-OCH₃—C₆H₄—CH₂ |
| 2.84 | 4-OCH₃—C₆H₄—CH₂ |
| 2.85 | 2-CH₃-3-OCH₃—C₆H₃—CH₂ |
| 2.86 | 2-CH₃-4-OCH₃—C₆H₃—CH₂ |

-continued

| | |
|---|---|
| 2.87 | 2-CH$_3$-5-OCH$_3$—C$_6$H$_3$—CH$_2$ |
| 2.88 | 3-CH$_3$-4-OCH$_3$—C$_6$H$_3$—CH$_2$ |
| 2.89 | 3-CH$_3$-5-OCH$_3$—C$_6$H$_3$—CH$_3$ |
| 2.90 | 2-Cl-3-OCH$_3$—C$_6$H$_3$—CH$_2$ |
| 2.91 | 2-Cl-4-OCH$_3$—C$_6$H$_3$—CH$_2$ |
| 2.92 | 2-Cl-5-OCH$_3$—C$_6$H$_3$—CH$_2$ |
| 2.93 | 2-OCH$_3$-3-Cl—C$_6$H$_3$—CH$_2$ |
| 2.94 | 2-OCH$_3$-4-Cl—C$_6$H$_3$—CH$_2$ |
| 2.95 | 2-OCH$_3$-5-Cl—C$_6$H$_3$—CH$_2$ |
| 2.96 | 2-CH$_3$-4-(Cyclohexyl)-C$_6$H$_3$—CH$_2$ |
| 2.97 | 2-CH$_3$-4-C$_6$H$_5$—C$_6$H$_3$—CH$_2$ |
| 2.98 | 2-CH$_3$-3-Br—C$_6$H$_3$—CH$_2$ |
| 2.99 | 2-CH$_3$-4-Br—C$_6$H$_3$—CH$_2$ |
| 2.100 | 2-CH$_3$-5-Br—C$_6$H$_3$—CH$_2$ |
| 2.101 | 2-CH$_2$-3-(Methoxyiminomethyl)-C$_6$H$_3$—CH$_2$ |
| 2.102 | 2-Methoxyiminomethyl-C$_6$H$_4$—CH$_4$ |
| 2.103 | 3-Methoxyiminomethyl-C$_6$H$_4$—CH$_4$ |
| 2.104 | 2-CH$_3$-4-(Methoxyiminomethyl)-C$_6$H$_3$—CH$_2$ |
| 2.105 | 2-Phenyl-C$_6$H$_4$—CH$_2$ |
| 2.106 | 3-Phenyl-C$_6$H$_4$—CH$_2$ |
| 2.107 | 4-Phenyl-C$_6$H$_4$—CH$_2$ |
| 2.108 | 2-Phenoxy-C$_6$H$_4$—CH$_2$ |
| 2.109 | 3-Phenoxy-C$_6$H$_4$—CH$_2$ |
| 2.110 | 4-Phenoxy-C$_6$H$_4$—CH$_2$ |
| 2.111 | 2-Benzyloxy-C$_6$H$_4$—CH$_2$ |
| 2.112 | 3-Benzyloxy-C$_6$H$_4$—CH$_2$ |
| 2.113 | 4-Benzyloxy-C$_6$H$_4$—CH$_2$ |
| 2.114 | 1-Naphthyl-CH$_2$ |
| 2.115 | 2-Naphthyl-CH$_2$ |
| 2.116 | 9-Anthryl-CH$_2$ |
| 2.117 | 2-CH$_3$-3-C$_6$H$_5$O—C$_6$H$_3$—CH$_2$ |
| 2.118 | 2-CH$_3$-4-C$_6$H$_5$O—C$_6$H$_3$—CH$_2$ |
| 2.119 | 2-CH$_3$-5-C$_6$H$_5$O—C$_6$H$_3$—CH$_2$ |
| 2.120 | 3-CH$_3$-4-C$_6$H$_5$O—C$_6$H$_3$—CH$_2$ |
| 2.121 | 4-CH$_3$-5-C$_6$H$_5$O—C$_6$H$_3$—CH$_2$ |
| 2.122 | 2-Cl-3-C$_6$H$_5$O—C$_6$H$_3$—CH$_2$ |
| 2.123 | 2-Cl-4-C$_6$H$_5$O—C$_6$H$_3$—CH$_2$ |
| 2.124 | 2-Cl-5-C$_6$H$_5$O—C$_6$H$_3$—CH$_2$ |
| 2.125 | 3-Cl-4-C$_6$H$_5$O—C$_6$H$_3$—CH$_2$ |
| 2.126 | 3-Cl-5-C$_6$H$_5$O—C$_6$H$_3$—CH$_2$ |
| 2.127 | 2-CH$_3$-4-CO$_2$CH$_3$—C$_6$H$_3$—CH$_2$ |
| 2.128 | 2-CH$_3$-5-CO$_2$CH$_3$—C$_6$H$_3$—CH$_2$ |
| 2.129 | C$_6$H$_4$—CH(CH$_3$) |
| 2.130 | 2-F—C$_6$H$_4$—CH(CH$_3$) |
| 2.131 | 2-F—C$_6$H$_4$—CH(CH$_3$) |
| 2.132 | 4-F—C$_6$H$_4$—CH(CH$_3$) |
| 2.133 | 2-Cl—C$_6$H$_4$—CH(CH$_3$) |
| 2.134 | 3-Cl—C$_6$H$_4$—CH(CH$_3$) |
| 2.135 | 4-Cl—C$_6$H$_4$—CH(CH$_3$) |
| 2.136 | 2,3-Cl$_2$—C$_6$H$_3$—CH(CH$_3$) |
| 2.137 | 2,4-Cl$_2$—C$_6$H$_3$—CH(CH$_3$) |
| 2.138 | 2,5-Cl$_2$—C$_6$H$_3$—CH(CH$_3$) |
| 2.139 | 2,6-Cl$_2$—C$_6$H$_3$—CH(CH$_3$) |
| 2.140 | 3,4-Cl$_2$—C$_6$H$_3$—CH(CH$_3$) |
| 2.141 | 2-CH$_3$—C$_6$H$_4$—CH(CH$_3$) |
| 2.142 | 3-CH$_3$—C$_6$H$_4$—CH(CH$_3$) |
| 2.143 | 4-CH$_3$—C$_6$H$_4$—CH(CH$_3$) |
| 2.144 | 2,3-(CH$_3$)$_2$—C$_6$H$_3$—CH(CH$_3$) |
| 2.145 | 2,4-(CH$_3$)$_2$—C$_6$H$_3$—CH(CH$_3$) |
| 2.146 | 2,5-(CH$_3$)$_2$—C$_6$H$_3$—CH(CH$_3$) |
| 2.147 | 3,4-(CH$_3$)$_2$—C$_6$H$_3$—CH(CH$_3$) |
| 2.148 | 3,5-(CH$_3$)$_2$—C$_6$H$_3$—CH(CH$_3$) |
| 2.149 | 4,5-(CH$_3$)$_2$—C$_6$H$_3$—CH(CH$_3$) |
| 2.150 | 2,3,4-(CH$_3$)$_2$—C$_6$H$_3$—CH(CH$_3$) |
| 2.151 | 2,4,5-(CH$_3$)$_2$—C$_6$H$_3$—CH(CH$_3$) |
| 2.152 | 2,4,6-(CH$_3$)$_2$—C$_6$H$_3$—CH(CH$_3$) |
| 2.153 | 2,2,6-(CH$_3$)$_2$—C$_6$H$_3$—CH(CH$_3$) |
| 2.154 | 2-CF$_3$—C$_6$H$_4$—CH(CH$_3$) |
| 2.155 | 2-CF$_3$—C$_6$H$_4$—CH(CH$_3$) |
| 2.156 | 4-CF$_3$—C$_6$H$_4$—CH(CH$_3$) |
| 2.157 | 2-CH$_3$-3-CF$_3$—C$_6$H$_3$—CH(CH$_3$) |
| 2.158 | 2-CH$_3$-4-CF$_3$—C$_6$H$_3$—CH(CH$_3$) |
| 2.159 | 2-CF$_3$-3-CH$_3$—C$_6$H$_3$—CH(CH$_3$) |
| 2.160 | 2-CF$_3$-4-CH$_3$—C$_6$H$_3$—CH(CH$_3$) |
| 2.161 | 2-CF$_3$-5-CH$_3$—C$_6$H$_3$—CH(CH$_3$) |
| 2.162 | 2-CH$_3$-5-CF$_3$—C$_6$H$_3$—CH(CH$_3$) |
| 2.163 | 2-Br—C$_6$H$_4$—CH(CH$_3$) |
| 2.164 | 3-Br—C$_6$H$_4$—CH(CH$_3$) |
| 2.165 | 4-Br—C$_6$H$_4$—CH(CH$_3$) |
| 2.166 | 2-(iso-Propyl)-C$_6$H$_4$—CH(CH$_3$) |
| 2.167 | 3-(iso-Propyl)-C$_6$H$_4$—CH(CH$_3$) |
| 2.168 | 4-(iso-Propyl)-C$_6$H$_4$—CH(CH$_3$) |
| 2.169 | 2-(iso-Propyl)-C$_6$H$_3$—CH(CH$_3$) |

-continued

| | |
|---|---|
| 2.170 | 2-(iso-Propyl)-C$_6$H$_3$—CH(CH$_3$) |
| 2.171 | 2-(iso-Propyl)-C$_6$H$_3$—CH(CH$_3$) |
| 2.172 | 2-CH$_3$-3-(iso-Propyl)-C$_6$H$_3$—CH(CH$_3$) |
| 2.173 | 2-CH$_3$-4-(iso-Propyl)-C$_6$H$_3$—CH(CH$_3$) |
| 2.174 | 2-CH$_3$-5-(iso-Propyl)-C$_6$H$_3$—CH(CH$_3$) |
| 2.175 | 2-t-C$_4$H$_9$—C$_6$H$_4$—CH(CH$_3$) |
| 2.176 | 3-t-C$_4$H$_9$—C$_6$H$_4$—CH(CH$_3$) |
| 2.177 | 4-t-C$_4$H$_9$—C$_6$H$_4$—CH(CH$_3$) |
| 2.178 | 2-CH$_3$-3-t-C$_4$H$_9$—C$_6$H$_3$—CH(CH$_3$) |
| 2.179 | 2-CH$_3$-4-t-C$_4$H$_9$—C$_6$H$_3$—CH(CH$_3$) |
| 2.180 | 2-CH$_3$-5-t-C$_4$H$_9$—C$_6$H$_3$—CH(CH$_3$) |
| 2.181 | 3-CH$_3$-4-t-C$_4$H$_9$—C$_6$H$_3$—CH(CH$_3$) |
| 2.182 | 3-CH$_3$-5-t-C$_4$H$_9$—C$_6$H$_3$—CH(CH$_3$) |
| 2.183 | 2-Cl-3-t-C$_4$H$_9$—C$_6$H$_3$—CH(CH$_3$) |
| 2.184 | 2-Cl-4-t-C$_4$H$_9$—C$_6$H$_3$—CH(CH$_3$) |
| 2.185 | 2-Cl-5-t-C$_4$H$_9$—C$_6$H$_3$—CH(CH$_3$) |
| 2.186 | 3-Cl-4-t-C$_4$H$_9$—C$_6$H$_3$—CH(CH$_3$) |
| 2.187 | 3-Cl-5-t-C$_4$H$_9$—C$_6$H$_3$—CH(CH$_3$) |
| 2.188 | 2-OCH$_3$—C$_6$H$_4$—CH$_2$—CH(CH$_3$) |
| 2.189 | 3-OCH$_3$—C$_6$H$_4$—CH$_2$—CH(CH$_3$) |
| 2.190 | 4-OCH$_3$—C$_6$H$_4$—CH$_2$—CH(CH$_3$) |
| 2.191 | 2-CH$_3$-3-OCH$_3$—C$_6$H$_3$—CH(CH$_3$) |
| 2.192 | 2-CH$_3$-4-OCH$_3$—C$_6$H$_3$—CH(CH$_3$) |
| 2.193 | 2-CH$_3$-5-OCH$_3$—C$_6$H$_3$—CH(CH$_3$) |
| 2.194 | 3-CH$_3$-5-OCH$_3$—C$_6$H$_3$—CH(CH$_3$) |
| 2.195 | 3-CH$_3$-5-OCH$_3$—C$_6$H$_3$—CH(CH$_3$) |
| 2.196 | 2-Cl-3-OCH$_3$—C$_6$H$_3$—CH(CH$_3$) |
| 2.197 | 2-Cl-4-OCH$_3$—C$_6$H$_3$—CH(CH$_3$) |
| 2.198 | 2-Cl-5-OCH$_3$—C$_6$H$_3$—CH(CH$_3$) |
| 2.199 | 2-OCH$_3$-3-Cl—C$_6$H$_3$—CH(CH$_3$) |
| 2.200 | 2-OCH$_3$-4-Cl—C$_6$H$_3$—CH(CH$_3$) |
| 2.201 | 2-OCH$_3$-5-Cl—C$_6$H$_3$—CH(CH$_3$) |
| 2.202 | 2-CH$_3$-4-(Cyclohexyl)-C$_6$H$_3$—CH(CH$_3$) |
| 2.203 | 2-CH$_3$-4-C$_6$H$_5$—C$_6$H$_3$—CH(CH$_3$) |
| 2.204 | 2-CH$_3$-3-Br—C$_6$H$_3$—CH(CH$_3$) |
| 2.205 | 2-CH$_3$-4-Br—C$_6$H$_3$—CH(CH$_3$) |
| 2.206 | 3-CH$_3$-5-Br—C$_6$H$_3$—CH(CH$_3$) |
| 2.207 | 2-CH$_3$-3-(Methoxyiminomethyl)-C$_6$H$_3$—CH(CH$_3$) |
| 2.208 | 2-Methoxyiminomethyl-C$_6$H$_4$—CH(CH$_3$) |
| 2.209 | 3-Methoxyiminomethyl-C$_6$H$_4$—CH(CH$_3$) |
| 2.210 | 2-CH$_3$-4-(Methoxyiminomethyl)-C$_6$H$_3$—CH(CH$_3$) |
| 2.211 | 2-Phenyl-C$_6$H$_4$—CH(CH$_3$) |
| 2.212 | 3-Phenyl-C$_6$H$_4$—CH(CH$_3$) |
| 2.213 | 4-Phenyl-C$_6$H$_4$—CH(CH$_3$) |
| 2.214 | 2-Phenoxy-C$_6$H$_4$—CH(CH$_3$) |
| 2.215 | 3-Phenoxy-C$_6$H$_4$—CH(CH$_3$) |
| 2.216 | 4-Phenoxy-C$_6$H$_4$—CH(CH$_3$) |
| 2.217 | 2-Benzyloxy-C$_6$H$_4$—CH(CH$_3$) |
| 2.218 | 3-Benzyloxy-C$_6$H$_4$—CH(CH$_3$) |
| 2.219 | 4-Benzyloxy-C$_6$H$_4$—CH(CH$_3$) |
| 2.220 | 1-Naphthyl-CH(CH$_3$) |
| 2.221 | 2-Naphthyl-CH(CH$_3$) |
| 2.222 | 9-Anthryl-CH(CH$_3$) |
| 2.223 | 2-CH$_3$-3-C$_6$H$_5$O—C$_6$H$_3$—CH(CH$_3$) |
| 2.224 | 2-CH$_3$-4-C$_6$H$_5$O—C$_6$H$_3$—CH(CH$_3$) |
| 2.225 | 2-CH$_3$-5-C$_6$H$_5$O—C$_6$H$_3$—CH(CH$_3$) |
| 2.226 | 3-CH$_3$-4-C$_6$H$_5$O—C$_6$H$_3$—CH(CH$_3$) |
| 2.227 | 4-CH$_3$-5-C$_6$H$_5$O—C$_6$H$_3$—CH(CH$_3$) |
| 2.228 | 2-Cl-3-C$_6$H$_5$O—C$_6$H$_3$—CH(CH$_3$) |
| 2.229 | 2-Cl-4-C$_6$H$_5$O—C$_6$H$_3$—CH(CH$_3$) |
| 2.230 | 2-Cl-5-C$_6$H$_5$O—C$_6$H$_3$—CH(CH$_3$) |
| 2.231 | 3-Cl-4-C$_6$H$_5$O—C$_6$H$_3$—CH(CH$_3$) |
| 2.232 | 3-Cl-5-C$_6$H$_5$O—C$_6$H$_3$—CH(CH$_3$) |
| 2.233 | 2-CH$_3$-4-CO$_2$CH$_3$—C$_6$H$_3$—CH(CH$_3$) |
| 2.234 | 2-CH$_3$-5-CO$_2$CH$_3$—C$_6$H$_3$—CH(CH$_3$) |
| 2.235 | C$_6$H$_5$—(CH$_2$)$_2$ |
| 2.236 | 2-F—C$_6$H$_4$—(CH$_2$)$_2$ |
| 2.237 | 2-F—C$_6$H$_4$—(CH$_2$)$_2$ |
| 2.238 | 4-F—C$_6$H$_4$—(CH$_2$)$_2$ |
| 2.239 | 2-Cl—C$_6$H$_4$—(CH$_2$)$_2$ |
| 2.240 | 3-Cl—C$_6$H$_4$—(CH$_2$)$_2$ |
| 2.241 | 4-Cl—C$_6$H$_4$—(CH$_2$)$_2$ |
| 2.242 | 2,3-Cl$_2$—C$_6$H$_3$—(CH$_2$)$_2$ |
| 2.243 | 2,4-Cl$_2$—C$_6$H$_3$—(CH$_2$)$_2$ |
| 2.244 | 2,5-Cl$_2$—C$_6$H$_3$—(CH$_2$)$_2$ |
| 2.245 | 2,6-Cl$_2$—C$_6$H$_3$—(CH$_2$)$_2$ |
| 2.246 | 3,4-Cl$_2$—C$_6$H$_3$—(CH$_2$)$_2$ |
| 2.247 | 2-CH$_3$—C$_6$H$_4$—(CH$_2$)$_2$ |
| 2.248 | 3-CH$_3$—C$_6$H$_4$—(CH$_2$)$_2$ |
| 2.249 | 4-CH$_3$—C$_6$H$_4$—(CH$_2$)$_2$ |
| 2.250 | 2,3-(CH$_3$)$_2$—C$_6$H$_3$—(CH$_2$)$_2$ |
| 2.251 | 2,4-(CH$_3$)$_2$—C$_6$H$_3$—(CH$_2$)$_2$ |
| 2.252 | 2,5-(CH$_3$)$_2$—C$_6$H$_3$—(CH$_2$)$_2$ |

-continued

| | |
|---|---|
| 2.253 | 3,4-(CH$_3$)$_2$—C$_6$H$_3$—(CH$_2$)$_2$ |
| 2.254 | 3,5-(CH$_3$)$_2$—C$_6$H$_3$—(CH$_2$)$_2$ |
| 2.255 | 4,5-(CH$_3$)$_2$—C$_6$H$_3$—(CH$_2$)$_2$ |
| 2.256 | 2,3,4-(CH$_3$)$_3$—C$_6$H$_2$—(CH$_2$)$_2$ |
| 2.257 | 2,4,5-(CH$_3$)$_3$—C$_6$H$_2$—(CH$_2$)$_2$ |
| 2.258 | 2,4,6-(CH$_3$)$_3$—C$_6$H$_2$—(CH$_2$)$_2$ |
| 2.259 | 2,2,6-(CH$_3$)$_3$—C$_6$H$_2$—(CH$_2$)$_2$ |
| 2.260 | 2-CF$_3$—C$_6$H$_4$—(CH$_2$)$_2$ |
| 2.261 | 2-CF$_3$—C$_6$H$_4$—(CH$_2$)$_2$ |
| 2.262 | 4-CF$_3$—C$_6$H$_4$—(CH$_2$)$_2$ |
| 2.263 | 2-CH$_3$-3-CF$_3$—C$_6$H$_3$—(CH$_2$)$_2$ |
| 2.264 | 2-CH$_3$-4-CF$_3$—C$_6$H$_3$—(CH$_2$)$_2$ |
| 2.265 | 2-CF$_3$-3-CH$_3$—C$_6$H$_3$—(CH$_2$)$_2$ |
| 2.266 | 2-CF$_3$-4-CH$_3$—C$_6$H$_3$—(CH$_2$)$_2$ |
| 2.267 | 2-CF$_3$-5-CH$_3$—C$_6$H$_3$—(CH$_2$)$_2$ |
| 2.268 | 2-CH$_3$-5-CH$_3$—C$_6$H$_3$—(CH$_2$)$_2$ |
| 2.269 | 2-Br—C$_6$H$_4$—(CH$_2$)$_2$ |
| 2.270 | 3-Br—C$_6$H$_4$—(CH$_2$)$_2$ |
| 2.271 | 4-Br—C$_6$H$_4$—(CH$_2$)$_2$ |
| 2.272 | 2-(iso-Propyl)-C$_6$H$_4$—(CH$_2$)$_2$ |
| 2.273 | 3-(iso-Propyl)-C$_6$H$_4$—(CH$_2$)$_2$ |
| 2.274 | 4-(iso-Propyl)-C$_6$H$_4$—(CH$_2$)$_2$ |
| 2.275 | 2-(iso-Propyl)-3-Cl—C$_6$H$_3$—(CH$_2$)$_2$ |
| 2.276 | 2-(iso-Propyl)-4-Cl—C$_6$H$_3$—(CH$_2$)$_2$ |
| 2.277 | 2-(iso-Propyl)-5-Cl—C$_6$H$_3$—(CH$_2$)$_2$ |
| 2.278 | 2-CH$_3$-3-(iso-Propyl)-C$_6$H$_3$—(CH$_2$)$_2$ |
| 2.279 | 2-CH$_3$-4-(iso-Propyl)-C$_6$H$_3$—(CH$_2$)$_2$ |
| 2.280 | 2-CH$_3$-5-(iso-Propyl)-C$_6$H$_3$—(CH$_2$)$_2$ |
| 2.281 | 2-t-C$_4$H$_9$—(CH$_2$)$_2$ |
| 2.282 | 3-t-C$_4$H$_9$—(CH$_2$)$_2$ |
| 2.283 | 4-t-C$_4$H$_9$—(CH$_2$)$_2$ |
| 2.284 | 2-CH$_3$-3-t-C$_4$H$_9$—C$_6$H$_3$—(CH$_2$)$_2$ |
| 2.285 | 2-CH$_3$-4-t-C$_4$H$_9$—C$_6$H$_3$—(CH$_2$)$_2$ |
| 2.286 | 2-CH$_3$-5-t-C$_4$H$_9$—C$_6$H$_3$—(CH$_2$)$_2$ |
| 2.287 | 3-CH$_3$-4-t-C$_4$H$_9$—C$_6$H$_3$—(CH$_2$)$_2$ |
| 2.288 | 3-CH$_3$-5-t-C$_4$H$_9$—C$_6$H$_3$—(CH$_2$)$_2$ |
| 2.289 | 2-Cl-3-t-C$_4$H$_9$—C$_6$H$_3$—(CH$_2$)$_2$ |
| 2.290 | 2-Cl-4-t-C$_4$H$_9$—C$_6$H$_3$—(CH$_2$)$_2$ |
| 2.291 | 2-Cl-5-t-C$_4$H$_9$—C$_6$H$_3$—(CH$_2$)$_2$ |
| 2.292 | 3-Cl-4-t-C$_4$H$_9$—C$_6$H$_3$—(CH$_2$)$_2$ |
| 2.293 | 3-Cl-5-t-C$_4$H$_9$—C$_6$H$_3$—(CH$_2$)$_2$ |
| 2.294 | 2-OCH$_3$—C$_6$H$_4$—(CH$_2$)$_2$ |
| 2.295 | 3-OCH$_3$—C$_6$H$_4$—(CH$_2$)$_2$ |
| 2.296 | 4-OCH$_3$—C$_6$H$_4$—(CH$_2$)$_2$ |
| 2.297 | 2-CH$_3$-3-OCH$_3$—C$_6$H$_3$—(CH$_2$)$_2$ |
| 2.298 | 2-CH$_3$-4-OCH$_3$—C$_6$H$_3$—(CH$_2$)$_2$ |
| 2.299 | 2-CH$_3$-5-OCH$_3$—C$_6$H$_3$—(CH$_2$)$_2$ |
| 2.300 | 3-CH$_3$-5-OCH$_3$—C$_6$H$_3$—(CH$_2$)$_2$ |
| 2.301 | 3-CH$_3$-5-OCH$_3$—C$_6$H$_3$—(CH$_2$)$_2$ |
| 2.302 | 2-Cl-3-OCH$_3$—C$_6$H$_3$—(CH$_3$)$_2$ |
| 2.303 | 2-Cl-4-OCH$_3$—C$_6$H$_3$—(CH$_3$)$_2$ |
| 2.304 | 2-Cl-5-OCH$_3$—C$_6$H$_3$—(CH$_3$)$_2$ |
| 2.305 | 2-OCH$_3$-3-Cl—C$_6$H$_3$—(CH$_3$)$_2$ |
| 2.306 | 2-OCH$_3$-4-Cl—C$_6$H$_3$—(CH$_3$)$_2$ |
| 2.307 | 2-OCH$_3$-5-Cl—C$_6$H$_3$—(CH$_3$)$_2$ |
| 2.308 | 2-CH$_3$-4-(Cyclohexyl)-C$_6$H$_3$—(CH$_2$)$_2$ |
| 2.309 | 2-CH$_3$-4-C$_6$H$_5$—C$_6$H$_3$—(CH$_2$)$_2$ |
| 2.310 | 2-CH$_3$-3-Br—C$_6$H$_3$—(CH$_2$)$_2$ |
| 2.311 | 2-CH$_3$-4-Br—C$_6$H$_3$—(CH$_2$)$_2$ |
| 2.312 | 3-CH$_3$-5-Br—C$_6$H$_3$—(CH$_2$)$_2$ |
| 2.313 | 2-CH$_3$-3-(Methoxyiminomethyl)-C$_6$H$_3$—(CH$_2$)$_2$ |
| 2.314 | 2-Methoxyiminomethyl-C$_6$H$_4$—(CH$_2$)$_2$ |
| 2.315 | 3-Methoxyiminomethyl-C$_6$H$_4$—(CH$_2$)$_2$ |
| 2.316 | 2-CH$_3$-4-(Methoxyiminomethyl)-C$_6$H$_3$—(CH$_2$)$_2$ |
| 2.317 | 2-Phenyl-C$_6$H$_4$—(CH$_2$)$_2$ |
| 2.318 | 3-Phenyl-C$_6$H$_4$—(CH$_2$)$_2$ |
| 2.319 | 4-Phenyl-C$_6$H$_4$—(CH$_2$)$_2$ |
| 2.320 | 2-Phenoxy-C$_6$H$_4$—(CH$_2$)$_2$ |
| 2.321 | 3-Phenoxy-C$_6$H$_4$—(CH$_2$)$_2$ |
| 2.322 | 4-Phenoxy-C$_6$H$_4$—(CH$_2$)$_2$ |
| 2.323 | 2-Benzyloxy-C$_6$H$_4$—(CH$_2$)$_2$ |
| 2.324 | 2-Benzyloxy-C$_6$H$_4$—(CH$_2$)$_2$ |
| 2.325 | 4-Benzyloxy-C$_6$H$_4$—(CH$_2$)$_2$ |
| 2.326 | 1-Naphthyl-(CH$_2$)$_2$ |
| 2.327 | 2-Naphthyl-(CH$_2$)$_2$ |
| 2.328 | 9-Anthryl-(CH$_2$)$_2$ |
| 2.329 | 2-CH$_3$-3-C$_6$H$_5$O—C$_6$H$_3$—(CH$_2$)$_2$ |
| 2.330 | 2-CH$_3$-4-C$_6$H$_5$O—C$_6$H$_3$—(CH$_2$)$_2$ |
| 2.331 | 2-CH$_3$-5-C$_6$H$_5$O—C$_6$H$_3$—(CH$_2$)$_2$ |
| 2.332 | 3-CH$_3$-4-C$_6$H$_5$O—C$_6$H$_3$—(CH$_2$)$_2$ |

-continued

| | |
|---|---|
| 2.333 | 4-CH$_3$-5-C$_6$H$_5$O—C$_6$H$_3$—(CH$_2$)$_2$ |
| 2.334 | 2-Cl-3-C$_6$H$_5$O—C$_6$H$_3$—(CH$_2$)$_2$ |
| 2.335 | 2-Cl-4-C$_6$H$_5$O—C$_6$H$_3$—(CH$_2$)$_2$ |
| 2.336 | 2-Cl-5-C$_6$H$_5$O—C$_6$H$_3$—(CH$_2$)$_2$ |
| 2.337 | 3-Cl-4-C$_6$H$_5$O—C$_6$H$_3$—(CH$_2$)$_2$ |
| 2.338 | 3-Cl-5-C$_6$H$_5$O—C$_6$H$_3$—(CH$_2$)$_2$ |
| 2.339 | 2-CH$_3$-4-COCH$_3$—C$_6$H$_3$—(CH$_2$)$_2$ |
| 2.340 | 2-CH$_3$-4-COCH$_3$—C$_6$H$_3$—(CH$_2$)$_2$ |
| 2.341 | C$_6$H$_5$—CH=CH—CH$_2$ |
| 2.342 | 2-F—C$_6$H$_4$—CH=CH—CH$_2$ |
| 2.343 | 2-F—C$_6$H$_4$—CH=CH—CH$_2$ |
| 2.344 | 4-F—C$_6$H$_4$—CH=CH—CH$_2$ |
| 2.345 | 2-Cl—C$_6$H$_4$—CH=CH—CH$_2$ |
| 2.346 | 3-Cl—C$_6$H$_4$—CH=CH—CH$_2$ |
| 2.347 | 4-Cl—C$_6$H$_4$—CH=CH—CH$_2$ |
| 2.348 | 2,3-Cl$_2$—C$_6$H$_3$—CH=CH—CH$_2$ |
| 2.349 | 2,4-Cl$_2$—C$_6$H$_3$—CH=CH—CH$_2$ |
| 2.350 | 2,5-Cl$_2$—C$_6$H$_3$—CH=CH—CH$_2$ |
| 2.351 | 2,6-Cl$_2$—C$_6$H$_3$—CH=CH—CH$_2$ |
| 2.352 | 3,4-Cl$_2$—C$_6$H$_3$—CH=CH—CH$_2$ |
| 2.353 | 2-CH$_3$—C$_6$H$_4$CH=CH—CH$_2$ |
| 2.354 | 3-CH$_3$—C$_6$H$_4$CH=CH—CH$_2$ |
| 2.355 | 4-CH$_3$—C$_6$H$_4$CH=CH—CH$_2$ |
| 2.356 | 2,3-(CH$_3$)$_2$—C$_6$H$_3$—CH=CH—CH$_2$ |
| 2.358 | 2,5-(CH$_3$)$_2$—C$_6$H$_3$—CH=CH—CH$_2$ |
| 2.359 | 3,4-(CH$_3$)$_2$—C$_6$H$_3$—CH=CH—CH$_2$ |
| 2.360 | 4,5-(CH$_3$)$_2$—C$_6$H$_3$—CH=CH—CH$_2$ |
| 2.362 | 2,3,4-(CH$_3$)$_2$—C$_6$H$_3$—CH=CH—CH$_2$ |
| 2.363 | 2,4,5-(CH$_3$)$_2$—C$_6$H$_3$—CH=CH—CH$_2$ |
| 2.364 | 2,4,6-(CH$_3$)$_2$—C$_6$H$_3$—CH=CH—CH$_2$ |
| 2.365 | 2,3,6-(CH$_3$)$_2$—C$_6$H$_3$—CH=CH—CH$_2$ |
| 2.366 | 2-CF$_3$—C$_6$H$_4$—CH=CH—CH$_2$ |
| 2.367 | 3-CF$_3$—C$_6$H$_4$—CH=CH—CH$_2$ |
| 2.368 | 4-CF$_3$—C$_6$H$_4$—CH=CH—CH$_2$ |
| 2.369 | 2-CH$_3$-3-CF$_3$—C$_6$H$_3$—CH=CH—CH$_2$ |
| 2.370 | 2-CH$_3$-4-CF$_3$—C$_6$H$_3$—CH=CH—CH$_2$ |
| 2.371 | 2-CF$_3$-3-CF$_3$—C$_6$H$_3$—CH=CH—CH$_2$ |
| 2.372 | 2-CF$_3$-4-CH$_3$—C$_6$H$_3$—CH=CH—CH$_2$ |
| 2.373 | 2-CF$_3$-5-CH$_3$—C$_6$H$_3$—CH=CH—CH$_2$ |
| 2.374 | 2-CH$_3$-5-CF$_3$—C$_6$H$_3$—CH=CH—CH$_2$ |
| 2.375 | C$_6$H$_5$—(CH$_2$)$_3$ |
| 2.376 | C$_6$H$_5$—(CH$_2$)$_4$ |
| 2.377 | C$_6$H$_5$—CH$_2$CH=CH—CH$_2$ |
| 2.378 | 4-F—C$_6$H$_4$—CH=CH—(CH$_2$)$_2$ |
| 2.379 | CH$_3$O—CO—CH$_2$ |
| 2.380 | CH$_3$CH$_2$O—CO—CH$_2$ |
| 2.381 | CH$_3$—CO—CH$_2$—CH$_2$ |
| 2.382 | t-C$_4$H$_9$O—CO—(CH$_2$)$_3$ |
| 2.383 | t-C$_4$H$_9$O—CO—(CH$_2$)$_3$ |
| 2.384 | t-C$_4$H$_9$O—CO—CH$_2$ |
| 2.385 | n-C$_4$H$_9$O—CO—CH$_2$ |
| 2.386 | iso-C$_4$H$_9$O—CO—CH$_2$ |
| 2.387 | n-C$_3$H$_7$O—CO—CH$_2$ |
| 2.388 | sec.-C$_4$H$_9$O—CO—CH$_2$ |
| 2.389 | C$_6$H$_5$—CO—CH$_2$ |
| 2.390 | 2-CH$_3$—C$_6$H$_4$O—CO—CH$_2$ |
| 2.391 | 3-CH$_3$—C$_6$H$_4$O—CO—CH$_2$ |
| 2.392 | 4-CH$_3$—C$_6$H$_4$O—CO—CH$_2$ |
| 2.393 | 2-Cl—C$_6$H$_4$O—CO—CH$_2$ |
| 2.394 | 3-Cl—C$_6$H$_4$O—CO—CH$_2$ |
| 2.395 | 4-Cl—C$_6$H$_4$O—CO—CH$_2$ |
| 2.396 | C$_6$H$_5$—C(CH$_3$)=CH—CH$_2$ |

2.397

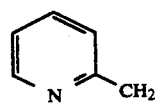

2.398

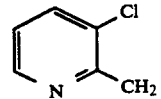

2.399

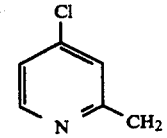

-continued
2.400 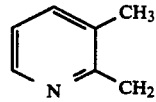
2.401 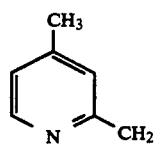
2.402 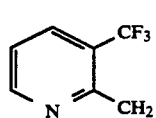
2.403 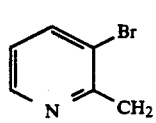
2.404 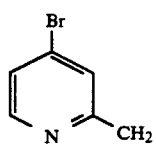
2.405 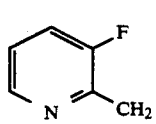
2.406 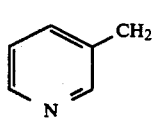
2.407 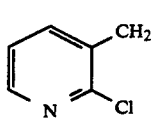
2.408 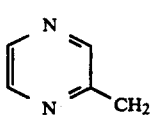
2.409 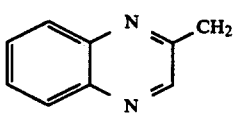
2.410 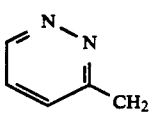
2.411 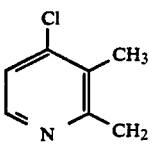

-continued
2.412 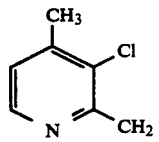
2.413 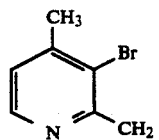
2.414 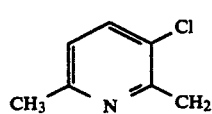
2.415 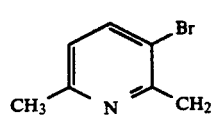
2.416 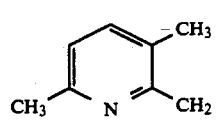
2.417 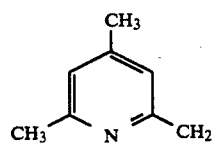
2.418 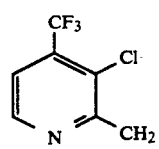
2.419 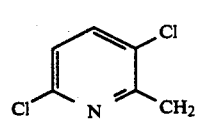
2.420 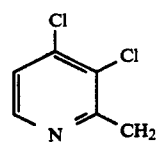
2.421 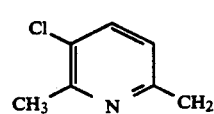
2.422 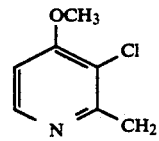
2.423 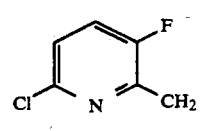

-continued
2.424 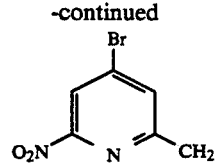
2.425 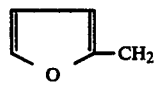
2.426 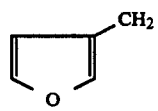
2.427 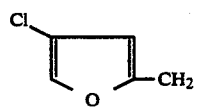
2.428 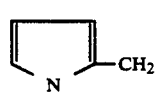
2.429 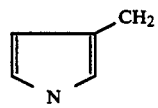
2.430 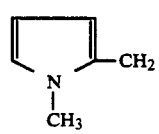
2.431 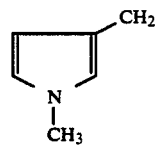
2.432 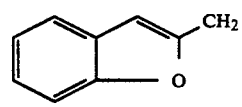
2.433 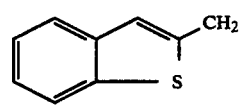
2.434 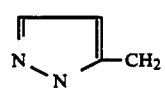
2.435 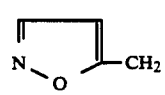
2.436 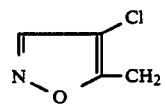

-continued
2.437 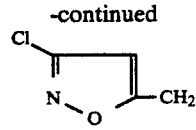
2.438 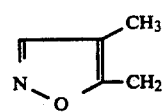
2.439 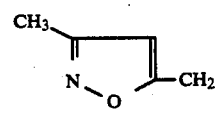
2.440 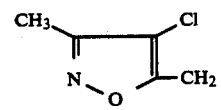
2.441 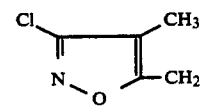
2.442 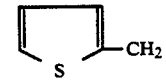
2.443 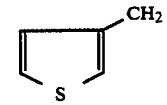
2.444 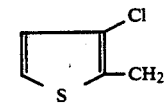
2.445 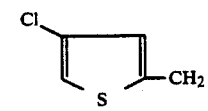
2.446 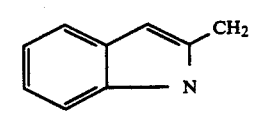
2.447 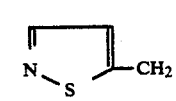
2.448 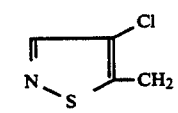
2.449 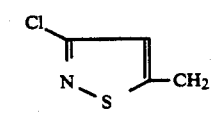
2.450 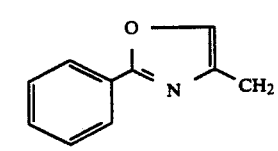

2.451 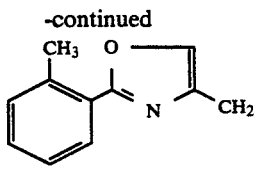
2.452 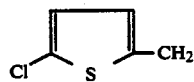
2.453 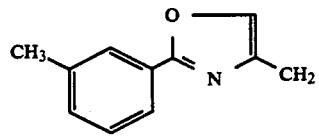
2.454 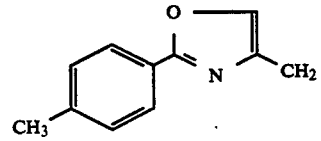
2.455 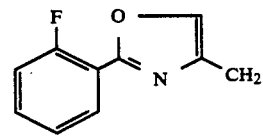
2.456 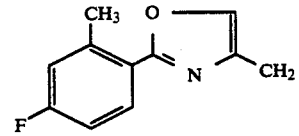
2.457 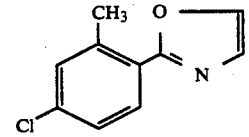
2.458 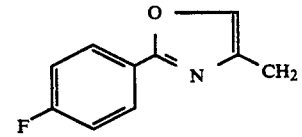
2.459 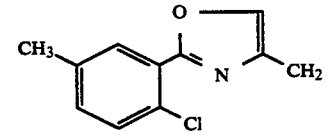
2.460 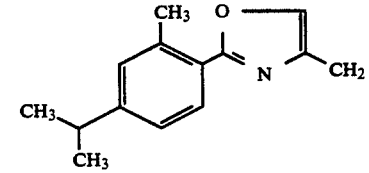
2.461 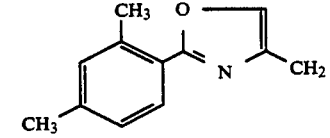

-continued

| | |
|---|---|
| 2.462 | N≡C—CH$_2$ |
| 2.463 | t-BuO—CH$_2$—CH=CH—CH$_2$ |
| 2.464 | (CH$_3$)$_2$—C=CH—CH$_2$—CH$_2$—C=CH—CH$_2$<br>　　　　　　　　　　　　　　　　　　｜<br>　　　　　　　　　　　　　　　　　　CH$_3$ |

TABLE III

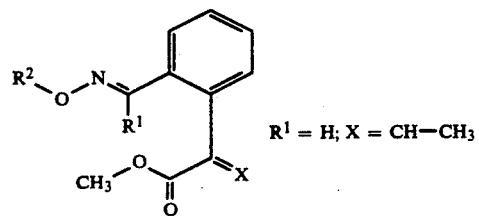

R$^1$ = H; X = CH—CH$_3$

| Comp. no. | R$^2$ | IR (cm$^{-1}$) |
|---|---|---|
| 3.1 | H | |
| 3.2 | CH$_3$ | |
| 3.3 | CH$_3$CH$_2$ | |
| 3.4 | CH$_3$CH$_2$CH$_2$ | |
| 3.5 | CH$_2$=CH—CH$_2$ | |
| 3.6 | CH$_3$—CH=CH | |
| 3.7 | CH$_3$—CH(CH$_3$) | |
| 3.8 | HC≡C—C(CH$_3$)=CH—CH$_2$ | |
| 3.9 | HC C—CH$_2$ | |
| 3.10 | CH$_3$—O—CH$_2$—CH$_2$ | |
| 3.11 | C$_2$H$_5$—O—CH$_2$—CH$_2$ | |
| 3.12 | Cl—CH$_2$—CH$_2$ | |
| 3.13 | Cyclo-C$_3$H$_5$—CH$_2$ | |
| 3.14 | CH$_3$—CH=CH—CH$_2$ | |
| 3.15 | CH$_2$=CH—CH$_2$—CH$_2$ | |
| 3.16 | CH$_3$—C≡C—CH$_2$ | |
| 3.17 | CH$_3$CH$_2$—C≡C—CH$_2$ | |
| 3.18 | CH$_3$—(CH$_2$)$_3$ | |
| 3.19 | CH$_3$—(CH$_2$)$_4$ | |
| 3.20 | (CH$_3$)$_3$C | |
| 3.21 | Cyclo-C$_6$H$_{11}$ | |
| 3.22 | 2-CH$_3$-Cyclo-C$_6$H$_{10}$ | |
| 3.23 | C$_6$H$_5$—CH$_2$ | |
| 3.24 | 2-F—C$_6$H$_4$—CH$_2$ | |
| 3.25 | 3-F—C$_6$H$_4$—CH$_2$ | |
| 3.26 | 4-F—C$_6$H$_4$—CH$_2$ | |
| 3.27 | 2-Cl—C$_6$H$_4$—CH$_2$ | |
| 3.28 | 3-Cl—C$_6$H$_4$—CH$_2$ | |
| 3.29 | 4-Cl—C$_6$H$_4$—CH$_2$ | |
| 3.30 | 2,3-Cl$_2$—C$_6$H$_3$—CH$_2$ | |
| 3.31 | 2,4-Cl$_2$—C$_6$H$_3$—CH$_2$ | |
| 3.32 | 2,5-Cl$_2$—C$_6$H$_3$—CH$_2$ | |
| 3.33 | 2,6-Cl$_2$—C$_6$H$_3$—CH$_2$ | |
| 3.34 | 3,4-Cl$_2$—C$_6$H$_3$—CH$_2$ | |
| 3.35 | 2-CH$_3$—C$_6$H$_4$—CH$_2$ | |
| 3.36 | 3-CH$_3$—C$_6$H$_4$—CH$_2$ | |
| 3.37 | 4-CH$_3$—C$_6$H$_4$—CH$_2$ | |
| 3.38 | 2,3-(CH$_3$)$_2$—C$_6$H$_3$—CH$_2$ | |
| 3.39 | 2,4-(CH$_3$)$_2$—C$_6$H$_3$—CH$_2$ | |
| 3.40 | 2,5-(CH$_3$)$_2$—C$_6$H$_3$—CH$_2$ | |
| 3.41 | 3,4-(CH$_3$)$_2$—C$_6$H$_3$—CH$_2$ | |
| 3.42 | 3,5-(CH$_3$)$_2$—C$_6$H$_3$—CH$_2$ | |
| 3.43 | 4,5-(CH$_3$)$_2$—C$_6$H$_3$—CH$_2$ | |
| 3.44 | 2,3,4-(CH$_3$)$_3$—C$_6$H$_2$—CH$_2$ | |
| 3.45 | 2,4,5-(CH$_3$)$_3$—C$_6$H$_2$—CH$_2$ | |
| 3.46 | 2,4,6-(CH$_3$)$_3$—C$_6$H$_2$—CH$_2$ | |
| 3.47 | 2,3,6-(CH$_3$)$_3$—C$_6$H$_2$—CH$_2$ | |
| 3.48 | 2-CF$_3$—C$_6$H$_4$—CH$_2$ | |
| 3.49 | 3-CF$_3$—C$_6$H$_4$—CH$_2$ | |
| 3.50 | 4-CF$_3$—C$_6$H$_4$—CH$_2$ | |
| 3.51 | 2-CH$_3$-3-CF$_3$—C$_6$H$_3$—CH$_2$ | |
| 3.52 | 2-CH$_3$-4-CF$_3$—C$_6$H$_3$—CH$_2$ | |
| 3.53 | 2-CF$_3$-3-CH$_3$—C$_6$H$_3$—CH$_2$ | |
| 3.54 | 2-CF$_3$-4-CH$_3$—C$_6$H$_3$—CH$_2$ | |
| 3.55 | 2-CH$_2$-5-CH$_3$—C$_6$H$_3$—CH$_2$ | |
| 3.56 | 2-CH$_3$-5-CF$_3$—C$_6$H$_3$—CH$_2$ | |
| 3.57 | 2-Br—C$_6$H$_4$—CH$_2$ | |
| 3.58 | 3-Br—C$_6$H$_4$—CH$_2$ | |

TABLE III-continued

| | |
|---|---|
| 3.59 | 4-Br—$C_6H_4$—$CH_2$ |
| 3.60 | 2-(iso-Propyl)-$C_6H_4$—$CH_2$ |
| 3.61 | 3-(iso-Propyl)-$C_6H_4$—$CH_2$ |
| 3.62 | 4-(iso-Propyl)-$C_6H_4$—$CH_2$ |
| 3.63 | 2-(iso-Propyl)-3-Cl—$C_6H_3$—$CH_2$ |
| 3.64 | 2-(iso-Propyl)-4-Cl—$C_6H_3$—$CH_2$ |
| 3.65 | 2-(iso-Propyl)-5-Cl—$C_6H_3$—$CH_2$ |
| 3.66 | 2-$CH_3$-3-(iso-Propyl)-$C_6H_3$—$CH_2$ |
| 3.67 | 2-$CH_3$-4-(iso-Propyl)-$C_6H_3$—$CH_2$ |
| 3.68 | 2-$CH_3$-5-(iso-Propyl)-$C_6H_3$—$CH_2$ |
| 3.69 | 2-t-$C_4H_9$—$C_6H_4$—$CH_2$ |
| 3.70 | 3-t-$C_4H_9$—$C_6H_4$—$CH_2$ |
| 3.71 | 4-t-$C_4H_9$—$C_6H_4$—$CH_2$ |
| 3.72 | 2-$CH_3$-3-t-$C_4H_9$—$C_6H_3$—$CH_2$ |
| 3.73 | 2-$CH_3$-4-t-$C_4H_9$—$C_6H_3$—$CH_2$ |
| 3.74 | 2-$CH_3$-5-t-$C_4H_9$—$C_6H_3$—$CH_2$ |
| 3.75 | 3-$CH_3$-4-t-$C_4H_9$—$C_6H_3$—$CH_2$ |
| 3.76 | 3-$CH_3$-5-t-$C_4H_9$—$C_6H_3$—$CH_2$ |
| 3.77 | 2-Cl-3-t-$C_4H_9$—$C_6H_3$—$CH_2$ |
| 3.78 | 2-Cl-4-t-$C_4H_9$—$C_6H_3$—$CH_2$ |
| 3.79 | 2-Cl-5-t-$C_4H_9$—$C_6H_3$—$CH_2$ |
| 3.80 | 3-Cl-n-t-$C_4H_9$—$C_6H_3$—$CH_2$ |
| 3.81 | 3-Cl-4-t-$C_4H_9$—$C_6H_3$—$CH_2$ |
| 3.82 | 2-$OCH_3$—$C_6H_4$—$CH_2$ |
| 3.83 | 3-$OCH_3$—$C_6H_4$—$CH_2$ |
| 3.84 | 4-$OCH_3$—$C_6H_4$—$CH_2$ |
| 3.85 | 2-$CH_3$-3-$OCH_3$—$C_6H_3$—$CH_2$ |
| 3.87 | 2-$CH_3$-5-$OCH_3$—$C_6H_3$—$CH_2$ |
| 3.88 | 3-$CH_3$-4-$OCH_3$—$C_6H_3$—$CH_2$ |
| 3.89 | 3-$CH_3$-5-$OCH_3$—$C_6H_3$—$CH_2$ |
| 3.90 | 2-Cl-3-$OCH_3$—$C_6H_3$—$CH_2$ |
| 3.91 | 2-Cl-4-$OCH_3$—$C_6H_3$—$CH_2$ |
| 3.92 | 2-Cl-5-$OCH_3$—$C_6H_3$—$CH_2$ |
| 3.93 | 2-$OCH_3$-3-Cl—$C_6H_3$—$CH_2$ |
| 3.94 | 2-$OCH_3$-4-Cl—$C_6H_3$—$CH_2$ |
| 3.95 | 2-$OCH_3$-5-Cl—$C_6H_3$—$CH_2$ |
| 3.96 | 2-$CH_3$-4-(Cyclohexyl)-$C_6H_3$—$CH_2$ |
| 3.97 | 2-$CH_3$-4-$C_6H_5$—$C_6H_3$—$CH_2$ |
| 3.98 | 2-$CH_3$-3-Br—$C_6H_3$—$CH_2$ |
| 3.99 | 2-$CH_3$-4-Br—$C_6H_3$—$CH_2$ |
| 3.100 | 2-$CH_3$-5-Br—$C_6H_3$—$CH_2$ |
| 3.101 | 2-$CH_3$-3-Methoxyiminomethyl-$C_6H_3$—$CH_2$ |
| 3.102 | 2-Methoxyiminomethyl-$C_6H_4$—$CH_4$ |
| 3.103 | 3-Methoxyiminomethyl-$C_6H_4$—$CH_4$ |
| 3.104 | 2-$CH_3$-4-(Methoxyiminomethyl)-$C_6H_3$—$CH_2$ |
| 3.105 | 2-Phenyl-$C_6H_4$—$CH_2$ |
| 3.106 | 3-Phenyl-$C_6H_4$—$CH_2$ |
| 3.107 | 4-Phenyl-$C_6H_4$—$CH_2$ |
| 3.108 | 2-Phenoxy-$C_6H_4$—$CH_2$ |
| 3.109 | 3-Phenoxy-$C_6H_4$—$CH_2$ |
| 3.110 | 4-Phenoxy-$C_6H_4$—$CH_2$ |
| 3.111 | 2-Benzyloxy-$C_6H_4$—$CH_2$ |
| 3.112 | 3-Benzyloxy-$C_6H_4$—$CH_2$ |
| 3.113 | 4-Benzyloxy-$C_6H_4$—$CH_2$ |
| 3.114 | 1-Naphthyl-$CH_2$ |
| 3.115 | 2-Naphthyl-$CH_2$ |
| 3.116 | 9-Anthryl-$CH_2$ |
| 3.117 | 2-$CH_3$-3-$C_6H_5O$—$C_6H_3$—$CH_2$ |
| 3.118 | 2-$CH_3$-4-$C_6H_5O$—$C_6H_3$—$CH_2$ |
| 3.119 | 2-$CH_3$-5-$C_6H_5O$—$C_6H_3$—$CH_2$ |
| 3.120 | 3-$CH_3$-4-$C_6H_5O$—$C_6H_3$—$CH_2$ |
| 3.121 | 4-$CH_3$-5-$C_6H_5O$—$C_6H_3$—$CH_2$ |
| 3.122 | 2-Cl-3-$C_6H_5O$—$C_6H_3$—$CH_2$ |
| 3.123 | 2-Cl-4-$C_6H_5O$—$C_6H_3$—$CH_2$ |
| 3.124 | 2-Cl-5-$C_6H_5O$—$C_6H_3$—$CH_2$ |
| 3.125 | 3-Cl-4-$C_6H_5O$—$C_6H_3$—$CH_2$ |
| 3.126 | 3-Cl-5-$C_6H_5O$—$C_6H_3$—$CH_2$ |
| 3.127 | 2-$CH_3$-4-$CO_2CH_3$—$C_6H_3$—$CH_2$ |
| 3.128 | 2-$CH_3$-5-$CO_2CH_3$—$C_6H_3$—$CH_2$ |
| 3.129 | $C_6H_5$—CH—($CH_3$) |
| 3.130 | 2-F—$C_6H_4$—CH($CH_3$) |
| 3.131 | 2-F—$C_6H_4$—CH($CH_3$) |
| 3.132 | 4-F—$C_6H_4$—CH($CH_3$) |
| 3.133 | 2-Cl—$C_6H_4$—CH($CH_3$) |
| 3.134 | 3-Cl—$C_6H_4$—CH($CH_3$) |
| 3.135 | 4-Cl—$C_6H_4$—CH($CH_3$) |
| 3.136 | 2,3-$Cl_2$—$C_6H_3$—CH($CH_3$) |
| 3.137 | 2,4-$Cl_2$—$C_6H_3$—CH($CH_3$) |
| 3.138 | 2,5-$Cl_2$—$C_6H_3$—CH($CH_3$) |
| 3.139 | 2,6-$Cl_2$—$C_6H_3$—CH($CH_3$) |
| 3.140 | 3,4-$Cl_2$—$C_6H_3$—CH($CH_3$) |
| 3.141 | 2-$CH_3$—$C_6H_4$—CH($CH_3$) |

TABLE III-continued

| | |
|---|---|
| 3.142 | 3-CH$_3$—C$_6$H$_4$—CH(CH$_3$) |
| 3.143 | 4-CH$_3$—C$_6$H$_4$—CH(CH$_3$) |
| 3.144 | 2,3-(CH$_3$)$_2$—C$_6$H$_3$—CH(CH$_3$) |
| 3.145 | 2,4-(CH$_3$)$_2$—C$_6$H$_3$—CH(CH$_3$) |
| 3.146 | 2,5-(CH$_3$)$_2$—C$_6$H$_3$—CH(CH$_3$) |
| 3.147 | 3,4-(CH$_3$)$_2$—C$_6$H$_3$—CH(CH$_3$) |
| 3.148 | 3,5-(CH$_3$)$_2$—C$_6$H$_3$—CH(CH$_3$) |
| 3.149 | 4,5-(CH$_3$)$_2$—C$_6$H$_3$—CH(CH$_3$) |
| 3.150 | 2,3,4-(CH$_3$)$_3$—C$_6$H$_2$—CH(CH$_3$) |
| 3.151 | 2,4,5-(CH$_3$)$_3$—C$_6$H$_2$—CH(CH$_3$) |
| 3.152 | 2,4,6-(CH$_3$)$_3$—C$_6$H$_2$—CH(CH$_3$) |
| 3.153 | 2,2,6-(CH$_3$)$_3$—C$_6$H$_2$—CH(CH$_3$) |
| 3.154 | 2-CF$_3$—C$_6$H$_4$—CH(CH$_3$) |
| 3.155 | 2-CF$_3$—C$_6$H$_4$—CH(CH$_3$) |
| 3.156 | 4-CF$_3$—C$_6$H$_4$—CH(CH$_3$) |
| 3.157 | 2-CH$_3$-3-CF$_3$—C$_6$H$_3$—CH(CH$_3$) |
| 3.158 | 2-CH$_3$-4-CF$_3$—C$_6$H$_3$—CH(CH$_3$) |
| 3.159 | 2-CF$_3$-3-CH$_3$—C$_6$H$_3$—CH(CH$_3$) |
| 3.160 | 2-CF$_3$-4-CH$_3$—C$_6$H$_3$—CH(CH$_3$) |
| 3.161 | 2-CF$_3$-5-CH$_3$—C$_6$H$_3$—CH(CH$_3$) |
| 3.162 | 2-CH$_3$-5-CF$_3$—C$_6$H$_3$—CH(CH$_3$) |
| 3.163 | 2-Br—C$_6$H$_4$—CH(CH$_3$) |
| 3.164 | 3-Br—C$_6$H$_4$—CH(CH$_3$) |
| 3.165 | 4-Br—C$_6$H$_4$—CH(CH$_3$) |
| 3.166 | 2-(iso-Propyl)-C$_6$H$_4$—CH(CH$_3$) |
| 3.167 | 3-(iso-Propyl)-C$_6$H$_4$—CH(CH$_3$) |
| 3.168 | 4-(iso-Propyl)-C$_6$H$_4$—CH(CH$_3$) |
| 3.169 | 2-(iso-Propyl)-3-Cl—C$_6$H$_3$—CH(CH$_3$) |
| 3.170 | 2-(iso-Propyl)-4-Cl—C$_6$H$_3$—CH(CH$_3$) |
| 3.171 | 2-(iso-Propyl)-5-Cl—C$_6$H$_3$—CH(CH$_3$) |
| 3.172 | 2-CH$_3$-3-(iso-Propyl)-C$_6$H$_3$—CH(CH$_3$) |
| 3.173 | 2-CH$_3$-4-(iso-Propyl)-C$_6$H$_3$—CH(CH$_3$) |
| 3.174 | 2-CH$_3$-5-(iso-Propyl)-C$_6$H$_3$—CH(CH$_3$) |
| 3.175 | 2-t-C$_4$H$_9$—CH$_6$H$_4$—CH(CH$_3$) |
| 3.176 | 3-t-C$_4$H$_9$—CH$_6$H$_4$—CH(CH$_3$) |
| 3.177 | 4-t-C$_4$H$_9$—CH$_6$H$_4$—CH(CH$_3$) |
| 3.178 | 2-CH$_3$-3-t-C$_4$H$_9$—C$_6$H$_3$—CH(CH$_3$) |
| 3.179 | 2-CH$_3$-4-t-C$_4$H$_9$—C$_6$H$_3$—CH(CH$_3$) |
| 3.180 | 2-CH$_3$-5-t-C$_4$H$_9$—C$_6$H$_3$—CH(CH$_3$) |
| 3.181 | 3-CH$_3$-4-t-C$_4$H$_9$—C$_6$H$_3$—CH(CH$_3$) |
| 3.182 | 3-CH$_3$-3-t-C$_4$H$_9$—C$_6$H$_3$—CH(CH$_3$) |
| 3.183 | 2-Cl-3-t-C$_4$H$_9$—C$_6$H$_3$—CH(CH$_3$) |
| 3.184 | 2-Cl-4-t-C$_4$H$_9$—C$_6$H$_3$—CH(CH$_3$) |
| 3.185 | 2-Cl-5-t-C$_4$H$_9$—C$_6$H$_3$—CH(CH$_3$) |
| 3.186 | 3-Cl-4-t-C$_4$H$_9$—C$_6$H$_3$—CH(CH$_3$) |
| 3.187 | 3-Cl-5-t-C$_4$H$_9$—C$_6$H$_3$—CH(CH$_3$) |
| 3.188 | 2-OCH$_3$—C$_6$H$_4$—CH$_2$—CH(CH$_3$) |
| 3.189 | 3-OCH$_3$—C$_6$H$_4$—CH$_2$—CH(CH$_3$) |
| 3.190 | 4-OCH$_3$—C$_6$H$_4$—CH$_2$—CH(CH$_3$) |
| 3.191 | 2-CH$_3$-3-OCH$_3$—C$_6$H$_3$—CH(CH$_3$) |
| 3.192 | 2-CH$_3$-4-OCH$_3$—C$_6$H$_3$—CH(CH$_3$) |
| 3.193 | 2-CH$_3$-5-OCH$_3$—C$_6$H$_3$—CH(CH$_3$) |
| 3.194 | 3-CH$_3$-5-OCH$_3$—C$_6$H$_3$—CH(CH$_3$) |
| 3.195 | 3-CH$_3$-5-OCH$_3$—C$_6$H$_3$—CH(CH$_3$) |
| 3.196 | 2-Cl-3-OCH$_3$—C$_6$H$_3$—CH(CH$_3$) |
| 3.197 | 2-Cl-4-OCH$_3$—C$_6$H$_3$—CH(CH$_3$) |
| 3.198 | 2-Cl-5-OCH$_3$—C$_6$H$_3$—CH(CH$_3$) |
| 3.199 | 2-OCH$_3$-3-Cl-C$_6$H$_3$—CH(CH$_3$) |
| 3.200 | 2-OCH$_3$-4-Cl-C$_6$H$_3$—CH(CH$_3$) |
| 3.201 | 2-OCH$_3$-5-Cl-C$_6$H$_3$—CH(CH$_3$) |
| 3.202 | 2-CH$_3$-4-(Cyclohexyl)-C$_6$H$_3$—CH(CH$_3$) |
| 3.203 | 2-CH$_3$-4-C$_6$H$_5$—C$_6$H$_3$—CH(CH$_3$) |
| 3.204 | 2-CH$_3$-3-Br—C$_6$H$_3$—CH(CH$_3$) |
| 3.205 | 2-CH$_3$-4-Br—C$_6$H$_3$—CH(CH$_3$) |
| 3.206 | 3-CH$_3$-5-Br—C$_6$H$_3$—CH(CH$_3$) |
| 3.207 | 2-CH$_3$-3-(Methoxyiminomethyl)-C$_6$H$_3$—CH(CH$_3$) |
| 3.208 | 2-Methoxyiminomethyl-C$_6$H$_4$—CH(CH$_3$) |
| 3.209 | 3-Methoxyiminomethyl-C$_6$H$_4$—CH(CH$_3$) |
| 3.210 | 2-CH$_3$-4-(Methoxyiminomethyl)-C$_6$H$_3$—CH(CH$_3$) |
| 3.211 | 2-Phenyl-C$_6$H$_4$—CH(CH$_3$) |
| 3.212 | 3-Phenyl-C$_6$H$_4$—CH(CH$_3$) |
| 3.213 | 4-Phenyl-C$_6$H$_4$—CH(CH$_3$) |
| 3.214 | 2-Phenoxy-C$_6$H$_4$—CH(CH$_3$) |
| 3.215 | 3-Phenoxy-C$_6$H$_4$—CH(CH$_3$) |
| 3.216 | 4-Phenoxy-C$_6$H$_4$—CH(CH$_3$) |
| 3.217 | 2-Benzyloxy-C$_6$H$_4$—CH(CH$_3$) |
| 3.218 | 3-Benzyloxy-C$_6$H$_4$—CH(CH$_3$) |
| 3.219 | 4-Benzyloxy-C$_6$H$_4$—CH(CH$_3$) |
| 3.220 | 1-Naphthyl-CH(CH$_3$) |
| 3.221 | 2-Naphthyl-CH(CH$_3$) |
| 3.222 | 9-Anthryl-CH(CH$_3$) |
| 3.223 | 2-CH$_3$-3-C$_6$H$_5$O—C$_6$H$_3$—CH(CH$_3$) |

TABLE III-continued

| | |
|---|---|
| 3.224 | 2-CH$_3$-4-C$_6$H$_5$O—C$_6$H$_3$—CH(CH$_3$) |
| 3.225 | 2-CH$_3$-5-C$_6$H$_5$O—C$_6$H$_3$—CH(CH$_3$) |
| 3.226 | 3-CH$_3$-4-C$_6$H$_5$O—C$_6$H$_3$—CH(CH$_3$) |
| 3.227 | 4-CH$_3$-5-C$_6$H$_5$O—C$_6$H$_3$—CH(CH$_3$) |
| 3.228 | 2-Cl-3-C$_6$H$_5$O—C$_6$H$_3$—CH(CH$_3$) |
| 3.229 | 2-Cl-4-C$_6$H$_5$O—C$_6$H$_3$—CH(CH$_3$) |
| 3.230 | 2-Cl-5-C$_6$H$_5$O—C$_6$H$_3$—CH(CH$_3$) |
| 3.231 | 3-Cl-4-C$_6$H$_5$O—C$_6$H$_3$—CH(CH$_3$) |
| 3.232 | 3-Cl-5-C$_6$H$_5$O—C$_6$H$_3$—CH(CH$_3$) |
| 3.233 | 2-CH$_3$-4-CO$_2$CH$_3$—C$_6$H$_3$—CH(CH$_3$) |
| 3.234 | 2-CH$_3$-5-CO$_2$CH$_3$—C$_6$H$_3$—CH(CH$_3$) |
| 3.235 | C$_6$H$_5$—(CH$_2$)$_2$ |
| 3.236 | 2-F-C$_6$H$_4$—(CH$_2$)$_2$ |
| 3.237 | 2-F-C$_6$H$_4$—(CH$_2$)$_2$ |
| 3.238 | 4-F-C$_6$H$_4$—(CH$_2$)$_2$ |
| 3.239 | 2-Cl-C$_6$H$_4$—(CH$_2$)$_2$ |
| 3.240 | 3-Cl-C$_6$H$_4$—(CH$_2$)$_2$ |
| 3.241 | 4-Cl-C$_6$H$_4$—(CH$_2$)$_2$ |
| 3.242 | 2,3-Cl$_2$—C$_6$H$_3$—(CH$_2$)$_2$ |
| 3.243 | 2,4-Cl$_2$—C$_6$H$_3$—(CH$_2$)$_2$ |
| 3.244 | 2,5-Cl$_2$—C$_6$H$_3$—(CH$_2$)$_2$ |
| 3.245 | 2,6-Cl$_2$—C$_6$H$_3$—(CH$_2$)$_2$ |
| 3.246 | 3,4-Cl$_2$—C$_6$H$_3$—(CH$_2$)$_2$ |
| 3.247 | 2-CH$_3$—C$_6$H$_4$—(CH$_2$)$_2$ |
| 3.248 | 3-CH$_3$—C$_6$H$_4$—(CH$_2$)$_2$ |
| 3.249 | 4-CH$_3$—C$_6$H$_4$—(CH$_2$)$_2$ |
| 3.250 | 2,3-(CH$_3$)$_2$—C$_6$H$_3$—(CH$_2$)$_2$ |
| 3.251 | 2,4-(CH$_3$)$_2$—C$_6$H$_3$—(CH$_2$)$_2$ |
| 3.252 | 2,5-(CH$_3$)$_2$—C$_6$H$_3$—(CH$_2$)$_2$ |
| 3.253 | 3,4-(CH$_3$)$_2$—C$_6$H$_3$—(CH$_2$)$_2$ |
| 3.254 | 3,5-(CH$_3$)$_2$—C$_6$H$_3$—(CH$_2$)$_2$ |
| 3.255 | 4,5-(CH$_3$)$_2$—C$_6$H$_3$—(CH$_2$)$_2$ |
| 3.256 | 2,3,4-(CH$_3$)$_3$—C$_6$H$_2$—(CH$_2$)$_2$ |
| 3.257 | 2,4,5-(CH$_3$)$_3$—C$_6$H$_2$—(CH$_2$)$_2$ |
| 3.258 | 2,4,6-(CH$_3$)$_3$—C$_6$H$_2$—(CH$_2$)$_2$ |
| 3.259 | 2,2,6-(CH$_3$)$_3$—C$_6$H$_2$—(CH$_2$)$_2$ |
| 3.260 | 2-CF$_3$—C$_6$H$_4$—(CH$_2$)$_2$ |
| 3.261 | 2-CF$_3$—C$_6$H$_4$—(CH$_2$)$_2$ |
| 3.262 | 4-CF$_3$—C$_6$H$_4$—(CH$_2$)$_2$ |
| 3.263 | 2-CH$_3$-3-CF$_3$—C$_6$H$_3$—(CH$_2$)$_2$ |
| 3.264 | 2-CH$_3$-4-CF$_3$—C$_6$H$_3$—(CH$_2$)$_2$ |
| 3.265 | 2-CF$_3$-3-CH$_3$—C$_6$H$_3$—(CH$_2$)$_2$ |
| 3.266 | 2-CF$_3$-4-CH$_3$—C$_6$H$_3$—(CH$_2$)$_2$ |
| 3.267 | 2-CF$_3$-5-CH$_3$—C$_6$H$_3$—(CH$_2$)$_2$ |
| 3.268 | 2-CH$_3$-5-CH$_3$—C$_6$H$_3$—(CH$_2$)$_2$ |
| 3.269 | 2-Br—C$_6$H$_4$—(CH$_2$)$_2$ |
| 3.270 | 3-Br—C$_6$H$_4$—(CH$_2$)$_2$ |
| 3.271 | 4-Br—C$_6$H$_4$—(CH$_2$)$_2$ |
| 3.272 | 2-(iso-Propyl)-C$_6$H$_4$—(CH$_2$)$_2$ |
| 3.273 | 3-(iso-Propyl)-C$_6$H$_4$—(CH$_2$)$_2$ |
| 3.274 | 4-(iso-Propyl)-C$_6$H$_4$—(CH$_2$)$_2$ |
| 3.275 | 2-(iso-Propyl)-3-Cl—C$_6$H$_3$—(CH$_2$)$_2$ |
| 3.276 | 2-(iso-Propyl)-4-Cl—C$_6$H$_3$—(CH$_2$)$_2$ |
| 3.277 | 2-(iso-Propyl)-5-Cl—C$_6$H$_3$—(CH$_2$)$_2$ |
| 3.278 | 2-CH$_3$-3-(iso-Propyl)-C$_6$H$_3$—(CH$_2$)$_2$ |
| 3.279 | 2-CH$_3$-4-(iso-Propyl)-C$_6$H$_3$—(CH$_2$)$_2$ |
| 3.280 | 2-CH$_3$-5-(iso-Propyl)-C$_6$H$_3$—(CH$_2$)$_2$ |
| 3.281 | 2-t-C$_4$H$_9$—C$_6$H$_4$—(CH$_2$)$_2$ |
| 3.282 | 3-t-C$_4$H$_9$—C$_6$H$_4$—(CH$_2$)$_2$ |
| 3.283 | 4-t-C$_4$H$_9$—C$_6$H$_4$—(CH$_2$)$_2$ |
| 3.284 | 2-CH$_3$-3-t-C$_4$H$_9$—C$_6$H$_3$—(CH$_2$)$_2$ |
| 3.285 | 2-CH$_3$-4-t-C$_4$H$_9$—C$_6$H$_3$—(CH$_2$)$_2$ |
| 3.286 | 2-CH$_3$-5-t-C$_4$H$_9$—C$_6$H$_3$—(CH$_2$)$_2$ |
| 3.287 | 3-CH$_3$-4-t-C$_4$H$_9$—C$_6$H$_3$—(CH$_2$)$_2$ |
| 3.288 | 3-CH$_3$-5-t-C$_4$H$_9$—C$_6$H$_3$—(CH$_2$)$_2$ |
| 3.289 | 2-Cl-3-t-C$_4$H$_9$—C$_6$H$_3$—(CH$_2$)$_2$ |
| 3.290 | 2-Cl-4-t-C$_4$H$_9$—C$_6$H$_3$—(CH$_2$)$_2$ |
| 3.291 | 2-Cl-5-t-C$_4$H$_9$—C$_6$H$_3$—(CH$_2$)$_2$ |
| 3.292 | 3-Cl-4-t-C$_4$H$_9$—C$_6$H$_3$—(CH$_2$)$_2$ |
| 3.293 | 3-Cl-5-t-C$_4$H$_9$—C$_6$H$_3$—(CH$_2$)$_2$ |
| 3.294 | 2-OCH$_3$—C$_6$H$_4$—(CH$_2$)$_2$ |
| 3.295 | 3-OCH$_3$—C$_6$H$_4$—(CH$_2$)$_2$ |
| 3.296 | 4-OCH$_3$—C$_6$H$_4$—(CH$_2$)$_2$ |
| 3.297 | 2-CH$_3$-3-OCH$_3$—C$_6$H$_3$—(CH$_2$)$_2$ |
| 3.298 | 2-CH$_3$-4-OCH$_3$—C$_6$H$_3$—(CH$_2$)$_2$ |
| 3.299 | 2-CH$_3$-5-OCH$_3$—C$_6$H$_3$—(CH$_2$)$_2$ |
| 3.300 | 3-CH$_3$-5-OCH$_3$—C$_6$H$_3$—(CH$_2$)$_2$ |
| 3.301 | 3-CH$_3$-5-OCH$_3$—C$_6$H$_3$—(CH$_2$)$_2$ |
| 3.302 | 2-Cl-3-OCH$_3$—C$_6$H$_3$—(CH$_2$)$_2$ |
| 3.303 | 2-Cl-4-OCH$_3$—C$_6$H$_3$—(CH$_2$)$_2$ |
| 3.304 | 2-Cl-5-OCH$_3$—C$_6$H$_3$—(CH$_2$)$_2$ |
| 3.305 | 2-OCH$_3$-3-Cl-C$_6$H$_3$—(CH$_3$)$_2$ |

TABLE III-continued

| | |
|---|---|
| 3.306 | 2-OCH$_3$-4-Cl-C$_6$H$_3$—(CH$_3$)$_2$ |
| 3.307 | 2-OCH$_3$-5-Cl-C$_6$H$_3$—(CH$_3$)$_2$ |
| 3.308 | 2-CH$_3$-4-(Cyclohexyl)-C$_6$H$_3$—(CH$_2$)$_2$ |
| 3.309 | 2-CH$_3$-4-C$_6$H$_5$—C$_6$H$_3$—(CH$_2$)$_2$ |
| 3.310 | 2-CH$_3$-3-Br—C$_6$H$_3$—(CH$_2$)$_2$ |
| 3.311 | 2-CH$_3$-4-Br—C$_6$H$_3$—(CH$_2$)$_2$ |
| 3.312 | 3-CH$_3$-5-Br—C$_6$H$_3$—(CH$_2$)$_2$ |
| 3.313 | 2-CH$_3$-3-(Methoxyiminomethyl)-C$_6$H$_3$—(CH$_2$)$_2$ |
| 3.314 | 2-Methoxyiminomethyl-C$_6$H$_4$—(CH$_2$)$_2$ |
| 3.315 | 3-Methoxyiminomethyl-C$_6$H$_4$—(CH$_2$)$_2$ |
| 3.316 | 2-CH$_3$-4-(Methoxyiminomethyl)-C$_6$H$_3$—(CH$_2$)$_2$ |
| 3.317 | 2-Phenyl-C$_6$H$_4$—(CH$_2$)$_2$ |
| 3.318 | 3-Phenyl-C$_6$H$_4$—(CH$_2$)$_2$ |
| 3.319 | 4-Phenyl-C$_6$H$_4$—(CH$_2$)$_2$ |
| 3.320 | 2-Phenoxy-C$_6$H$_4$—(CH$_2$)$_2$ |
| 3.321 | 3-Phenoxy-C$_6$H$_4$—(CH$_2$)$_2$ |
| 3.322 | 4-Phenoxy-C$_6$H$_4$—(CH$_2$)$_2$ |
| 3.323 | 2-Benzyloxy-C$_6$H$_4$—(CH$_2$)$_2$ |
| 3.324 | 2-Benzyloxy-C$_6$H$_4$—(CH$_2$)$_2$ |
| 3.325 | 4-Benzyloxy-C$_6$H$_4$—(CH$_2$)$_2$ |
| 3.326 | 1-Naphthyl-(CH$_2$)$_2$ |
| 3.327 | 2-Naphthyl-(CH$_2$)$_2$ |
| 3.328 | 9-Anthryl-(CH$_2$)$_2$ |
| 3.329 | 2-CH$_3$-3-C$_6$H$_5$O—C$_6$H$_3$—(CH$_2$)$_2$ |
| 3.330 | 2-CH$_3$-4-C$_6$H$_5$O—C$_6$H$_3$—(CH$_2$)$_2$ |
| 3.331 | 2-CH$_3$-5-C$_6$H$_5$O—C$_6$H$_3$—(CH$_2$)$_2$ |
| 3.332 | 3-CH$_3$-4-C$_6$H$_5$O—C$_6$H$_3$—(CH$_2$)$_2$ |
| 3.333 | 4-CH$_3$-5-C$_6$H$_5$O—C$_6$H$_3$—(CH$_2$)$_2$ |
| 3.334 | 2-Cl-3-C$_6$H$_5$O—C$_6$H$_3$—(CH$_2$)$_2$ |
| 3.335 | 2-Cl-4-C$_6$H$_5$O—C$_6$H$_3$—(CH$_2$)$_2$ |
| 3.336 | 2-Cl-5-C$_6$H$_5$O—C$_6$H$_3$—(CH$_2$)$_2$ |
| 3.337 | 3-Cl-4-C$_6$H$_5$O—C$_6$H$_3$—(CH$_2$)$_2$ |
| 3.338 | 3-Cl-5-C$_6$H$_5$O—C$_6$H$_3$—(CH$_2$)$_2$ |
| 3.339 | 2-CH$_3$-4-COCH$_3$—C$_6$H$_3$—(CH$_2$)$_2$ |
| 3.340 | 2-CH$_3$-4-COCH$_3$—C$_6$H$_3$—(CH$_2$)$_2$ |
| 3.341 | C$_6$H$_5$—CH=CH—CH$_2$ |
| 3.342 | 2-F-C$_6$H$_4$—CH=CH—CH$_2$ |
| 3.343 | 2-F-C$_6$H$_4$—CH=CH—CH$_2$ |
| 3.344 | 4-F-C$_6$H$_4$—CH=CH—CH$_2$ |
| 3.345 | 2-Cl-C$_6$H$_4$—CH=CH—CH$_2$ |
| 3.346 | 3-Cl-C$_6$H$_4$—CH=CH—CH$_2$ |
| 3.347 | 4-Cl-C$_6$H$_4$—CH=CH—CH$_2$ |
| 3.348 | 2,3-Cl$_2$—C$_6$H$_3$—CH=CH—CH$_2$ |
| 3.349 | 2,4-Cl$_2$—C$_6$H$_3$—CH=CH—CH$_2$ |
| 3.350 | 2,5-Cl$_2$—C$_6$H$_3$—CH=CH—CH$_2$ |
| 3.351 | 2,6-Cl$_2$—C$_6$H$_3$—CH=CH—CH$_2$ |
| 3.352 | 3,4-Cl$_2$—C$_6$H$_3$—CH=CH—CH$_2$ |
| 3.353 | 2-CH$_3$—C$_6$H$_4$—CH=CH—CH$_2$ |
| 3.354 | 3-CH$_3$—C$_6$H$_4$—CH=CH—CH$_2$ |
| 3.355 | 4-CH$_3$—C$_6$H$_4$—CH=CH—CH$_2$ |
| 3.356 | 2,3-(CH$_3$)$_2$—C$_6$H$_3$—CH=CH—CH$_2$ |
| 3.357 | 2,4-(CH$_3$)$_2$—C$_6$H$_3$—CH=CH—CH$_2$ |
| 3.358 | 2,5-(CH$_3$)$_2$—C$_6$H$_3$—CH=CH—CH$_2$ |
| 3.359 | 3,4-(CH$_3$)$_2$—C$_6$H$_3$—CH=CH—CH$_2$ |
| 3.360 | 3,5-(CH$_3$)$_2$—C$_6$H$_3$—CH=CH—CH$_2$ |
| 3.361 | 4,5-(CH$_3$)$_2$—C$_6$H$_3$—CH=CH—CH$_2$ |
| 3.362 | 2,3,4-(CH$_3$)$_3$—C$_6$H$_2$—CH=CH—CH$_2$ |
| 3.363 | 2,4,5-(CH$_3$)$_3$—C$_6$H$_2$—CH=CH—CH$_2$ |
| 3.364 | 2,4,6-(CH$_3$)$_3$—C$_6$H$_2$—CH=CH—CH$_2$ |
| 3.365 | 2,3,6-(CH$_3$)$_3$—C$_6$H$_2$—CH=CH—CH$_2$ |
| 3.366 | 2-CF$_3$—C$_6$H$_4$—CH=CH—CH$_2$ |
| 3.367 | 3-CF$_3$—C$_6$H$_4$—CH=CH—CH$_2$ |
| 3.368 | 4-CF$_3$—C$_6$H$_4$—CH=CH—CH$_2$ |
| 3.369 | 2-CH$_3$-3-CF$_3$—C$_6$H$_3$—CH=CH—CH$_2$ |
| 3.370 | 2-CH$_3$-4-CF$_3$—C$_6$H$_3$—CH=CH—CH$_2$ |
| 3.371 | 2-CF$_3$-3-CH$_3$—C$_6$H$_3$—CH=CH—CH$_2$ |
| 3.372 | 2-CF$_3$-4-CH$_3$—C$_6$H$_3$—CH=CH—CH$_2$ |
| 3.373 | 2-CF$_3$-5-CH$_3$—C$_6$H$_3$—CH=CH—CH$_2$ |
| 3.374 | 2-CH$_3$-5-CF$_3$—C$_6$H$_3$—CH=CH—CH$_2$ |
| 3.375 | C$_6$H$_5$—(CH$_2$)$_3$ |
| 3.376 | C$_6$H$_5$—(CH$_2$)$_4$ |
| 3.377 | C$_6$H$_5$—CH$_2$CH=CH—CH$_2$ |
| 3.378 | 4-F-C$_6$H$_4$—CH=CH—(CH$_2$)$_2$ |
| 3.379 | CH$_3$O—CO—CH$_2$ |
| 3.380 | CH$_3$CH$_2$O—CO—CH$_2$ |
| 3.381 | CH$_3$—CO—CH$_2$—CH$_2$ |
| 3.382 | t-C$_4$H$_9$O—CO—(CH$_2$)$_3$ |
| 3.383 | t-C$_4$H$_9$O—CO—(CH$_2$)$_2$ |
| 3.384 | t-C$_4$H$_9$O—CO—CH$_2$ |
| 3.385 | n-C$_4$H$_9$O—CO—CH$_2$ |
| 3.386 | iso-C$_4$H$_9$O—CO—CH$_2$ |
| 3.387 | n-C$_3$H$_7$O—CO—CH$_2$ |

TABLE III-continued
| | |
|---|---|
| 3.388 | sec.-C$_4$H$_9$O—CO—CH$_2$ |
| 3.389 | C$_6$H$_5$—CO—CH$_2$ |
| 3.390 | 2-CH$_3$—C$_6$H$_4$O—CO—CH$_2$ |
| 3.391 | 3-CH$_3$—C$_6$H$_4$O—CO—CH$_2$ |
| 3.392 | 4-CH$_3$—C$_6$H$_4$O—CO—CH$_2$ |
| 3.393 | 2-Cl—C$_6$H$_4$O—CO—CH$_2$ |
| 3.394 | 3-Cl—C$_6$H$_4$O—CO—CH$_2$ |
| 3.395 | 4-Cl—C$_6$H$_4$O—CO—CH$_2$ |
| 3.396 | C$_6$H$_5$—C(CH$_3$)=CH—CH$_2$ |
| 3.397 | 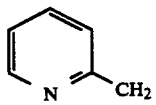 |
| 3.398 | 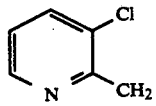 |
| 3.399 | 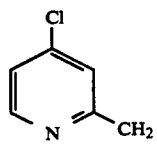 |
| 3.400 | 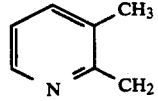 |
| 3.401 | 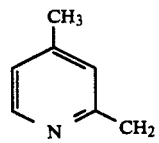 |
| 3.402 | 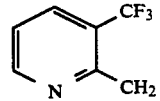 |
| 3.403 | 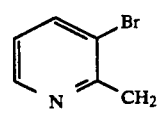 |
| 3.404 | 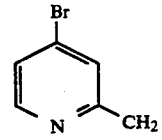 |
| 3.405 | 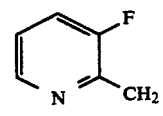 |
| 3.406 | 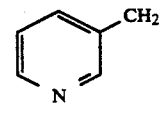 |
| 3.407 | 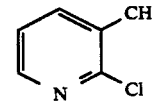 |

TABLE III-continued
| | |
|---|---|
| 3.408 | 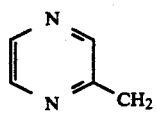 |
| 3.409 | 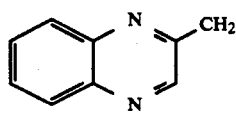 |
| 3.410 | 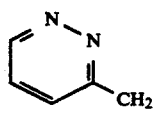 |
| 3.411 | 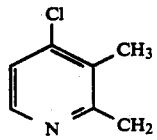 |
| 3.412 | 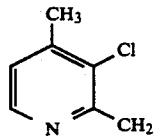 |
| 3.413 | 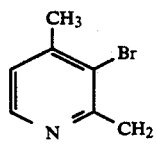 |
| 3.414 | 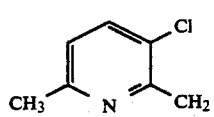 |
| 3.415 | 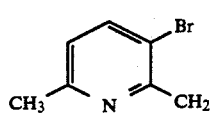 |
| 3.416 | 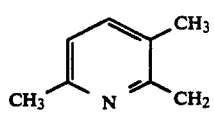 |
| 3.417 | 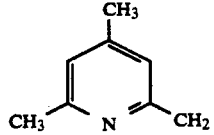 |
| 3.418 | 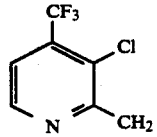 |
| 3.419 | 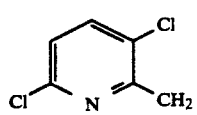 |

TABLE III-continued
| | |
|---|---|
| 3.420 | 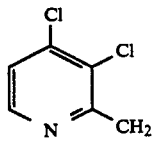 |
| 3.421 | 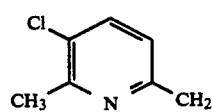 |
| 3.422 | 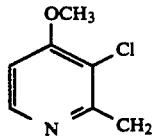 |
| 3.423 | 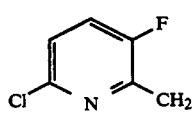 |
| 3.424 | 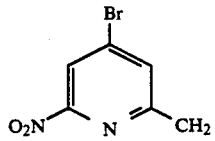 |
| 3.425 | 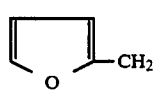 |
| 3.426 | 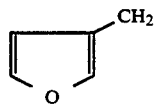 |
| 3.427 | 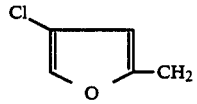 |
| 3.428 | 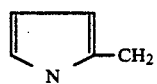 |
| 3.429 | 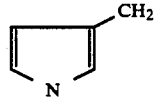 |
| 3.430 | 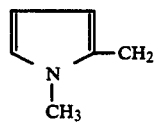 |
| 3.431 | 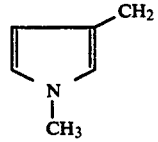 |
| 3.432 | 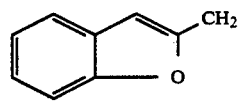 |

TABLE III-continued
3.433 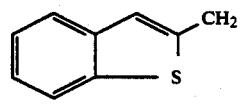
3.434 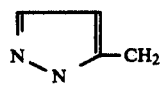
3.435 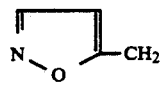
3.436 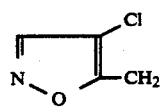
3.437 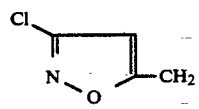
3.438 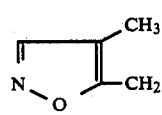
3.439 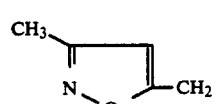
3.440 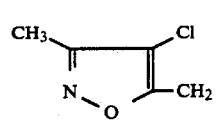
3.441 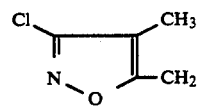
3.442 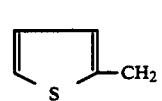
3.443 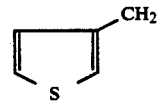
3.444 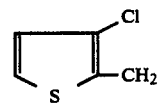
3.445 
3.446 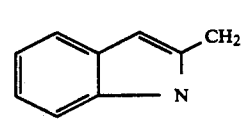

TABLE III-continued
| | |
|---|---|
| 3.447 | 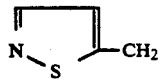 |
| 3.448 | 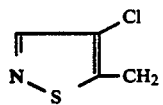 |
| 3.449 | 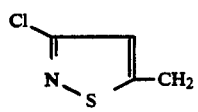 |
| 3.450 | 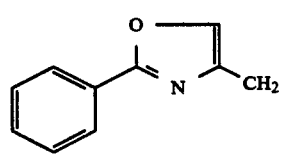 |
| 3.451 | 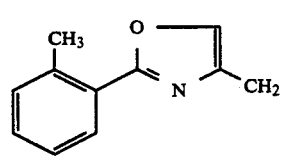 |
| 3.452 | 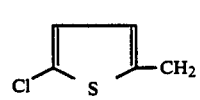 |
| 3.453 | 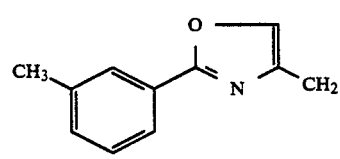 |
| 3.454 | 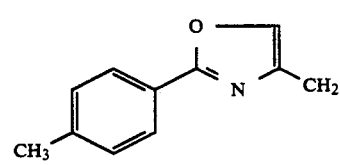 |
| 3.455 | 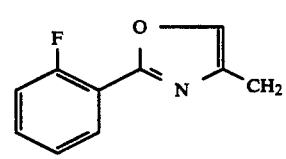 |
| 3.456 | 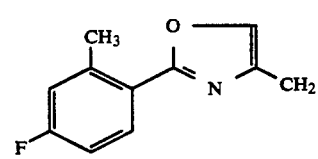 |
| 3.457 | 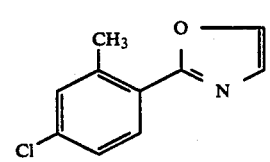 |

TABLE III-continued

| | |
|---|---|
| 3.458 | 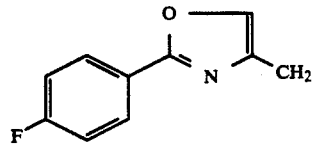 |
| 3.459 | 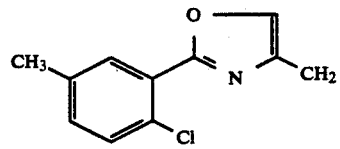 |
| 3.460 | 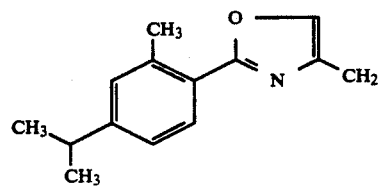 |
| 3.461 | 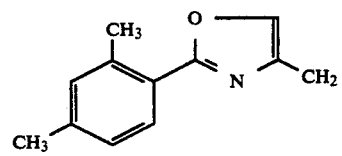 |
| 3.462 | N≡C—CH$_2$ |
| 3.463 | t-BuO—CH$_2$—CH=CH—CH$_2$ |
| 3.464 | (CH$_3$)$_2$—C=CH—CH$_2$—CH$_2$—C=CH—CH$_3$<br>　　　　　　　　　　　　　　　　　　CH$_3$ |

TABLE IV

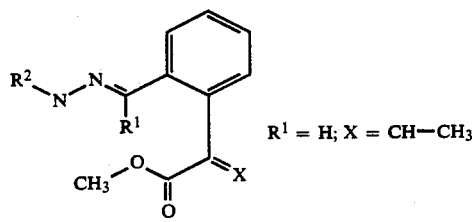

$R^1 = H$; $X = CH—CH_3$

| Comp. no. | $R^2$ | IR (cm$^{-1}$) |
|---|---|---|
| 4.1 | Methyl | |
| 4.2 | Ethyl | |
| 4.3 | n-Propyl | |
| 4.4 | iso-Propyl | |
| 4.5 | n-Butyl | |
| 4.6 | iso-Butyl | |
| 4.7 | sec.-Butyl | |
| 4.8 | tert.-Butyl | |
| 4.9 | n-Hexyl | |
| 4.10 | n-Decyl | |
| 4.11 | Cyclopropyl | |
| 4.12 | Cyclohexyl | |
| 4.13 | 1-Methylcyclopropyl | |
| 4.14 | 1-Methylcyclohexyl | |
| 4.15 | Ethenyl | |
| 4.16 | 1-Propenyl | |
| 4.17 | 2-Methyl-1-propenyl | |
| 4.18 | 2-Propenyl | |
| 4.19 | 2-Butenyl | |
| 4.20 | Phenyl | |
| 4.22 | 3-Fluorophenyl | |
| 4.23 | 4-Fluorophenyl | |
| 4.24 | 2-Chlorophenyl | |
| 4.25 | 3-Chlorophenyl | |

TABLE IV-continued

| | |
|---|---|
| 4.26 | 4-Chlorophenyl |
| 4.27 | Pentachlorophenyl |
| 4.28 | 2,3-Dichlorophenyl |
| 4.29 | 2,4-Dichlorophenyl |
| 4.30 | 2,5-Dichlorophenyl |
| 4.31 | 2,6-Dichlorophenyl |
| 4.32 | 3,4-Dichlorophenyl |
| 4.33 | 3,5-Dichlorophenyl |
| 4.34 | 2,3,4-Trichlorophenyl |
| 4.35 | 2,3,5-Trichlorophenyl |
| 4.36 | 2,3,6-Trichlorophenyl |
| 4.37 | 2,4,5-Trichlorophenyl |
| 4.38 | 2,4,6-Trichlorophenyl |
| 4.39 | 3,4,5-Trichlorophenyl |
| 4.40 | 2,3,4,5-Tetrachlorophenyl |
| 4.41 | 2,3,4,6-Tetrachlorophenyl |
| 4.42 | 2-Bromophenyl |
| 4.43 | 3-Bromophenyl |
| 4.44 | 4-Bromophenyl |
| 4.45 | 2,4-Dibromophenyl |
| 4.46 | 3-Bromo-4-Fluorophenyl |
| 4.47 | 3-Bromo-4-Methoxyphenyl |
| 4.48 | 2-Iodophenyl |
| 4.49 | 3-Iodophenyl |
| 4.50 | 4-Iodophenyl |
| 4.51 | 2-Chloro-4-Fluorophenyl |
| 4.52 | 2-Chloro-5-Fluorophenyl |
| 4.53 | 2-Chloro-6-Fluorophenyl |
| 4.54 | 2-Chloro-4-Bromophenyl |
| 4.55 | 2-Bromo-4-Chlorophenyl |
| 4.56 | 2-Bromo-4-Fluorophenyl |
| 4.57 | 3-Bromo-4-Chlorophenyl |
| 4.58 | 3-Chloro-4-Fluorophenyl |
| 4.59 | 3-Fluoro-4-Chlorophenyl |
| 4.60 | 2-Cyanophenyl |
| 4.61 | 3-Cyanophenyl |
| 4.62 | 4-Cyanophenyl |
| 4.63 | 2-Nitrophenyl |
| 4.64 | 3-Nitrophenyl |
| 4.65 | 4-Nitrophenyl |
| 4.66 | 2-Methylphenyl |
| 4.67 | 3-Methylphenyl |
| 4.68 | 4-Methylphenyl |
| 4.69 | 2,4-Dimethylphenyl |
| 4.70 | 2,6-Dimethylphenyl |
| 4.71 | 3,4-Dimethylphenyl |
| 4.72 | 3,5-Dimethylphenyl |
| 4.73 | 2,3,4-Trimethylphenyl |
| 4.74 | 2,3,5-Trimethylphenyl |
| 4.75 | 2,3,6-Trimethylphenyl |
| 4.76 | 2,4,5-Trimethylphenyl |
| 4.77 | 2,4,6-Trimethylphenyl |
| 4.78 | 3,4,5-Trimethylphenyl |
| 4.79 | Pentamethylphenyl |
| 4.80 | 2-Methyl-5-Methoxyphenyl |
| 4.81 | 2-Methyl-6-Methoxyphenyl |
| 4.82 | 2-Methyl-4-iso-Propoxyphenyl |
| 4.83 | 2-Methyl-2,5-Dimethoxyphenyl |
| 4.84 | 2-Methoxyphenyl |
| 4.85 | 3-Methoxyphenyl |
| 4.86 | 4-Methoxyphenyl |
| 4.87 | 2,3-Dimethoxyphenyl |
| 4.88 | 2,4-Dimethoxyphenyl |
| 4.89 | 2,5-Dimethoxyphenyl |
| 4.90 | 2,6-Dimethoxyphenyl |
| 4.91 | 3,4-Dimethoxyphenyl |
| 4.92 | 3,5-Dimethoxyphenyl |
| 4.93 | 3,6-Dimethoxyphenyl |
| 4.94 | 2,3,4-Trimethoxyphenyl |
| 4.95 | 2,3,5-Trimethoxyphenyl |
| 4.96 | 2,3,6-Trimethoxyphenyl |
| 4.97 | 2,4,5-Trimethoxyphenyl |
| 4.98 | 2,4,6-Trimethoxyphenyl |
| 4.99 | 3,4,5-Trimethoxyphenyl |
| 4.100 | 2-Ethoxyphenyl |
| 4.101 | 3-Ethoxyphenyl |
| 4.102 | 4-Ethoxyphenyl |
| 4.103 | 2-iso-Propoxyphenyl |
| 4.104 | 3-iso-Propoxyphenyl |
| 4.105 | 2-Phenylphenyl |
| 4.106 | 3-Phenylphenyl |
| 4.107 | 4-Phenylphenyl |

TABLE IV-continued

| | |
|---|---|
| 4.108 | 2-Phenoxyphenyl |
| 4.109 | 3-Phenoxyphenyl |
| 4.110 | 4-Phenoxyphenyl |
| 4.111 | 2-Benzyloxyphenyl |
| 4.112 | 3-Benzyloxyphenyl |
| 4.113 | 4-Benzyloxyphenyl |
| 4.114 | 4-(Imidazol-1'-yl)phenyl |
| 4.115 | 4-(Piperazin-1'yl)phenyl |
| 4.116 | 4-(Morpholino-1'-yl)phenyl |
| 4.117 | 4-(Piperidinyl-1'-yl)phenyl |
| 4.118 | 4-(Pyridyl-2'-oxy)phenyl |
| 4.119 | 2-Cyclopropylphenyl |
| 4.120 | 3-Cyclopropylphenyl |
| 4.121 | 4-Cyclopropylphenyl |
| 4.122 | 3-Cyclohexylphenyl |
| 4.123 | 4-Cyclohexylphenyl |
| 4.124 | 4-Oxiranylphenyl |
| 4.125 | 4-iso-Propoxyphenyl |
| 4.126 | 3-tert.-Butoxyphenyl |
| 4.127 | 4-tert.-Butoxyphenyl |
| 4.128 | 2-Trifluoromethoxyphenyl |
| 4.129 | 3-Trifluoromethoxyphenyl |
| 4.130 | 4-Trifluoromethoxymethyl |
| 4.131 | 2-Chloromethylphenyl |
| 4.132 | 3-Chloromethylphenyl |
| 4.133 | 4-Chloromethylphenyl |
| 4.134 | 2-Trifluoromethylphenyl |
| 4.135 | 3-Trifluoromethylphenyl |
| 4.136 | 4-Trifluoromethylphenyl |
| 4.137 | 2-(Methoxyiminomethyl)phenyl |
| 4.138 | 3-(Methoxyiminomethyl)phenyl |
| 4.139 | 4-(Methoxyiminomethyl)phenyl |
| 4.140 | 2-(Ethoxyiminomethyl)phenyl |
| 4.141 | 3-(Ethoxyiminomethyl)phenyl |
| 4.142 | 4-(Ethoxyiminomethyl)phenyl |
| 4.143 | 2-(n-Propoxyiminomethyl)phenyl |
| 4.144 | 3-(n-Propoxyiminomethyl)phenyl |
| 4.145 | 4-(n-Propoxyiminomethyl)phenyl |
| 4.146 | 2-(iso-Propoxyiminomethyl)phenyl |
| 4.147 | 3-(iso-Propoxyiminomethyl)phenyl |
| 4.148 | 2-(Ethoxyimino-1'-ethyl)phenyl |
| 4.149 | 3-(Ethoxyimino-1'-ethyl)phenyl |
| 4.150 | 4-(Ethoxyimino-1'-ethyl)phenyl |
| 4.151 | 2-(n-Propoxyimino-1'-ethyl)phenyl |
| 4.152 | 3-(n-Propoxyimino-1'-ethyl)phenyl |
| 4.153 | 4-(n-Propoxyimino-1'-ethyl)phenyl |
| 4.154 | 2-(n-Butoxyamino-1'-ethyl)phenyl |
| 4.155 | 3-(n-Butoxyamino-1'-ethyl)phenyl |
| 4.156 | 4-(n-Butoxyamino-1'-ethyl)phenyl |
| 4.157 | 2-(n-Pentoxyimino-1'-ethyl)phenyl |
| 4.158 | 3-(n-Pentoxyimino-1'-ethyl)phenyl |
| 4.159 | 4-(n-Pentoxyimino-1'-ethyl)phenyl |
| 4.160 | 2-(n-Hexoxyimino-1'-ethyl)phenyl |
| 4.161 | 3-(n-Hexoxyimino-1'-ethyl)phenyl |
| 4.162 | 4-(n-Hexoxyimino-1'-ethyl)phenyl |
| 4.163 | 2-(Allyloxyimino-1'-ethyl)phenyl |
| 4.164 | 3-(Allyloxyimino-1'-ethyl)phenyl |
| 4.165 | 4-(Allyloxyimino-1'-ethyl)phenyl |
| 4.166 | 2-(Benzyloxyimino-1'-ethyl)phenyl |
| 4.167 | 3-(Benzyloxyimino-1'-ethyl)phenyl |
| 4.168 | 4-(Benzyloxyimino-1'-ethyl)phenyl |
| 4.169 | 2-(2-Fluorophenyl)phenyl |
| 4.170 | 2-(2-Chlorophenyl)phenyl |
| 4.171 | 2-(2-Methylphenyl)phenyl |
| 4.172 | 2-(2-Methoxyphenyl)phenyl |
| 4.173 | 4-(iso-Propoxyiminomethyl)phenyl |
| 4.174 | 2-(n-Butoxyiminomethyl)phenyl |
| 4.175 | 3-(n-Butoxyiminomethyl)phenyl |
| 4.176 | 4-(n-Butoxyiminomethyl)phenyl |
| 4.177 | 2-(iso-Butoxyiminomethyl)phenyl |
| 4.178 | 3-(iso-Butoxyiminomethyl)phenyl |
| 4.179 | 4-(iso-Butoxyiminomethyl)phenyl |
| 4.180 | 2-(tert.-Butoxyiminomethyl)phenyl |
| 4.181 | 3-(tert.-Butoxyiminomethyl)phenyl |
| 4.182 | 4-(tert.-Butoxyiminomethyl)phenyl |
| 4.183 | 2-(n-Pentoxyiminomethyl)phenyl |
| 4.184 | 3-(n-Pentoxyiminomethyl)phenyl |
| 4.185 | 4-(n-Pentoxyiminomethyl)phenyl |
| 4.186 | 2-(n-Hexoxyiminomethyl)phenyl |
| 4.187 | 3-(n-Hexoxyiminomethyl)phenyl |
| 4.188 | 4-(n-Hexoxyiminomethyl)phenyl |
| 4.189 | 2-(Allyloxyiminomethyl)phenyl |

TABLE IV-continued

| | |
|---|---|
| 4.190 | 3-(Allyloxyiminomethyl)phenyl |
| 4.191 | 4-(Allyloxyiminomethyl)phenyl |
| 4.192 | 2-(Benzyloxyiminomethyl)phenyl |
| 4.193 | 3-(Benzyloxyiminomethyl)phenyl |
| 4.194 | 4-(Benzyloxyiminomethyl)phenyl |
| 4.195 | 2-(Methoxyimino-1'-ethyl)phenyl |
| 4.196 | 3-(Methoxyimino-1'-ethyl)phenyl |
| 4.197 | 4-(Methoxyimino-1'-ethyl)phenyl |
| 4.198 | 3-Phenoxyphenyl |
| 4.199 | 4-Phenoxyphenyl |
| 4.200 | 2-Benzyloxyphenyl |
| 4.201 | 3-Benzyloxyphenyl |
| 4.202 | 4-Benzyloxyphenyl |
| 4.203 | 4-(Imidazol-1'-yl)phenyl |
| 4.204 | 4-(Piperazin-1'-yl)phenyl |
| 4.205 | 4-(Morpholin-1'-yl)phenyl |
| 4.206 | 4-(Piperidin-1'-yl)phenyl |
| 4.207 | 4-Pyridyl-2'-oxy)phenyl |
| 4.208 | 2-Cyclopropylphenyl |
| 4.209 | 3-Cyclopropylphenyl |
| 4.210 | 4-Cyclopropylphenyl |
| 4.211 | 3-Cyclohexylphenyl |
| 4.212 | 4-Cyclohexylphenyl |
| 4.213 | 4-Oxiranylphenyl |
| 4.214 | 6-F-Pyridin-3-yl |
| 4.215 | 6-Cl-Pyridin-3-yl |
| 4.216 | 6-Br-Pyridin-3-yl |
| 4.217 | 6-$CH_3$-Pyridin-3-yl |
| 4.218 | 6-$CF_3$-Pyridin-3-yl |
| 4.219 | 6-$CH_3O$-Pyridin-3-yl |
| 4.220 | 2-F-Pyridin-4-yl |
| 4.221 | 2-Cl-Pyridin-4-yl |
| 4.222 | 2-Br-Pyridin-4-yl |
| 4.223 | 2-$CH_3$-Pyridin-4-yl |
| 4.224 | 2-$CF_3$-Pyridin-4-yl |
| 4.225 | 2-$CH_3O$-Pyridin-4-yl |
| 4.226 | 3-F-Pyridin-4-yl |
| 4.227 | 3-Cl-Pyridin-4-yl |
| 4.228 | 3-Br-Pyridin-4-yl |
| 4.229 | 3-$CH_3$-Pyridin-4-yl |
| 4.230 | 3-$CF_3$-Pyridin-4-yl |
| 4.231 | 3-$CH_3O$-Pyridin-3-yl |
| 4.232 | 5-F-Pyridin-4-yl |
| 4.233 | 5-Cl-Pyridin-4-yl |
| 4.234 | 5-Br-Pyridin-4-yl |
| 4.235 | 5-$CH_3$-Pyridin-4-yl |
| 4.236 | 5-$CF_3$-Pyridin-4-yl |
| 4.237 | 5-$CH_3O$-Pyridin-4-yl |
| 4.238 | 6-F-Pyridin-4-yl |
| 4.239 | 6-Cl-Pyridin-4-yl |
| 4.240 | 6-Br-Pyridin-4-yl |
| 4.241 | 6-$CH_3$-Pyridin-4-yl |
| 4.242 | 6-$CF_3$-Pyridin-4-yl |
| 4.243 | 6-$CH_3O$-Pyridin-4-yl |
| 4.244 | 2-F-Pyridin-5-yl |
| 4.245 | 2-Cl-Pyridin-5-yl |
| 4.246 | 2-Br-Pyridin-5-yl |
| 4.247 | 2-$CH_3$-Pyridin-5-yl |
| 4.248 | 2-$CF_3$-Pyridin-5-y |
| 4.249 | 2-$CH_3O$-Pyridin-5-yl |
| 4.250 | 4-F-Pyridin-5-yl |
| 4.251 | 4-Cl-Pyridin-5-yl |
| 4.252 | 4-Br-Pyridin-5-yl |
| 4.253 | 4-$CH_3$-Pyridin-5-yl |
| 4.254 | 4-$CF_3$-Pyridin-5-yl |
| 4.255 | 4-$CH_3O$-Pyridin-5-yl |
| 4.256 | 3-F-Pyridin-2-yl |
| 4.257 | 3-Cl-Pyridin-2-yl |
| 4.258 | 3-Br-Pyridin-2-yl |
| 4.259 | 3-$CH_3$-Pyridin-2-yl |
| 4.260 | 3-$CF_3$-Pyridin-2-yl |
| 4.261 | 3-$CH_3O$-Pyridin-2-yl |
| 4.262 | 4-F-Pyridin-2-yl |
| 4.263 | 4-Br-Pyridin-2-yl |
| 4.264 | 4-$CF_3$-Pyridin-2-yl |
| 4.265 | 4-$CH_3O$-Pyridin-2-yl |
| 4.266 | 5-F-Pyridin-2-yl |
| 4.267 | 5-Cl-Pyridin-2-yl |
| 4.268 | 5-Br-Pyridin-2-yl |
| 4.269 | 5-$CF_3$-Pyridin-2-yl |
| 4.270 | 5-$CH_3$-Pyridin-2-yl |
| 4.271 | 5-$CH_3O$-Pyridin-2-yl |

TABLE IV-continued

| | |
|---|---|
| 4.272 | 6-F-Pyridin-2-yl |
| 4.273 | 6-Cl-Pyridin-2-yl |
| 4.274 | 6-Br-Pyridin-2-yl |
| 4.275 | 6-CH$_3$-Pyridin-2-yl |
| 4.276 | 6-CF$_3$-Pyridin-2-yl |
| 4.277 | 6-CH$_3$O-Pyridin-2-yl |
| 4.278 | 2-F-Pyridin-3-yl |
| 4.279 | 4-Cl-Pyridin-2-yl |
| 4.280 | 2-Br-Pyridin-3-yl |
| 4.281 | 2-CH$_3$-Pyridin-3-yl |
| 4.282 | 2-CF$_3$-Pyridin-3-yl |
| 4.283 | 2-CH$_3$O-Pyridin-3-yl |
| 4.284 | 4-F-Pyridin-3-yl |
| 4.285 | 4-Cl-Pyridin-3-yl |
| 4.286 | 4-Br-Pyridin-3-yl |
| 4.287 | 4-CH$_3$-Pyridin-3-yl |
| 4.288 | 4-CF$_3$-Pyridin-3-yl |
| 4.289 | 4-CH$_3$O-Pyridin-3-yl |
| 4.290 | 5-F-Pyridin-3-yl |
| 4.291 | 5-Cl-Pyridin-3-yl |
| 4.292 | 5-Br-Pyridin-3-yl |
| 4.293 | 5-CH$_3$-Pyridin-3-yl |
| 4.294 | 5-CF$_3$-Pyridin-3-yl |
| 4.295 | 5-CH$_3$O-Pyridin-3-yl |
| 4.296 | 3-F-5-CF$_3$-Pyridin-2-yl |
| 4.297 | 3,6-Cl$_2$-5-CF$_3$-Pyridin-2-yl |
| 4.298 | 6-Cl-4-CN-Pyridin-2-yl |
| 4.299 | 3-CN-5-NO$_2$-Pyridin-2-yl |
| 4.300 | 2-Cl-6-F-Pyridin-2-yl |
| 4.301 | 6-Cl-4-F-Pyridin-2-yl |
| 4.302 | 4,6-F$_2$-Pyridin-2-yl |
| 4.303 | 3,5-Cl$_2$-6-F-Pyridin-2-yl |
| 4.304 | 6-CH$_3$O-3-NO$_2$-Pyridin-2-yl |
| 4.305 | 4-CN-6-F-Pyridin-2-yl |
| 4.306 | 6-Cl-5-CN-Pyridin-2-yl |
| 4.307 | 6-Cl-3-CN-Pyridin-2-yl |
| 4.308 | 6-Cl-5-NO$_2$-Pyridin-2-yl |
| 4.309 | 6-Cl-3-NO$_2$-Pyridin-2-yl |
| 4.310 | 5-CN-6-F-Pyridin-2-yl |
| 4.311 | 3-CN-6-F-Pyridin-2-yl |
| 4.312 | 4,6-(CN)$_2$-Pyridin-2-yl |
| 4.313 | 5-Br-4-CF$_3$-Pyridin-2-yl |
| 4.314 | 3-NO$_2$-5-CF$_3$-Pyridin-2-yl |
| 4.315 | 5-NH$_2$-Pyridin-2-yl |
| 4.316 | 5-NO$_2$-Pyridin-2-yl |
| 4.317 | 4-CH$_3$-5-NO$_2$-Pyridin-2-yl |
| 4.318 | 2,6-Cl$_2$-Pyridin-4-yl |
| 4.319 | 5-(CH$_3$OCO)-Pyridin-2-yl |
| 4.320 | 5-Cl-6-F-Pyridin-2-yl |
| 4.321 | 5-Cl-6-OH-Pyridin-2-yl |
| 4.322 | 5-Cl-6-CH$_3$O-Pyridin-2-yl |
| 4.323 | 5-Cl-6-CN-Pyridin-2-yl |
| 4.324 | 5,6-Cl$_2$-Pyridin-2-yl |
| 4.325 | 6-Br-5-Cl-Pyridin-2-yl |
| 4.326 | 5-Br-6-F-Pyridin-2-yl |
| 4.327 | 5-Br-6-Cl-Pyridin-2-yl |
| 4.328 | 5-Br-6-CN-Pyridin-2-yl |
| 4.329 | 5-Br-6-OH-Pyridin-2-yl |
| 4.330 | 5-Br-6-CH$_3$O-Pyridin-2-yl |
| 4.331 | 4-CN-Pyridin-2-yl |
| 4.332 | 6-CN-Pyridin-2-yl |
| 4.333 | 5-Cl-Pyridin-2-yl |
| 4.334 | 5-F-Pyridin-2-yl |
| 4.335 | 5-CF$_3$-1,3,4-Thiadiazol-2-yl |
| 4.336 | 4-Cl-1,2,5-Thiadiazol-3-yl |
| 4.337 | 4-Cl-Pyrimidin-2-yl |
| 4.338 | 4-Br-Pyrimidin-2-yl |
| 4.339 | 4-F-Pyrimidin-2-yl |
| 4.340 | 4-CH$_3$-Pyrimidin-2-yl |
| 4.341 | 4-CH$_3$O-Pyrimidin-2-yl |
| 4.342 | 4-CH$_3$CH$_2$O-Pyrimidin-2-yl |
| 4.343 | 4-NO$_2$-Pyrimidin-2-yl |
| 4.344 | 4-CN-Pyrimidin-2-yl |
| 4.345 | 4-CF$_3$-Pyrimidin-2-yl |
| 4.346 | 4-C$_6$H$_5$-Pyrimidin-2-yl |
| 4.347 | 4-C$_6$H$_5$O-Pyrimidin-2-yl |
| 4.348 | 5-F-Pyrimidin-2-yl |
| 4.349 | 5-CH$_3$-Pyrimidin-2-yl |
| 4.350 | 5-CH$_3$O-Pyrimidin-2-yl |
| 4.351 | 5-CH$_3$CH$_2$O-Pyrimidin-2-yl |
| 4.352 | 5-NO$_2$-Pyrimidin-2-yl |
| 4.353 | 5-CN-Pyrimidin-2-yl |

TABLE IV-continued

| | | |
|---|---|---|
| 4.354 | 5-CF₃-Pyrimidin-2-yl | |
| 4.355 | 5-C₆H₅-Pyrimidin-2-yl | |
| 4.356 | 5-C₆H₅O-Pyrimidin-2-yl | |
| 4.357 | 4,5-Cl₂-Pyrimidin-2-yl | |
| 4.358 | 4,6-Cl₂-Pyrimidin-2-yl | |
| 4.359 | 4-Cl-5-CH₃O-Pyrimidin-2-yl | |
| 4.360 | 2-F-Pyrimidin-4-yl | |
| 4.361 | 2-Cl-Pyrimidin-4-yl | |
| 4.362 | 2-F-Pyrimidin-4-yl | |
| 4.363 | 2-Br-Pyrimidin-4-yl | |
| 4.364 | 2-CH₃-Pyrimidin-4-yl | |
| 4.365 | 2-CH₃O-Pyrimidin-4-yl | |
| 4.366 | 2-CH₃CH₂O-Pyrimidin-4-yl | |
| 4.367 | 2-NO₂-Pyrimidin-4-yl | |
| 4.368 | 2-CH₃S-Pyrimidin-4-yl | |
| 4.369 | 2-Cyano-Pyrimidin-4-yl | |
| 4.370 | 2-CF₃-Pyrimidin-4-yl | |
| 4.371 | 2-C₆H₅O-Pyrimidin-4-yl | |
| 4.372 | 2-C₆H₅-Pyrimidin-4-yl | |
| 4.373 | 6-NO₂-Pyrimidin-4-yl | |
| 4.374 | 6-Cyano-Pyrimidin-4-yl | |
| 4.375 | 6-CF₃-Pyrimidin-4-yl | |
| 4.376 | 6-C₆H₅O-Pyrimidin-4-yl | |
| 4.377 | 6-C₆H₅-Pyrimidin-4-yl | |
| 4.378 | 5-F-Pyrimidin-4-yl | |
| 4.379 | 5-Cl-Pyrimidin-4-yl | |
| 4.380 | 5-Br-Pyrimidin-4-yl | |
| 4.381 | 5-CH₃-Pyrimidin-4-yl | |
| 4.382 | 5-CH₃O-Pyrimidin-4-yl | |
| 4.383 | 5-CH₃—CH₂O-Pyrimidin-4-yl | |
| 4.384 | 5-NO₂-Pyrimidin-4-yl | |
| 4.385 | 5-Cyano-Pyrimidin-4-yl | |
| 4.386 | 5-CF₃-Pyrimidin-4-yl | |
| 4.387 | 5-C₆H₅O-Pyrimidin-4-yl | |
| 4.388 | 5-C₆H₅-Pyrimidin-4-yl | |
| 4.389 | 2-Cl-Pyrimidin-5-yl | |
| 4.390 | 2-CH₃-Pyrimidin-5-yl | |
| 4.391 | 2-F-Pyrimidin-5-yl | |
| 4.392 | 2-CH₃O-Pyrimidin-5-yl | |
| 4.393 | 2-Cyano-Pyrimidin-5-yl | |
| 4.394 | 4-CH₃-Pyrimidin-5-yl | |
| 4.395 | 4-CH₃O-Pyrimidin-5-yl | |
| 4.396 | 4-CF₃-Pyrimidin-5-yl | |
| 4.397 | 2,4-(CH₃)₂-Pyrimidin-5-yl | |
| 4.398 | 2-CH₃S-4-CH₃O-Pyrimidin-5-yl | |
| 4.399 | Pyrrol-2-yl-6-Cl-3-NO₂-Pyridin-2-yl | |
| 4.400 | 6-Cl-3-NO₂-Pyridin-2-yl | |
| 4.401 | 6-Cl-5-NO₂-Pyridin-2-yl | |
| 4.402 | 3,6-(CH₃)₂-Pyrazin-2-yl | |
| 4.403 | 6-F-Pyrimidin-4-yl | |
| 4.404 | 6-Br-Pyrimidin-4-yl | |
| 4.405 | 6-CH₃-Pyrimidin-4-yl | |
| 4.406 | 6-CH₃O-Pyrimidin-4-yl | |
| 4.407 | 6-CH₃CH₂O-Pyrimidin-4-yl | |
| 4.408 | 4,6-(CH₃)₂-Pyrimidin-2-yl | 1745, 1594, 1561, 1459, 1446, 1337, 1331, 1210, 1067, 1011 |
| 4.409 | 2-CH₃S-6-CH₃-Pyrimidin-4-yl | |
| 4.410 | 2-CH₃S-Pyrimidin-4-yl | |
| 4.411 | 4-C₆H₅O-Pyridin-2-yl | |
| 4.412 | 5-C₆H₅O-Pyridin-2-yl | |
| 4.413 | 6-C₆H₅O-Pyridin-2-yl | |
| 4.414 | 6-Cl-Pyridin-3-yl | |
| 4.415 | 3,6-(CH₃)₂-Pyridin-2-yl | |
| 4.416 | 4,6-(CH₃)₂-Pyridin-2-yl | |
| 4.417 | 5,6-(CH₃)₂-Pyridin-2-yl | |
| 4.418 | 4-C₆H₅-6-CH₃-Pyridin-2-yl | |
| 4.419 | 4,6-(C₆H₅)₂-Pyridin-2-yl | |
| 4.420 | 3,4-Cl₂-6-CH₃-Pyridin-2-yl | |
| 4.421 | 3,4,5-Cl₃-Pyridin-2-yl | |
| 4.422 | 3-CH₃CO-4-CH₃-Pyridin-2-yl | |
| 4.423 | 3-CH₃CO-4,6-(CH₃)-Pyridin-2-yl | |
| 4.424 | 3-CH₃OCO-Pyridin-2-yl | |
| 4.425 | 3-CH₃OCO-4-CH₃-Pyridin-2-yl | |
| 4.426 | 3-CH₃-4-Cl-Pyridin-2-yl | |
| 4.427 | 3-CH₃-5-Cl-Pyridin-2-yl | |
| 4.428 | 3-CH₃-6-Cl-Pyridin-2-yl | |
| 4.429 | 4-CH₃-5-Cl-Pyridin-2-yl | |
| 4.430 | 4-CH₃-6-Cl-Pyridin-2-yl | |
| 4.431 | Pyridin-2-yl | |
| 4.432 | Pyridin-3-yl | |

TABLE IV-continued

| | |
|---|---|
| 4.433 | Pyridin-4-yl |
| 4.434 | Pyridin-5-yl |
| 4.435 | Pyrimidin-4-yl |
| 4.436 | 2-Cl-6-CH$_3$-Pyrimidin-4-yl |
| 4.437 | 2,6-Di-Cl-Pyrimidin-4-yl |
| 4.438 | 2,5,6-Tri-Cl-Pyrimidin-4-yl |
| 4.439 | 2-Cl-Pyrimidin-4-yl |
| 4.440 | 2-CH$_3$-Thiazol-4-yl |
| 4.441 | 1,2,4-Triazin-3-yl |
| 4.442 | 1,3,5-Triazin-2-yl |
| 4.443 | Pyrazin-2-yl |
| 4.444 | Quinolin-2-yl |
| 4.445 | Quinolin-3-yl |
| 4.446 | Pyridazin-3-yl |
| 4.447 | 6-Cl-Pyrazin-2-yl |
| 4.448 | 6-CH$_3$O-Pyridazin-3-yl |
| 4.449 | 6-Cl-4-CH$_3$-Pyridazin-3-yl |
| 4.450 | 6-Cl-5-CH$_3$-Pyridazin-3-yl |
| 4.451 | 1,3-Benzthiazol-2-yl |
| 4.452 | Isoquinolin-1-yl |
| 4.453 | Quinolin-4-yl |
| 4.454 | 6-Cl-Pyridazin-3-yl |
| 4.455 | Pyridazin-4-yl |
| 4.456 | Quinazolin-4-yl |
| 4.457 | 7-Cl-Quinolin-4-yl |
| 4.458 | Purin-7-yl |
| 4.459 | 2-Cl-Purin-7-yl |
| 4.460 | 5-NO$_2$-Thien-2-yl |
| 4.461 | Thiazol-2-yl |
| 4.462 | Thiazol-4-yl |
| 4.463 | Thiazol-5-yl |
| 4.464 | Oxazol-2-yl |
| 4.465 | Oxazol-4-yl |
| 4.466 | Oxazol-5-yl |
| 4.467 | 1,2,4-Triazin-5-yl |
| 4.468 | 1,2,4-Triazin-6-yl |
| 4.469 | 6-Cl-Pyrazin-2-yl |
| 4.470 | 6-Cl-Pyrazin-3-yl |
| 4.471 | 6-Cl-Pyridazin-3-yl |
| 4.472 | 1,2,4-Triazol-1-yl |
| 4.473 | 1,2,3-Triazol-1-yl |
| 4.474 | 2-Cl-1,2,4-Oxadiazol-5-yl |
| 4.475 | 3-Cl-1,2,4-Oxadiazol-5-yl |
| 4.476 | Furan-2-yl |
| 4.477 | N—CH$_3$-Pyrrol-2-yl |
| 4.478 | 3-CH$_3$-Quinolin-2-yl |
| 4.479 | 4-CH$_3$-Quinolin-2-yl |
| 4.480 | 4-C$_6$H$_5$-Quinolin-2-yl |
| 4.481 | 4-CH$_3$CH$_2$-Quinolin-2-yl |
| 4.482 | 6-Cl-Quinolin-2-yl |
| 4.483 | 8-CH$_3$-Quinolin-2-yl |
| 4.484 | 8-Cl-Quinolin-2-yl |
| 4.485 | 3,4-(CH$_3$)$_2$-Quinolin-2-yl |
| 4.486 | 4-CH$_3$-8-CH$_3$O-Quinolin-2-yl |
| 4.487 | 4-CH$_3$-8-Cl-Quinolin-2-yl |
| 4.488 | 2-CH$_3$-Quinolin-4-yl |
| 4.489 | 2-Cl-Quinolin-4-yl |
| 4.490 | Quinolin-8-yl |
| 4.491 | 2-CH$_3$-Quinolin-8-yl |
| 4.492 | 2-Cl-Quinolin-8-yl |
| 4.493 | 2-CH$_3$-6-Cl-Quinolin-8-yl |
| 4.494 | 2-Thiophenyl |
| 4.495 | 3-Thiophenyl |
| 4.496 | 4-Cl-3-Thiophenyl |
| 4.497 | 2-Quinooxazinyl |
| 4.498 | 2-Furyl |
| 4.499 | 3-Furyl |
| 4.500 | 1-Pyrrolyl |
| 4.501 | 1-Imidazolyl |
| 4.502 | Oxiranyl |
| 4.503 | 1-Acetidinyl |
| 4.504 | 1-Pyrrolidinyl |
| 4.505 | 2-Tetrahydrofuryl |
| 4.506 | 2-Tetrahydropyranyl |
| 4.507 | 3-Tetrahydropyranyl |
| 4.508 | 1-Piperidinyl |
| 4.509 | 1-Morpholidinyl |
| 4.510 | 1-Piperazinyl |
| 4.511 | 1,3-Dioxan-2-yl |
| 4.512 | CH$_3$—CO |
| 4.513 | CH$_3$CH$_2$—CO |
| 4.514 | n-C$_3$H$_7$—CO |

TABLE IV-continued

| | |
|---|---|
| 4.515 | iso-$C_3H_7$—CO |
| 4.516 | n-$C_4H_9$—CO |
| 4.517 | sec.-$C_4H_9$—CO |
| 4.518 | tert.-$C_4H_9$—CO |
| 4.519 | iso-$C_4$—$H_9$—CO |
| 4.520 | $CH_3O$—CO |
| 4.521 | $CH_3CH_2O$—CO |
| 4.522 | n-$C_3H_7O$—CO |
| 4.523 | iso-$C_3H_7O$—CO |
| 4.524 | n-$C_4H_9O$—CO |
| 4.525 | sec.-$C_4H_9O$—CO |
| 4.526 | tert.-$C_4H_9O$—CO |
| 4.527 | iso-$C_4H_9O$—CO |
| 4.528 | Phenyl-CO |
| 4.529 | 2-Fluorophenyl-CO |
| 4.530 | 3-Fluorophenyl-CO |
| 4.531 | 4-Fluorophenyl-CO |
| 4.532 | Pentafluorophenyl-CO |
| 4.533 | 2-Chlorophenyl-CO |
| 4.534 | 3-Chlorophenyl-CO |
| 4.535 | 4-Chlorophenyl-CO |
| 4.536 | Pentachlorophenyl-CO |
| 4.537 | 2,3-Dichlorophenyl-CO |
| 4.538 | 2,4-Dichlorophenyl-CO |
| 4.539 | 2,5-Dichlorophenyl-CO |
| 4.540 | 2,6-Dichlorophenyl-CO |
| 4.541 | 3,4-Dichlorophenyl-CO |
| 4.542 | 3,5-Dichlorophenyl-CO |
| 4.543 | 2,3,4-Trichlorophenyl-CO |
| 4.544 | 2,3,5-Trichlorophenyl-CO |
| 4.545 | 2,3,6-Trichlorophenyl-CO |
| 4.546 | 2,4,5-Trichlorophenyl-CO |
| 4.547 | 2,4,6-Trichlorophenyl-CO |
| 4.548 | 3,4,5-Trichlorophenyl-CO |
| 4.549 | 2,3,4,6-Tetrachlorophenyl-CO |
| 4.550 | 2,3,5,6-Tetrachlorophenyl-CO |
| 4.551 | 2-Bromophenyl-CO |
| 4.552 | 3-Bromophenyl-CO |
| 4.553 | 4-Bromophenyl-CO |
| 4.554 | 2,4-Dibromophenyl-CO |
| 4.555 | 3-Bromo-4-Fluorophenyl-CO |
| 4.556 | 3-Bromo-4-Methoxyphenyl-CO |
| 4.557 | 2-Iodophenyl-CO |
| 4.558 | 3-Iodophenyl-CO |
| 4.559 | 4-Iodophenyl-CO |
| 4.560 | 2-Chloro-4-Fluorophenyl-CO |
| 4.561 | 2-Chloro-5-Fluorophenyl-CO |
| 4.562 | 2-Chloro-6-Fluorophenyl-CO |
| 4.563 | 2-Chloro-4-Bromophenyl-CO |
| 4.564 | 2-Bromo-4-Chlorophenyl-CO |
| 4.565 | 2-Bromo-4-Fluorophenyl-CO |
| 4.566 | 3-Bromo-4-Chlorophenyl-CO |
| 4.567 | 3-Chloro-4-Fluorophenyl-CO |
| 4.568 | 3-Fluoro-4-Chlorophenyl-CO |
| 4.569 | 2-Cyanophenyl-CO |
| 4.570 | 3-Cyanophenyl-CO |
| 4.571 | 4-Cyanophenyl-CO |
| 4.572 | 2-Nitrophenyl-CO |
| 4.573 | 3-Nitrophenyl-CO |
| 4.574 | 4-Nitrophenyl-CO |
| 4.575 | 2-Methylphenyl-CO |
| 4.576 | 3-Methylphenyl-CO |
| 4.577 | 4-Methylphenyl-CO |
| 4.578 | 2,4-Dimethylphenyl-CO |
| 4.579 | 2,6-Dimethylphenyl-CO |
| 4.580 | 3,4-Dimethylphenyl-CO |
| 4.581 | 3,5-Dimethylphenyl-CO |
| 4.582 | 2,3,4-Trimethylphenyl-CO |
| 4.583 | 2,3,5-Trimethylphenyl-CO |
| 4.584 | 2,3,6-Trimethylphenyl-CO |
| 4.585 | 2,4,5-Trimethylphenyl-CO |
| 4.586 | 2,4,6-Trimethylphenyl-CO |
| 4.587 | 3,4,5-Trimethylphenyl-CO |
| 4.588 | 6-F-Pyridin-3-yl-CO |
| 4.589 | 6-Cl-Pyridin-3-yl-CO |
| 4.590 | 6-Br-Pyridin-3-yl-CO |
| 4.591 | 6-$CH_3$-Pyridin-3-yl-CO |
| 4.592 | 6-$CF_3$-Pyridin-3-yl-CO |
| 4.593 | 6-$CH_3O$-Pyridin-3-yl-CO |
| 4.594 | 2-F-Pyridin-4-yl-CO |
| 4.595 | 2-Cl-Pyridin-4-yl-CO |
| 4.596 | 2-Br-Pyridin-4-yl-CO |

TABLE IV-continued

| | |
|---|---|
| 4.597 | 2-CH$_3$-Pyridin-4-yl-CO |
| 4.598 | 2-CF$_3$-Pyridin-4-yl-CO |
| 4.599 | 2-CH$_3$O-Pyridin-4-yl-CO |
| 4.600 | 3-F-Pyridin-4-yl-CO |
| 4.601 | 3-Cl-Pyridin-4-yl-CO |
| 4.602 | 3-Br-Pyridin-4-yl-CO |
| 4.603 | 3-CH$_3$-Pyridin-4-yl-CO |
| 4.604 | 3-CF$_3$-Pyridin-4-yl-CO |
| 4.605 | 3-CH$_3$O-Pyridin-4-yl-CO |
| 4.606 | 5-F-Pyridin-4-yl-CO |
| 4.607 | 5-Cl-Pyridin-4-yl-CO |
| 4.608 | 5-Br-Pyridin-4-yl-CO |
| 4.609 | 5-CH$_3$-Pyridin-4-yl-CO |
| 4.610 | 5-CF$_3$-Pyridin-4-yl-CO |
| 4.611 | 5-CH$_3$O-Pyridin-4-yl-CO |
| 4.612 | 6-F-Pyridin-4-yl-CO |
| 4.613 | 6-Cl-Pyridin-4-yl-CO |
| 4.614 | 6-Br-Pyridin-4-yl-CO |
| 4.615 | 6-CH$_3$-Pyridin-4-yl-CO |
| 4.616 | 6-CF$_3$-Pyridin-4-yl-CO |
| 4.617 | 6-CH$_3$O-Pyridin-4-yl-CO |
| 4.618 | 2-F-Pyridin-5-yl-CO |
| 4.619 | 2-Cl-Pyridin-5-yl-CO |
| 4.620 | 2-Br-Pyridin-5-yl-CO |
| 4.621 | 2-CH$_3$-Pyridin-5-yl-CO |
| 4.622 | 2-CF$_3$-Pyridin-5-yl-CO |
| 4.623 | 2-CH$_3$O-Pyridin-5-yl-CO |
| 4.624 | 4-F-Pyridin-5-yl-CO |
| 4.625 | 4-Cl-Pyridin-5-yl-CO |
| 4.626 | 4-Br-Pyridin-5-yl-CO |
| 4.627 | 4-CH$_3$-Pyridin-5-yl-CO |
| 4.628 | 4-CF$_3$-Pyridin-5-yl-CO |
| 4.629 | 4-CH$_3$O-Pyridin-5-yl-CO |
| 4.630 | 3-F-Pyridin-2-yl-CO |
| 4.631 | 3-Cl-Pyridin-2-yl-CO |
| 4.632 | 3-Br-Pyridin-2-yl-CO |
| 4.633 | 3-CH$_3$-Pyridin-2-yl-CO |
| 4.634 | 3-CF$_3$-Pyridin-2-yl-CO |
| 4.635 | 3-CH$_3$O-Pyridin-2-yl-CO |
| 4.636 | 4-F-Pyridin-2-yl-CO |
| 4.637 | 4-Br-Pyridin-2-yl-CO |
| 4.638 | 4-CF$_3$-Pyridin-2-yl-CO |
| 4.639 | 4-CH$_3$O-Pyridin-2-yl-CO |
| 4.640 | 5-F-Pyridin-2-yl-CO |
| 4.641 | 5-Cl-Pyridin-2-yl-CO |
| 4.642 | 5-Br-Pyridin-2-yl-CO |
| 4.643 | 5-CF$_3$-Pyridin-2-yl-CO |
| 4.644 | 5-CH$_3$-Pyridin-2-yl-CO |
| 4.645 | 5-CH$_3$O-Pyridin-2-yl-CO |
| 4.646 | 6-F-Pyridin-2-yl-CO |
| 4.647 | 6-Cl-Pyridin-2-yl-CO |
| 4.648 | 6-Br-Pyridin-2-yl-CO |
| 4.649 | 6-CH$_3$-Pyridin-2-yl-CO |
| 4.650 | 6-CF$_3$-Pyridin-2-yl-CO |
| 4.651 | 6-CH$_3$O-Pyridin-2-yl-CO |
| 4.652 | 2-F-Pyridin-3-yl-CO |
| 4.653 | 2-Cl-Pyridin-3-yl-CO |
| 4.654 | 2-Br-Pyridin-3-yl-CO |
| 4.655 | 2-CH$_3$-Pyridin-3-yl-CO |
| 4.656 | 2-CF$_3$-Pyridin-3-yl-CO |
| 4.657 | 2-CH$_3$O-Pyridin-3-yl-CO |
| 4.658 | 4-F-Pyridin-3-yl-CO |
| 4.659 | 4-Cl-Pyridin-3-yl-CO |
| 4.660 | 4-Br-Pyridin-3-yl-CO |
| 4.661 | 4-CH$_3$O-Pyridin-3-yl-CO |
| 4.662 | 4-CF$_3$-Pyridin-3-yl-CO |
| 4.663 | 4-CH$_3$-Pyridin-3-yl-CO |
| 4.664 | 5-F-Pyridin-3-yl-CO |
| 4.665 | 5-Cl-Pyridin-3-yl-CO |
| 4.666 | 5-Br-Pyridin-3-yl-CO |
| 4.667 | 5-CH$_3$-Pyridin-3-yl-CO |
| 4.668 | 5-CF$_3$-Pyridin-3-yl-CO |
| 4.669 | 5-CH$_3$O-Pyridin-3-yl-CO |

TABLE V

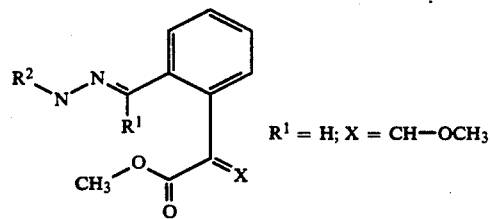

$R^1 = H; X = CH-OCH_3$

| Comp. no. | R² | IR (cm⁻¹) |
|---|---|---|
| 5.1 | Methyl | |
| 5.2 | Ethyl | |
| 5.3 | n-Propyl | |
| 5.4 | iso-Propyl | |
| 5.5 | n-Butyl | |
| 5.6 | iso-Butyl | |
| 5.7 | sec.-Butyl | |
| 5.8 | tert.-Butyl | |
| 5.9 | n-Hexyl | |
| 5.10 | n-Decyl | |
| 5.11 | Cyclopropyl | |
| 5.12 | Cyclohexyl | |
| 5.13 | 1-Methylcyclopropyl | |
| 5.14 | 1-Methylcyclohexyl | |
| 5.15 | Ethenyl | |
| 5.16 | 1-Propenyl | |
| 5.17 | 2-Methyl-1-propenyl | |
| 5.18 | 2-Propenyl | |
| 5.19 | 2-Butenyl | |
| 5.20 | Phenyl | m.p. 210° C. |
| 5.21 | 2-Fluorophenyl | |
| 5.22 | 3-Fluorophenyl | |
| 5.23 | 4-Fluorophenyl | |
| 5.24 | 2-Chlorophenyl | |
| 5.25 | 3-Chlorophenyl | |
| 5.26 | 4-Chlorophenyl | |
| 5.27 | Pentachlorophenyl | |
| 5.28 | 2,3-Dichlorophenyl | |
| 5.29 | 2,4-Dichlorophenyl | |
| 5.30 | 2,5-Dichlorophenyl | |
| 5.31 | 2,6-Dichlorophenyl | |
| 5.32 | 3,4-Dichlorophenyl | |
| 5.33 | 3,5-Dichlorophenyl | |
| 5.34 | 2,3,4-Trichlorophenyl | |
| 5.35 | 2,3,5-Trichlorophenyl | |
| 5.36 | 2,3,6-Trichlorophenyl | |
| 5.37 | 2,4,5-Trichlorophenyl | |
| 5.38 | 2,4,6-Trichlorophenyl | |
| 5.39 | 3,4,5-Trichlorophenyl | |
| 5.40 | 2,3,4,5-Tetrachlorophenyl | |
| 5.41 | 2,3,4,6-Tetrachlorophenyl | |
| 5.42 | 2-Bromophenyl | |
| 5.43 | 3-Bromophenyl | |
| 5.44 | 4-Bromophenyl | |
| 5.45 | 2,4-Dibromophenyl | |
| 5.46 | 3-Bromo-4-Fluorophenyl | |
| 5.47 | 3-Bromo-4-Methoxyphenyl | |
| 5.48 | 2-Iodophenyl | |
| 5.49 | 3-Iodophenyl | |
| 5.50 | 4-Iodophenyl | |
| 5.51 | 2-Chloro-4-Fluorophenyl | |
| 5.52 | 2-Chloro-5-Fluorophenyl | |
| 5.53 | 2-Chloro-6-Fluorophenyl | |
| 5.54 | 2-Chloro-4-Bromophenyl | |
| 5.55 | 2-Bromo-4-Chlorophenyl | |
| 5.56 | 2-Bromo-4-Fluorophenyl | |
| 5.57 | 3-Bromo-4-Chlorophenyl | |
| 5.58 | 3-Chloro-4-Fluorophenyl | |
| 5.59 | 3-Fluoro-4-Chlorophenyl | |
| 5.60 | 2-Cyanophenyl | |
| 5.61 | 3-Cyanophenyl | |
| 5.62 | 4-Cyanophenyl | |
| 5.63 | 2-Nitrophenyl | |
| 5.64 | 3-Nitrophenyl | |
| 5.65 | 4-Nitrophenyl | |
| 5.66 | 2-Methylphenyl | 1706, 1621, 1435, 1287, 1251, 1128, 1096 |

TABLE V-continued

| | |
|---|---|
| 5.67 | 3-Methylphenyl |
| 5.68 | 4-Methylphenyl |
| 5.69 | 2,4-Dimethylphenyl |
| 5.70 | 2,6-Dimethylphenyl |
| 5.71 | 3,4-Dimethylphenyl |
| 5.72 | 3,5-Dimethylphenyl |
| 5.73 | 2,3,4-Trimethylphenyl |
| 5.74 | 2,3,5-Trimethylphenyl |
| 5.75 | 2,3,6-Trimethylphenyl |
| 5.76 | 2,4,5-Trimethylphenyl |
| 5.77 | 2,4,6-Trimethylphenyl |
| 5.78 | 3,4,5-Trimethylphenyl |
| 5.79 | Pentamethylphenyl |
| 5.80 | 2-Methyl-5-Methoxyphenyl |
| 5.81 | 2-Methyl-6-Methoxyphenyl |
| 5.82 | 2-Methyl-4-iso-Propoxyphenyl |
| 5.83 | 2-Methyl-2,5-Dimethoxyphenyl |
| 5.84 | 2-Methoxyphenyl |
| 5.85 | 3-Methoxyphenyl |
| 5.86 | 4-Methoxyphenyl |
| 5.87 | 2,3-Dimethoxyphenyl |
| 5.88 | 2,4-Dimethoxyphenyl |
| 5.89 | 2,5-Dimethoxyphenyl |
| 5.90 | 2,6-Dimethoxyphenyl |
| 5.91 | 3,4-Dimethoxyphenyl |
| 5.92 | 3,5-Dimethoxyphenyl |
| 5.93 | 3,6-Dimethoxyphenyl |
| 5.94 | 2,3,4-Trimethoxyphenyl |
| 5.95 | 2,3,5-Trimethoxyphenyl |
| 5.96 | 2,3,6-Trimethoxyphenyl |
| 5.97 | 2,4,5-Trimethoxyphenyl |
| 5.98 | 2,4,6-Trimethoxyphenyl |
| 5.99 | 3,4,5-Trimethoxyphenyl |
| 5.100 | 2-Ethoxyphenyl |
| 5.101 | 3-Ethoxyphenyl |
| 5.102 | 4-Ethoxyphenyl |
| 5.103 | 2-iso-Propoxyphenyl |
| 5.104 | 3-iso-Propoxyphenyl |
| 5.105 | 2-Phenylphenyl |
| 5.106 | 3-Phenylphenyl |
| 5.107 | 4-Phenylphenyl |
| 5.108 | 2-Phenoxyphenyl |
| 5.109 | 3-Phenoxyphenyl |
| 5.110 | 4-Phenoxyphenyl |
| 5.111 | 2-Benzyloxyphenyl |
| 5.112 | 3-Benzyloxyphenyl |
| 5.113 | 4-Benzyloxyphenyl |
| 5.114 | 4-(Imidazol-1'-yl)phenyl |
| 5.115 | 4-(Piperazin-1'yl)phenyl) |
| 5.116 | 4-(Morpholino-1'-yl)phenyl |
| 5.117 | 4-(Piperidinyl-1'-yl)phenyl |
| 5.118 | 4-(Pyridyl-2'-oxy)phenyl |
| 5.119 | 2-Cyclopropylphenyl |
| 5.120 | 3-Cyclopropylphenyl |
| 5.121 | 4-Cyclopropylphenyl |
| 5.122 | 3-Cyclohexylphenyl |
| 5.123 | 4-Cyclohexylphenyl |
| 5.124 | 4-Oxiranylphenyl |
| 5.125 | 4-iso-Propoxyphenyl |
| 5.126 | 3-tert.-Butoxyphenyl |
| 5.127 | 4-tert.-Butoxyphenyl |
| 5.128 | 2-Trifluoromethoxyphenyl |
| 5.129 | 3-Trifluoromethoxyphenyl |
| 5.130 | 4-Trifluoromethoxyphenyl |
| 5.131 | 2-Chloromethylphenyl |
| 5.132 | 3-Chloromethylphenyl |
| 5.133 | 4-Chloromethylphenyl |
| 5.134 | 2-Trifluoromethylphenyl |
| 5.135 | 3-Trifluoromethylphenyl |
| 5.136 | 4-Trifluoromethylphenyl |
| 5.137 | 2-(Methoxyiminomethyl)phenyl |
| 5.138 | 3-(Methoxyiminomethyl)phenyl |
| 5.139 | 4-(Methoxyiminomethyl)phenyl |
| 5.140 | 2-(Ethoxyiminomethyl)phenyl |
| 5.141 | 3-(Ethoxyiminomethyl)phenyl |
| 5.142 | 4-(Ethoxyiminomethyl)phenyl |
| 5.143 | 2-(n-Propoxyiminomethyl)phenyl |
| 5.144 | 3-(n-Propoxyiminomethyl)phenyl |
| 5.145 | 4-(n-Propoxyiminomethyl)phenyl |
| 5.146 | 2-(iso-Propoxyiminomethyl)phenyl |
| 5.147 | 3-(iso-Propoxyiminomethyl)phenyl |
| 5.148 | 2-(Ethoxyimino-1'-ethyl)phenyl |

TABLE V-continued

| | |
|---|---|
| 5.149 | 3-(Ethoxyimino-1'-ethyl)phenyl |
| 5.150 | 4-(Ethoxyimino-1'-ethyl)phenyl |
| 5.151 | 2-(n-Propoxyimino-1'-ethyl)phenyl |
| 5.152 | 3-(n-Propoxyimino-1'-ethyl)phenyl |
| 5.153 | 4-(n-Propoxyimino-1'-ethyl)phenyl |
| 5.154 | 2-(n-Butoxyamino-1'-ethyl)phenyl |
| 5.155 | 3-(n-Butoxyamino-1'-ethyl)phenyl |
| 5.156 | 4-(n-Butoxyamino-1'-ethyl)phenyl |
| 5.157 | 2-(n-Pentoxyimino-1'-ethyl)phenyl |
| 5.158 | 3-(n-Pentoxyimino-1'-ethyl)phenyl |
| 5.159 | 4-(n-Pentoxyimino-1'-ethyl)phenyl |
| 5.160 | 2-(n-Hexoxyimino-1'-ethyl)phenyl |
| 5.161 | 3-(n-Hexoxyimino-1'-ethyl)phenyl |
| 5.162 | 4-(n-Hexoxyimino-1'-ethyl)phenyl |
| 5.163 | 2-(Allyloxyimino-1'-ethyl)phenyl |
| 5.164 | 3-(Allyloxyimino-1'-ethyl)phenyl |
| 5.165 | 4-(Allyloxyimino-1'-ethyl)phenyl |
| 5.166 | 2-(Benzyloxyimino-1'-ethyl)phenyl |
| 5.167 | 3-(Benzyloxyimino-1'-ethyl)phenyl |
| 5.168 | 4-(Benzyloxyimino-1'-ethyl)phenyl |
| 5.169 | 2-(2-Fluorophenyl)phenyl |
| 5.170 | 2-(2-Chlorophenyl)phenyl |
| 5.171 | 2-(2-Bromophenyl)phenyl |
| 5.172 | 2-(2-Methylphenyl)phenyl |
| 5.173 | 4-(iso-Propoxyiminomethyl)phenyl |
| 5.174 | 2-(n-Butoxyiminomethyl)phenyl |
| 5.175 | 3-(n-Butoxyiminomethyl)phenyl |
| 5.176 | 4-(n-Butoxyiminomethyl)phenyl |
| 5.177 | 2-(iso-Butoxyiminomethyl)phenyl |
| 5.178 | 3-(iso-Butoxyiminomethyl)phenyl |
| 5.179 | 4-(iso-Butoxyiminomethyl)phenyl |
| 5.180 | 2-(tert.-Butoxyiminomethyl)phenyl |
| 5.181 | 3-(tert.-Butoxyiminomethyl)phenyl |
| 5.182 | 4-(tert.-Butoxyiminomethyl)phenyl |
| 5.183 | 2-(n-Pentoxyiminomethyl)phenyl |
| 5.184 | 3-(n-Pentoxyiminomethyl)phenyl |
| 5.185 | 4-(n-Pentoxyiminomethyl)phenyl |
| 5.186 | 2-(n-Hexoxyiminomethyl)phenyl |
| 5.187 | 3-(n-Hexoxyiminomethyl)phenyl |
| 5.188 | 4-(n-Hexoxyiminomethyl)phenyl |
| 5.189 | 2-(Allyloxyiminomethyl)phenyl |
| 5.190 | 3-(Allyloxyiminomethyl)phenyl |
| 5.191 | 4-(Allyloxyiminomethyl)phenyl |
| 5.192 | 2-(Benzyloxyiminomethyl)phenyl |
| 5.193 | 3-(Benzyloxyiminomethyl)phenyl |
| 5.194 | 4-(Benzyloxyiminomethyl)phenyl |
| 5.195 | 2-(Methoxyimino-1'-ethyl)phenyl |
| 5.196 | 3-(Methoxyimino-1'-ethyl)phenyl |
| 5.197 | 4-(Methoxyimino-1'-ethyl)phenyl |
| 5.198 | 3-Phenoxyphenyl |
| 5.199 | 4-Phenoxyphenyl |
| 5.200 | 2-Benzyloxyphenyl |
| 5.201 | 3-Benzyloxyphenyl |
| 5.202 | 4-Benzyloxyphenyl |
| 5.203 | 4-(Imidazol-1'-yl)phenyl |
| 5.204 | 4-(Piperazin-1'-yl)phenyl |
| 5.205 | 4-(Morpholin-1'-yl)phenyl |
| 5.206 | 4-(Piperidin-1'-yl)phenyl |
| 5.207 | 4-Pyridyl-2'-oxy)phenyl |
| 5.208 | 2-Cyclopropylphenyl |
| 5.209 | 3-Cyclopropylphenyl |
| 5.210 | 4-Cyclopropylphenyl |
| 5.211 | 3-Cyclohexylphenyl |
| 5.212 | 4-Cyclohexylphenyl |
| 5.213 | 4-Oxiranylphenyl |
| 5.214 | 6-F-Pyridin-3-yl |
| 5.215 | 6-Cl-Pyridin-3-yl |
| 5.216 | 6-Br-Pyridin-3-yl |
| 5.217 | 6-$CH_3$-Pyridin-3-yl |
| 5.218 | 6-$CF_3$-Pyridin-3-yl |
| 5.219 | 6-$CH_3O$-Pyridin-3-yl |
| 5.220 | 2-F-Pyridin-4-yl |
| 5.221 | 2-Cl-Pyridin-4-yl |
| 5.222 | 2-Br-Pyridin-4-yl |
| 5.223 | 2-$CH_3$-Pyridin-4-yl |
| 5.224 | 2-$CF_3$-Pyridin-4-yl |
| 5.225 | 2-$CH_3O$-Pyridin-4-yl |
| 5.226 | 3-F-Pyridin-4-yl |
| 5.227 | 3-Cl-Pyridin-4-yl |
| 5.228 | 3-Br-Pyridin-4-yl |
| 5.229 | 3-$CH_3$-Pyridin-4-yl |
| 5.230 | 3-$CF_3$-Pyridin-4-yl |

TABLE V-continued

| | |
|---|---|
| 5.231 | 3-CH$_3$O-Pyridin-3-yl |
| 5.232 | 5-F-Pyridin-4-yl |
| 5.233 | 5-Cl-Pyridin-4-yl |
| 5.234 | 5-Br-Pyridin-4-yl |
| 5.235 | 5-CH$_3$-Pyridin-4-yl |
| 5.236 | 5-CF$_3$-Pyridin-4-yl |
| 5.237 | 5-CH$_3$O-Pyridin-4-yl |
| 5.238 | 6-F-Pyridin-4-yl |
| 5.239 | 6-Cl-Pyridin-4-yl |
| 5.240 | 6-Br-Pyridin-4-yl |
| 5.241 | 6-CH$_3$-Pyridin-4-yl |
| 5.242 | 6-CF$_3$-Pyridin-4-yl |
| 5.243 | 6-CH$_3$O-Pyridin-4-yl |
| 5.244 | 2-F-Pyridin-5-yl |
| 5.245 | 2-Cl-Pyridin-5-yl |
| 5.246 | 2-Br-Pyridin-5-yl |
| 5.247 | 2-CH$_3$-Pyridin-5-yl |
| 5.248 | 2-CF$_3$-Pyridin-5-y |
| 5.249 | 2-CH$_3$O-Pyridin-5-yl |
| 5.250 | 4-F-Pyridin-5-yl |
| 5.251 | 4-Cl-Pyridin-5-yl |
| 5.252 | 4-Br-Pyridin-5-yl |
| 5.253 | 4-CH$_3$-Pyridin-5-yl |
| 5.254 | 4-CF$_3$-Pyridin-5-yl |
| 5.255 | 4-CH$_3$O-Pyridin-5-yl |
| 5.256 | 3-F-Pyridin-2-yl |
| 5.257 | 3-Cl-Pyridin-2-yl |
| 5.258 | 3-Br-Pyridin-2-yl |
| 5.259 | 3-CH$_3$-Pyridin-2-yl |
| 5.260 | 3-CF$_3$-Pyridin-2-yl |
| 5.261 | 3-CH$_3$O-Pyridin-2-yl |
| 5.262 | 4-F-Pyridin-2-yl |
| 5.263 | 4-Br-Pyridin-2-yl |
| 5.264 | 4-CF$_3$-Pyridin-2-yl |
| 5.265 | 4-CH$_3$O-Pyridin-2-yl |
| 5.266 | 5-F-Pyridin-2-yl |
| 5.267 | 5-Cl-Pyridin-2-yl |
| 5.268 | 5-Br-Pyridin-2-yl |
| 5.269 | 5-CF$_3$-Pyridin-2-yl |
| 5.270 | 5-CH$_3$-Pyridin-2-yl |
| 5.271 | 5-CH$_3$O-Pyridin-2-yl |
| 5.272 | 6-F-Pyridin-2-yl |
| 5.273 | 6-Cl-Pyridin-2-yl |
| 5.274 | 6-Br-Pyridin-2-yl |
| 5.275 | 6-CH$_3$-Pyridin-2-yl |
| 5.276 | 6-CF$_3$-Pyridin-2-yl |
| 5.277 | 6-CH$_3$O-Pyridin-2-yl |
| 5.278 | 2-F-Pyridin-3-yl |
| 5.279 | 4-Cl-Pyridin-2-yl |
| 5.280 | 2-Br-Pyridin-3-yl |
| 5.281 | 2-CH$_3$-Pyridin-3-yl |
| 5.282 | 2-CF$_3$-Pyridin-3-yl |
| 5.283 | 2-CH$_3$O-Pyridin-3-yl |
| 5.284 | 4-F-Pyridin-3-yl |
| 5.285 | 4-Cl-Pyridin-3-yl |
| 5.286 | 4-Br-Pyridin-3-yl |
| 5.287 | 4-CH$_3$-Pyridin-3-yl |
| 5.288 | 4-CF$_3$-Pyridin-3-yl |
| 5.289 | 4-CH$_3$O-Pyridin-3-yl |
| 5.290 | 5-F-Pyridin-3-yl |
| 5.291 | 5-Cl-Pyridin-3-yl |
| 5.292 | 5-Br-Pyridin-3-yl |
| 5.293 | 5-CH$_3$-Pyridin-3-yl |
| 5.294 | 5-CF$_3$-Pyridin-3-yl |
| 5.295 | 5-CH$_3$O-Pyridin-3-yl |
| 5.296 | 3-F-5-CF$_3$-Pyridin-2-yl |
| 5.297 | 3,6-Cl$_2$-5-CF$_3$-Pyridin-2-yl |
| 5.298 | 6-Cl-4-CN-Pyridin-2-yl |
| 5.299 | 3-CN-5-NO$_2$-Pyridin-2-yl |
| 5.300 | 2-Cl-6-F-Pyridin-2-yl |
| 5.301 | 6-Cl-4-F-Pyridin-2-yl |
| 5.302 | 4,6-F$_2$-Pyridin-2-yl |
| 5.303 | 3,5-Cl$_2$-6-F-Pyridin-2-yl |
| 5.304 | 6-CH$_3$O-3-NO$_2$-Pyridin-2-yl |
| 5.305 | 4-CN-6-F-Pyridin-2-yl |
| 5.306 | 6-Cl-5-CN-Pyridin-2-yl |
| 5.307 | 6-Cl-3-CN-Pyridin-2-yl |
| 5.308 | 6-Cl-5-NO$_2$-Pyridin-2-yl |
| 5.309 | 6-Cl-3-NO$_2$-Pyridin-2-yl |
| 5.310 | 5-CN-6-F-Pyridin-2-yl |
| 5.311 | 3-CN-6-F-Pyridin-2-yl |
| 5.312 | 4,6-(CN)$_2$-Pyridin-2-yl |

TABLE V-continued

| | |
|---|---|
| 5.313 | 5-Br-4-CF$_3$-Pyridin-2-yl |
| 5.314 | 3-NO$_2$-5-CF$_3$-Pyridin-2-yl |
| 5.315 | 5-NH$_2$-Pyridin-2-yl |
| 5.316 | 5-NO$_2$-Pyridin-2-yl |
| 5.317 | 4-CH$_3$-5-NO$_2$-Pyridin-2-yl |
| 5.318 | 2,6-Cl$_2$-Pyridin-4-yl |
| 5.319 | 5-(CH$_3$OCO)-Pyridin-2-yl |
| 5.320 | 5-Cl-6-F-Pyridin-2-yl |
| 5.321 | 5-Cl-6-OH-Pyridin-2-yl |
| 5.322 | 5-Cl-6-CH$_3$O-Pyridin-2-yl |
| 5.323 | 5-Cl-6-CN-Pyridin-2-yl |
| 5.324 | 5,6-Cl$_2$-Pyridin-2-yl |
| 5.325 | 6-Br-5-Cl-Pyridin-2-yl |
| 5.326 | 5-Br-6-F-Pyridin-2-yl |
| 5.327 | 5-Br-6-Cl-Pyridin-2-yl |
| 5.328 | 5-Br-6-CN-Pyridin-2-yl |
| 5.329 | 5-Br-6-OH-Pyridin-2-yl |
| 5.330 | 5-Br-6-CH$_3$O-Pyridin-2-yl |
| 5.331 | 4-CN-Pyridin-2-yl |
| 5.332 | 6-CN-Pyridin-2-yl |
| 5.333 | 5-Cl-Pyridin-2-yl |
| 5.334 | 5-F-Pyridin-2-yl |
| 5.335 | 5-CF$_3$-1,3,4-Thiadiazol-2-yl |
| 5.336 | 4-Cl-1,2,5-Thiadiazol-3-yl |
| 5.337 | 4-Cl-Pyrimidin-2-yl |
| 5.338 | 4-Br-Pyrimidin-2-yl |
| 5.339 | 4-F-Pyrimidin-2-yl |
| 5.340 | 4-CH$_3$-Pyrimidin-2-yl |
| 5.341 | 4-CH$_3$O-Pyrimidin-2-yl |
| 5.342 | 4-CH$_3$CH$_2$O-Pyrimidin-2-yl |
| 5.343 | 4-NO$_2$-Pyrimidin-2-yl |
| 5.344 | 4-CN-Pyrimidin-2-yl |
| 5.345 | 4-CF$_3$-Pyrimidin-2-yl |
| 5.346 | 4-C$_6$H$_5$-Pyrimidin-2-yl |
| 5.347 | 4-C$_6$H$_5$O-Pyrimidin-2-yl |
| 5.348 | 5-F-Pyrimidin-2-yl |
| 5.349 | 5-CH$_3$-Pyrimidin-2-yl |
| 5.350 | 5-CH$_3$O-Pyrimidin-2-yl |
| 5.351 | 5-CH$_3$CH$_2$O-Pyrimidin-2-yl |
| 5.352 | 5-NO$_2$-Pyrimidin-2-yl |
| 5.353 | 5-CN-Pyrimidin-2-yl |
| 5.354 | 5-CF$_3$-Pyrimidin-2-yl |
| 5.355 | 5-C$_6$H$_5$-Pyrimidin-2-yl |
| 5.356 | 5-C$_6$H$_5$O-Pyrimidin-2-yl |
| 5.357 | 4,5-Cl$_2$-Pyrimidin-2-yl |
| 5.358 | 4,6-Cl$_2$-Pyrimidin-2-yl |
| 5.359 | 4-Cl-5-CH$_3$O-Pyrimidin-2-yl |
| 5.360 | 2-F-Pyrimidin-4-yl |
| 5.361 | 2-Cl-Pyrimidin-4-yl |
| 5.362 | 2-F-Pyrimidin-4-yl |
| 5.363 | 2-Br-Pyrimidin-4-yl |
| 5.364 | 2-CH$_3$-Pyrimidin-4-yl |
| 5.365 | 2-CH$_3$O-Pyrimidin-4-yl |
| 5.366 | 2-CH$_3$CH$_2$O-Pyrimidin-4-yl |
| 5.367 | 2-NO$_2$-Pyrimidin-4-yl |
| 5.368 | 2-CH$_3$S-Pyrimidin-4-yl |
| 5.369 | 2-Cyano-Pyrimidin-4-yl |
| 5.370 | 2-CF$_3$-Pyrimidin-4-yl |
| 5.371 | 2-C$_6$H$_5$O-Pyrimidin-4-yl |
| 5.372 | 2-C$_6$H$_5$-Pyrimidin-4-yl |
| 5.373 | 6-NO$_2$-Pyrimidin-4-yl |
| 5.374 | 6-Cyano-Pyrimidin-4-yl |
| 5.375 | 6-CF$_3$-Pyrimidin-4-yl |
| 5.376 | 6-C$_6$H$_5$O-Pyrimidin-4-yl |
| 5.377 | 6-C$_6$H$_5$-Pyrimidin-4-yl |
| 5.378 | 5-F-Pyrimidin-4-yl |
| 5.379 | 5-Cl-Pyrimidin-4-yl |
| 5.380 | 5-Br-Pyrimidin-4-yl |
| 5.381 | 5-CH$_3$-Pyrimidin-4-yl |
| 5.382 | 5-CH$_3$O-Pyrimidin-4-yl |
| 5.383 | 5-CH$_3$CH$_2$O-Pyrimidin-4-yl |
| 5.384 | 5-NO$_2$-Pyrimidin-4-yl |
| 5.385 | 5-Cyano-Pyrimidin-4-yl |
| 5.386 | 5-CF$_3$-Pyrimidin-4-yl |
| 5.387 | 5-C$_6$H$_5$O-Pyrimidin-4-yl |
| 5.388 | 5-C$_6$H$_5$-Pyrimidin-4-yl |
| 5.389 | 2-Cl-Pyrimidin-5-yl |
| 5.390 | 2-CH$_3$-Pyrimidin-5-yl |
| 5.391 | 2-F-Pyrimidin-5-yl |
| 5.392 | 2-CH$_3$O-Pyrimidin-5-yl |
| 5.393 | 2-Cyano-Pyrimidin-5-yl |
| 5.394 | 4-CH$_3$-Pyrimidin-5-yl |

TABLE V-continued

| | | |
|---|---|---|
| 5.395 | 4-CH$_3$O-Pyrimidin-5-yl | |
| 5.396 | 4-CF$_3$-Pyrimidin-5-yl | |
| 5.397 | 2,4(CH$_3$)$_2$-Pyrimidin-5-yl | |
| 5.398 | 2-CH$_3$S-4-CH$_3$O-Pyrimidin-5-yl | |
| 5.399 | Pyrrol-2-yl-6-Cl-3-NO$_2$-Pyrimidin-2-yl | |
| 5.400 | 6-Cl-3-NO$_2$-Pyrimidin-2-yl | |
| 5.401 | 6-Cl-5-NO$_2$-Pyrimidin-2-yl | |
| 5.402 | 3,6(CH$_3$)$_2$-Pyrazin-2-yl | |
| 5.403 | 6-F-Pyrimidin-4-yl | |
| 5.404 | 6-Br-Pyrimidin-4-yl | |
| 5.405 | 6-CH$_3$-Pyrimidin-4-yl | |
| 5.406 | 6-CH$_3$O-Pyrimidin-4-yl | |
| 5.407 | 6-CH$_3$CH$_2$O-Pyrimidin-4-yl | |
| 5.408 | 4,6-(CH$_3$)$_2$-Pyrimidin-2-yl | 1703, 1588, 1568, 1435, 1377, 1292, 1189 |
| 5.409 | 2-CH$_3$S-6-CH$_3$-Pyrimidin-4-yl | |
| 5.410 | 2-CH$_3$S-Pyrimidin-4-yl | |
| 5.411 | 4-C$_6$H$_5$O-Pyridin-2-yl | |
| 5.412 | 5-C$_6$H$_5$O-Pyridin-2-yl | |
| 5.413 | 6-C$_6$H$_5$O-Pyridin-2-yl | |
| 5.414 | 6-Cl-Pyridin-3-yl | |
| 5.415 | 3,6-(CH$_3$)$_2$-Pyridin-2-yl | |
| 5.416 | 4,6-(CH$_3$)$_2$-Pyridin-2-yl | |
| 5.417 | 5,6-(CH$_3$)$_2$-Pyridin-2-yl | |
| 5.418 | 4-C$_6$H$_5$-6-CH$_3$-Pyridin-2-yl | |
| 5.419 | 4,6-(C$_6$H$_5$)$_2$-Pyridin-2-yl | |
| 5.420 | 3,4-Cl$_2$-6-CH$_3$-Pyridin-2-yl | |
| 5.421 | 3,4,5-Cl$_3$-Pyridin-2-yl | |
| 5.422 | 3-CH$_3$CO-4-CH$_3$-Pyridin-2-yl | |
| 5.423 | 3-CH$_3$CO-4,6-(CH$_3$)-Pyridin-2-yl | |
| 5.424 | 3-CH$_3$OCO-Pyridin-2-yl | |
| 5.425 | 3-CH$_3$OCO-4-CH$_3$-Pyridin-2-yl | |
| 5.426 | 3-CH$_3$-4-Cl-Pyridin-2-yl | |
| 5.427 | 3-CH$_3$-5-Cl-Pyridin-2-yl | |
| 5.428 | 3-CH$_3$-6-Cl-Pyridin-2-yl | |
| 5.429 | 4-CH$_3$-5-Cl-Pyridin-2-yl | |
| 5.430 | 4-CH$_3$-6-Cl-Pyridin-2-yl | |
| 5.431 | Pyridin-2-yl | |
| 5.432 | Pyridin-3-yl | |
| 5.433 | Pyridin-4-yl | |
| 5.434 | Pyridin-5-yl | |
| 5.435 | Pyrimidin-4-yl | |
| 5.436 | 2-Cl-6-CH$_3$-Pyrimidin-4-yl | |
| 5.437 | 2,6-Cl$_2$-Pyrimidin-4-yl | |
| 5.438 | 2,5,6-Cl$_3$-Pyrimidin-4-yl | |
| 5.439 | 2-Cl-Pyrimidin-4-yl | |
| 5.440 | 2-CH$_3$-Thiazol-4-yl | |
| 5.441 | 1,2,4-Triazin-3-yl | |
| 5.442 | 1,3,5-Triazin-2-yl | |
| 5.443 | Pyrazin-2-yl | |
| 5.444 | Quinolin-2-yl | |
| 5.445 | Quinolin-3-yl | |
| 5.446 | Pyridazin-3-yl | |
| 5.447 | 6-Cl-Pyrazin-2-yl | |
| 5.448 | 6-CH$_3$O-Pyridazin-3-yl | |
| 5.449 | 6-Cl-4-CH$_3$-Pyridazin-3-yl | |
| 5.450 | 6-Cl-5-CH$_3$-Pyridazin-3-yl | |
| 5.451 | Benzthiazol-2-yl | |
| 5.452 | Isoquinolin-1-yl | |
| 5.453 | Quinolin-4-yl | |
| 5.454 | 6-Cl-Pyridazin-3-yl | 1711, 1625, 1604, 1523, 1408, 1289, 1259, 1195, 1133 |
| 5.455 | Pyridazin-4-yl | |
| 5.456 | Quinazolin-4-yl | |
| 5.457 | 7-Cl-Quinolin-4-yl | |
| 5.458 | Purin-2-yl | |
| 5.459 | 2-Cl-Purin-7-yl | |
| 5.460 | 5-NO$_2$-Thien-2-yl | |
| 5.461 | Thiazol-2-yl | |
| 5.462 | Thiazol-4-yl | |
| 5.463 | Thiazol-5-yl | |
| 5.464 | Oxazol-2-yl | |
| 5.465 | Oxazol-4-yl | |
| 5.466 | Oxazol-5-yl | |
| 5.467 | 1,2,4-Triazin-5-yl | |
| 5.468 | 1,2,4-Triazin-6-yl | |
| 5.469 | 6-Cl-Pyrazin-2-yl | |
| 5.470 | 6-Cl-Pyrazin-3-yl | |
| 5.471 | 6-Cl-Pyridazin-3-yl | |
| 5.472 | 1,2,4-Triazol-1-yl | |

TABLE V-continued

| | |
|---|---|
| 5.473 | 1,2,3-Triazol-1-yl |
| 5.474 | 2-Cl-1,2,4-Oxadiazol-5-yl |
| 5.475 | 3-Cl-1,2,4-Oxadiazol-5-yl |
| 5.476 | Furan-2-yl |
| 5.477 | N—$CH_3$-Pyrrol-2-yl |
| 5.478 | 3-$CH_3$-Quinolin-2-yl |
| 5.479 | 4-$CH_3$-Quinolin-2-yl |
| 5.480 | 4-$C_6H_5$-Quinolin-2-yl |
| 5.481 | 4-$CH_3CH_2$-Quinolin-2-yl |
| 5.482 | 6-Cl-Quinolin-2-yl |
| 5.483 | 8-$CH_3$-Quinolin-2-yl |
| 5.484 | 8-Cl-Quinolin-2-yl |
| 5.485 | 3,4-$(CH_3)_2$-Quinolin-2-yl |
| 5.486 | 4-$CH_3$-8-$CH_3O$-Quinolin-2-yl |
| 5.487 | 4-$CH_3$-8-Cl-Quinolin-2-yl |
| 5.488 | 2-$CH_3$-Quinolin-4-yl |
| 5.489 | 2-Cl-Quinolin-4-yl |
| 5.490 | Quinolin-8-yl |
| 5.491 | 2-$CH_3$-Quinolin-8-yl |
| 5.492 | 2-Cl-Quinolin-8-yl |
| 5.493 | 2-$CH_3$-6-Cl-Quinolin-8-yl |
| 5.494 | 2-Thiophenyl |
| 5.495 | 3-Thiophenyl |
| 5.496 | 4-Cl-3-Thiophenyl |
| 5.497 | 2-Quinooxazinyl |
| 5.498 | 2-Furyl |
| 5.499 | 3-Furyl |
| 5.500 | 1-Pyrrolyl |
| 5.501 | 1-Imidazolyl |
| 5.502 | Oxiranyl |
| 5.503 | 1-Acetidinyl |
| 5.504 | 1-Pyrrolidinyl |
| 5.505 | 2-Tetrahydrofuryl |
| 5.506 | 2-Tetrahydropyranyl |
| 5.507 | 3-Tetrahydropyranyl |
| 5.508 | 1-Piperidinyl |
| 5.509 | 1-Morpholidinyl |
| 5.510 | 1-Piperazinyl |
| 5.511 | 1,3-Dioxan-2-yl |
| 5.512 | $CH_3$—CO |
| 5.513 | $CH_3CH_2$—CO |
| 5.514 | n-$C_3H_7$—CO |
| 5.515 | iso-$C_3H_7$—CO |
| 5.516 | n-$C_4H_9$—CO |
| 5.517 | sec.-$C_4H_9$—CO |
| 5.518 | tert.-$C_4H_9$—CO |
| 5.519 | iso-$C_4H_9$—CO |
| 5.520 | $CH_3O$—CO |
| 5.521 | $CH_3CH_2O$—CO |
| 5.522 | n-$C_3H_7O$—CO |
| 5.523 | iso-$C_3H_7O$—CO |
| 5.524 | n-$C_4H_9O$—CO |
| 5.525 | sec.-$C_4H_9O$—CO |
| 5.526 | tert.-$C_4H_9O$—CO |
| 5.527 | iso-$C_4H_9O$—CO |
| 5.528 | Phenyl-CO |
| 5.529 | 2-Fluorophenyl-CO |
| 5.530 | 3-Fluorophenyl-CO |
| 5.531 | 4-Fluorophenyl-CO |
| 5.532 | Pentafluorophenyl-CO |
| 5.533 | 2-Chlorophenyl-CO |
| 5.534 | 3-Chlorophenyl-CO |
| 5.535 | 4-Chlorophenyl-CO |
| 5.536 | Pentachlorophenyl-CO |
| 5.537 | 2,3-Dichlorophenyl-CO |
| 5.538 | 2,4-Dichlorophenyl-CO |
| 5.539 | 2,5-Dichlorophenyl-CO |
| 5.540 | 2,6-Dichlorophenyl-CO |
| 5.541 | 3,4-Dichlorophenyl-CO |
| 5.542 | 3,5-Dichlorophenyl-CO |
| 5.543 | 2,3,4-Trichlorophenyl-CO |
| 5.544 | 2,3,5-Trichlorophenyl-CO |
| 5.545 | 2,3,6-Trichlorophenyl-CO |
| 5.546 | 2,4,5-Trichlorophenyl-CO |
| 5.547 | 2,4,6-Trichlorophenyl-CO |
| 5.548 | 3,4,5-Trichlorophenyl-CO |
| 5.549 | 2,3,4,6-Tetrachlorophenyl-CO |
| 5.550 | 2,3,5,6-Tetrachlorophenyl-CO |
| 5.551 | 2-Bromophenyl-CO |
| 5.552 | 3-Bromophenyl-CO |
| 5.553 | 4-Bromophenyl-CO |
| 5.554 | 2,4-Dibromophenyl-CO |

TABLE V-continued

| | |
|---|---|
| 5.555 | 3-Bromo-4-Fluorophenyl-CO |
| 5.556 | 3-Bromo-4-Methoxyphenyl-CO |
| 5.557 | 2-Iodophenyl-CO |
| 5.558 | 3-Iodophenyl-CO |
| 5.559 | 4-Iodophenyl-CO |
| 5.560 | 2-Chloro-4-Fluorophenyl-CO |
| 5.561 | 2-Chloro-5-Fluorophenyl-CO |
| 5.562 | 2-Chloro-6-Fluorophenyl-CO |
| 5.563 | 2-Chloro-4-Bromophenyl-CO |
| 5.564 | 2-Bromo-4-Chlorophenyl-CO |
| 5.565 | 2-Bromo-4-Fluorophenyl-CO |
| 5.566 | 3-Bromo-4-Chlorophenyl-CO |
| 5.567 | 3-Chloro-4-Fluorophenyl-CO |
| 5.568 | 3-Fluoro-4-Chlorophenyl-CO |
| 5.569 | 2-Cyanophenyl-CO |
| 5.570 | 3-Cyanophenyl-CO |
| 5.571 | 4-Cyanophenyl-CO |
| 5.572 | 2-Nitrophenyl-CO |
| 5.573 | 3-Nitrophenyl-CO |
| 5.574 | 4-Nitrophenyl-CO |
| 5.575 | 2-Methylphenyl-CO |
| 5.576 | 3-Methylphenyl-CO |
| 5.577 | 4-Methylphenyl-CO |
| 5.578 | 2,4-Dimethylphenyl-CO |
| 5.579 | 2,6-Dimethylphenyl-CO |
| 5.580 | 3,4-Dimethylphenyl-CO |
| 5.581 | 3,5-Dimethylphenyl-CO |
| 5.582 | 2,3,4-Trimethylphenyl-CO |
| 5.583 | 2,3,5-Trimethylphenyl-CO |
| 5.584 | 2,3,6-Trimethylphenyl-CO |
| 5.585 | 2,4,5-Trimethylphenyl-CO |
| 5.586 | 2,4,6-Trimethylphenyl-CO |
| 5.587 | 3,4,5-Trimethylphenyl-CO |
| 5.588 | 6-F-Pyridin-3-yl-CO |
| 5.589 | 6-Cl-Pyridin-3-yl-CO |
| 5.590 | 6-Br-Pyridin-3-yl-CO |
| 5.591 | 6-CH$_3$-Pyridin-3-yl-CO |
| 5.592 | 6-CF$_3$-Pyridin-3-yl-CO |
| 5.593 | 6-CH$_3$O-Pyridin-3-yl-CO |
| 5.594 | 2-F-Pyridin-4-yl-CO |
| 5.595 | 2-Cl-Pyridin-4-yl-CO |
| 5.596 | 2-Br-Pyridin-4-yl-CO |
| 5.597 | 2-CH$_3$-Pyridin-4-yl-CO |
| 5.598 | 2-CF$_3$-Pyridin-4-yl-CO |
| 5.599 | 2-CH$_3$O-Pyridin-4-yl-CO |
| 5.600 | 3-F-Pyridin-4-yl-CO |
| 5.601 | 3-Cl-Pyridin-4-yl-CO |
| 5.602 | 3-Br-Pyridin-4-yl-CO |
| 5.603 | 3-CH$_3$-Pyridin-4-yl-CO |
| 5.604 | 3-CF$_3$-Pyridin-4-yl-CO |
| 5.605 | 3-CH$_3$O-Pyridin-4-yl-CO |
| 5.606 | 5-F-Pyridin-4-yl-CO |
| 5.607 | 5-Cl-Pyridin-4-yl-CO |
| 5.608 | 5-Br-Pyridin-4-yl-CO |
| 5.609 | 5-CH$_3$-Pyridin-4-yl-CO |
| 5.610 | 5-CF$_3$-Pyridin-4-yl-CO |
| 5.611 | 5-CH$_3$O-Pyridin-4-yl-CO |
| 5.612 | 6-F-Pyridin-4-yl-CO |
| 5.613 | 6-Cl-Pyridin-4-yl-CO |
| 5.614 | 6-Br-Pyridin-4-yl-CO |
| 5.615 | 6-CH$_3$-Pyridin-4-yl-CO |
| 5.616 | 6-CF$_3$-Pyridin-4-yl-CO |
| 5.617 | 6-CH$_3$O-Pyridin-4-yl-CO |
| 5.618 | 2-F-Pyridin-5-yl-CO |
| 5.619 | 2-Cl-Pyridin-5-yl-CO |
| 5.620 | 2-Br-Pyridin-5-yl-CO |
| 5.621 | 2-CH$_3$-Pyridin-5-yl-CO |
| 5.622 | 2-CF$_3$-Pyridin-5-yl-CO |
| 5.623 | 2-CH$_3$O-Pyridin-5-yl-CO |
| 5.624 | 4-F-Pyridin-5-yl-CO |
| 5.625 | 4-Cl-Pyridin-5-yl-CO |
| 5.626 | 4-Br-Pyridin-5-yl-CO |
| 5.627 | 4-CH$_3$-Pyridin-5-yl-CO |
| 5.628 | 4-CF$_3$-Pyridin-5-yl-CO |
| 5.629 | 4-CH$_3$O-Pyridin-5-yl-CO |
| 5.630 | 3-F-Pyridin-2-yl-CO |
| 5.631 | 3-Cl-Pyridin-2-yl-CO |
| 5.632 | 3-Br-Pyridin-2-yl-CO |
| 5.633 | 3-CH$_3$-Pyridin-2-yl-CO |
| 5.634 | 3-CF$_3$-Pyridin-2-yl-CO |
| 5.635 | 3-CH$_3$O-Pyridin-2-yl-CO |
| 5.636 | 4-F-Pyridin-2-yl-CO |

TABLE V-continued

| | |
|---|---|
| 5.637 | 4-Br-Pyridin-2-yl-CO |
| 5.638 | 4-CF$_3$-Pyridin-2-yl-CO |
| 5.639 | 4-CH$_3$O-Pyridin-2-yl-CO |
| 5.640 | 5-F-Pyridin-2-yl-CO |
| 5.641 | 5-Cl-Pyridin-2-yl-CO |
| 5.642 | 5-Br-Pyridin-2-yl-CO |
| 5.643 | 5-CF$_3$-Pyridin-2-yl-CO |
| 5.644 | 5-CH$_3$-Pyridin-2-yl-CO |
| 5.645 | 5-CH$_3$O-Pyridin-2-yl-CO |
| 5.646 | 6-F-Pyridin-2-yl-CO |
| 5.647 | 6-Cl-Pyridin-2-yl-CO |
| 5.648 | 6-Br-Pyridin-2-yl-CO |
| 5.649 | 6-CH$_3$-Pyridin-2-yl-CO |
| 5.650 | 6-CF$_3$-Pyridin-2-yl-CO |
| 5.651 | 6-CH$_3$O-Pyridin-2-yl-CO |
| 5.652 | 2-F-Pyridin-3-yl-CO |
| 5.653 | 2-Cl-Pyridin-3-yl-CO |
| 5.654 | 2-Br-Pyridin-3-yl-CO |
| 5.655 | 2-CH$_3$-Pyridin-3-yl-CO |
| 5.656 | 2-CF$_3$-Pyridin-3-yl-CO |
| 5.657 | 2-CH$_3$O-Pyridin-3-yl-CO |
| 5.658 | 4-F-Pyridin-3-yl-CO |
| 5.659 | 4-Cl-Pyridin-3-yl-CO |
| 5.660 | 4-Br-Pyridin-3-yl-CO |
| 5.661 | 4-CH$_3$-Pyridin-3-yl-CO |
| 5.662 | 4-CF$_3$-Pyridin-3-yl-CO |
| 5.663 | 4-CH$_3$O-Pyridin-3-yl-CO |
| 5.664 | 5-F-Pyridin-3-yl-CO |
| 5.665 | 5-Cl-Pyridin-3-yl-CO |
| 5.666 | 5-Br-Pyridin-3-yl-CO |
| 5.667 | 5-CH$_3$-Pyridin-3-yl-CO |
| 5.668 | 5-CF$_3$-Pyridin-3-yl-CO |
| 5.669 | 5-CH$_3$O-Pyridin-3-yl-CO |

TABLE VI

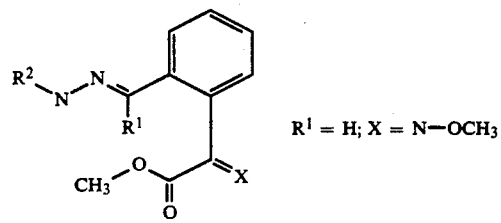

$R^1 = H; X = N-OCH_3$

| Comp. no. | R$^2$ | IR (cm$^{-1}$) |
|---|---|---|
| 6.1 | Methyl | |
| 6.2 | Ethyl | |
| 6.3 | n-Propyl | |
| 6.4 | iso-Propyl | |
| 6.5 | n-Butyl | |
| 6.6 | iso-Butyl | |
| 6.7 | sec.-Butyl | |
| 6.8 | tert.-Butyl | |
| 6.9 | n-Hexyl | |
| 6.10 | n-Decyl | |
| 6.11 | Cyclopropyl | |
| 6.12 | Cyclohexyl | |
| 6.13 | 1-Methylcyclopropyl | |
| 6.14 | 1-Methylcyclohexyl | |
| 6.15 | Ethenyl | |
| 6.16 | 1-Propenyl | |
| 6.17 | 2-Methyl-1-propenyl | |
| 6.18 | 2-Propenyl | |
| 6.19 | 2-Butenyl | |
| 6.20 | Phenyl | |
| 6.21 | 2-Fluorophenyl | |
| 6.22 | 3-Fluorophenyl | |
| 6.23 | 4-Fluorophenyl | |
| 6.24 | 2-Chlorophenyl | |
| 6.25 | 3-Chlorophenyl | |
| 6.26 | 4-Chlorophenyl | |
| 6.27 | Pentachlorophenyl | |
| 6.28 | 2,3-Dichlorophenyl | |
| 6.29 | 2,4-Dichlorophenyl | |
| 6.30 | 2,5-Dichlorophenyl | |
| 6.31 | 2,6-Dichlorophenyl | |

TABLE VI-continued

| | |
|---|---|
| 6.32 | 3,4-Dichlorophenyl |
| 6.33 | 3,5-Dichlorophenyl |
| 6.34 | 2,3,4-Trichlorophenyl |
| 6.35 | 2,3,5-Trichlorophenyl |
| 6.36 | 2,3,6-Trichlorophenyl |
| 6.37 | 2,4,5-Trichlorophenyl |
| 6.38 | 2,4,6-Trichlorophenyl |
| 6.39 | 3,4,5-Trichlorophenyl |
| 6.40 | 2,3,4,5-Tetrachlorophenyl |
| 6.41 | 2,3,4,6-Tetrachlorophenyl |
| 6.42 | 2-Bromophenyl |
| 6.43 | 3-Bromophenyl |
| 6.44 | 4-Bromophenyl |
| 6.45 | 2,4-Dibromophenyl |
| 6.46 | 3-Bromo-4-Fluorophenyl |
| 6.47 | 3-Bromo-4-Methoxyphenyl |
| 6.48 | 2-Iodophenyl |
| 6.49 | 3-Iodophenyl |
| 6.50 | 4-Iodophenyl |
| 6.51 | 2-Chloro-4-Fluorophenyl |
| 6.52 | 2-Chloro-5-Fluorophenyl |
| 6.53 | 2-Chloro-6-Fluorophenyl |
| 6.54 | 2-Chloro-4-Bromophenyl |
| 6.55 | 2-Bromo-4-Chlorophenyl |
| 6.56 | 2-Bromo-4-Fluorophenyl |
| 6.57 | 3-Bromo-4-Chlorophenyl |
| 6.58 | 3-Chloro-4-Fluorophenyl |
| 6.59 | 3-Fluoro-4-Chlorophenyl |
| 6.60 | 2-Cyanophenyl |
| 6.61 | 3-Cyanophenyl |
| 6.62 | 4-Cyanophenyl |
| 6.63 | 2-Nitrophenyl |
| 6.64 | 3-Nitrophenyl |
| 6.65 | 4-Nitrophenyl |
| 6.66 | 2-Methylphenyl |
| 6.67 | 3-Methylphenyl |
| 6.68 | 4-Methylphenyl |
| 6.69 | 2,4-Dimethylphenyl |
| 6.70 | 2,6-Dimethylphenyl |
| 6.71 | 3,4-Dimethylphenyl |
| 6.72 | 3,5-Dimethylphenyl |
| 6.73 | 2,3,4-Trimethylphenyl |
| 6.74 | 2,3,5-Trimethylphenyl |
| 6.75 | 2,3,6-Trimethylphenyl |
| 6.76 | 2,4,5-Trimethylphenyl |
| 6.77 | 2,4,6-Trimethylphenyl |
| 6.78 | 3,4,5-Trimethylphenyl |
| 6.79 | Pentamethylphenyl |
| 6.80 | 2-Methyl-5-Methoxyphenyl |
| 6.81 | 2-Methyl-6-Methoxyphenyl |
| 6.82 | 2-Methyl-4-iso-Propoxyphenyl |
| 6.83 | 2-Methyl-2,5-Dimethoxyphenyl |
| 6.84 | 2-Methoxyphenyl |
| 6.85 | 3-Methoxyphenyl |
| 6.86 | 4-Methoxyphenyl |
| 6.87 | 2,3-Dimethoxyphenyl |
| 6.88 | 2,4-Dimethoxyphenyl |
| 6.89 | 2,5-Dimethoxyphenyl |
| 6.90 | 2,6-Dimethoxyphenyl |
| 6.91 | 3,4-Dimethoxyphenyl |
| 6.92 | 3,5-Dimethoxyphenyl |
| 6.93 | 3,6-Dimethoxyphenyl |
| 6.94 | 2,3,4-Trimethoxyphenyl |
| 6.95 | 2,3,5-Trimethoxyphenyl |
| 6.96 | 2,3,6-Trimethoxyphenyl |
| 6.97 | 2,4,5-Trimethoxyphenyl |
| 6.98 | 2,4,6-Trimethoxyphenyl |
| 6.99 | 3,4,5-Trimethoxyphenyl |
| 6.100 | 2-Ethoxyphenyl |
| 6.101 | 3-Ethoxyphenyl |
| 6.102 | 4-Ethoxyphenyl |
| 6.103 | 2-iso-Propoxyphenyl |
| 6.104 | 3-iso-Propoxyphenyl |
| 6.105 | 2-Phenylphenyl |
| 6.106 | 3-Phenylphenyl |
| 6.107 | 4-Phenylphenyl |
| 6.108 | 2-Phenoxyphenyl |
| 6.109 | 3-Phenoxyphenyl |
| 6.110 | 4-Phenoxyphenyl |
| 6.111 | 2-Benzyloxyphenyl |
| 6.112 | 3-Benzyloxyphenyl |
| 6.113 | 4-Benzyloxyphenyl |

TABLE VI-continued

| | | |
|---|---|---|
| 6.114 | 4-(Imidazol-1'-yl)phenyl | |
| 6.115 | 4-(Piperazin-1'yl)phenyl | |
| 6.116 | 4-(Morpholino-1'-yl)phenyl | |
| 6.117 | 4-(Piperidinyl-1'-yl)phenyl | |
| 6.118 | 4-(Pyridyl-2'-oxy)phenyl | |
| 6.119 | 2-Cyclopropylphenyl | |
| 6.120 | 3-Cyclopropylphenyl | |
| 6.121 | 4-Cyclopropylphenyl | |
| 6.122 | 3-Cyclohexylphenyl | |
| 6.123 | 4-Cyclohexylphenyl | |
| 6.124 | 4-Oxiranylphenyl | |
| 6.125 | 4-iso-Propoxyphenyl | |
| 6.126 | 3-tert.-Butoxyphenyl | |
| 6.127 | 4-tert.-Butoxyphenyl | |
| 6.128 | 2-Trifluoromethoxyphenyl | |
| 6.129 | 3-Trifluoromethoxyphenyl | |
| 6.130 | 4-Trifluoromethoxymethyl | |
| 6.131 | 2-Chloromethylphenyl | |
| 6.132 | 3-Chloromethylphenyl | |
| 6.133 | 4-Chloromethylphenyl | |
| 6.134 | 2-Trifluoromethylphenyl | |
| 6.135 | 3-Trifluoromethylphenyl | 1728, 1614, 1464, 1338, 1164, 1123, 1066, 1018 |
| 6.136 | 4-Trifluoromethylphenyl | |
| 6.137 | 2-(Methoxyiminomethyl)phenyl | |
| 6.138 | 3-(Methoxyiminomethyl)phenyl | |
| 6.139 | 4-(Methoxyiminomethyl)phenyl | |
| 6.140 | 2-(Ethoxyiminomethyl)phenyl | |
| 6.141 | 3-(Ethoxyiminomethyl)phenyl | |
| 6.142 | 4-(Ethoxyiminomethyl)phenyl | |
| 6.143 | 2-(n-Propoxyiminomethyl)phenyl | |
| 6.144 | 3-(n-Propoxyiminomethyl)phenyl | |
| 6.145 | 4-(n-Propoxyiminomethyl)phenyl | |
| 6.146 | 2-(iso-Propoxyiminomethyl)phenyl | |
| 6.147 | 3-(iso-Propoxyiminomethyl)phenyl | |
| 6.148 | 2-(Ethoxyimino-1'-ethyl)phenyl | |
| 6.149 | 3-(Ethoxyimino-1'-ethyl)phenyl | |
| 6.150 | 4-(Ethoxyimino-1'-ethyl)phenyl | |
| 6.151 | 2-(n-Propoxyimino-1'-ethyl)phenyl | |
| 6.152 | 3-(n-Propoxyimino-1'-ethyl)phenyl | |
| 6.153 | 4-(n-Propoxyimino-1'-ethyl)phenyl | |
| 6.154 | 2-(n-Butoxyamino-1'-ethyl)phenyl | |
| 6.155 | 3-(n-Butoxyamino-1'-ethyl)phenyl | |
| 6.156 | 4-(n-Butoxyamino-1'-ethyl)phenyl | |
| 6.157 | 2-(n-Pentoxyimino-1'-ethyl)phenyl | |
| 6.158 | 3-(n-Pentoxyimino-1'-ethyl)phenyl | |
| 6.159 | 4-(n-Pentoxyimino-1'-ethyl)phenyl | |
| 6.160 | 2-(n-Hexoxyimino-1'-ethyl)phenyl | |
| 6.161 | 3-(n-Hexoxyimino-1'-ethyl)phenyl | |
| 6.162 | 4-(n-Hexoxyimino-1'-ethyl)phenyl | |
| 6.163 | 2-(Allyloxyimino-1'-ethyl)phenyl | |
| 6.164 | 3-(Allyloxyimino-1'-ethyl)phenyl | |
| 6.165 | 4-(Allyloxyimino-1'-ethyl)phenyl | |
| 6.166 | 2-(Benzyloxyimino-1'-ethyl)phenyl | |
| 6.167 | 3-(Benzyloxyimino-1'-ethyl)phenyl | |
| 6.168 | 4-(Benzyloxyimino-1'-ethyl)phenyl | |
| 6.169 | 2-(2'-Fluorophenyl)phenyl | |
| 6.170 | 2-(2-Chlorophenyl)phenyl | |
| 6.171 | 2-(2-Methylphenyl)phenyl | |
| 6.172 | 2-(2-Methoxyphenyl)phenyl | |
| 6.173 | 4-(iso-Propoxyiminomethyl)phenyl | |
| 6.174 | 2-(n-Butoxyiminomethyl)phenyl | |
| 6.175 | 3-(n-Butoxyiminomethyl)phenyl | |
| 6.176 | 4-(n-Butoxyiminomethyl)phenyl | |
| 6.177 | 2-(iso-Butoxyiminomethyl)phenyl | |
| 6.178 | 3-(iso-Butoxyiminomethyl)phenyl | |
| 6.179 | 4-(iso-Butoxyiminomethyl)phenyl | |
| 6.180 | 2-(tert.-Butoxyiminomethyl)phenyl | |
| 6.181 | 3-(tert.-Butoxyiminomethyl)phenyl | |
| 6.182 | 4-(tert.-Butoxyiminomethyl)phenyl | |
| 6.183 | 2-(n-Pentoxyiminomethyl)phenyl | |
| 6.184 | 3-(n-Pentoxyiminomethyl)phenyl | |
| 6.185 | 4-(n-Pentoxyiminomethyl)phenyl | |
| 6.186 | 2-(n-Hexoxyiminomethyl)phenyl | |
| 6.187 | 3-(n-Hexoxyiminomethyl)phenyl | |
| 6.188 | 4-(n-Hexoxyiminomethyl)phenyl | |
| 6.189 | 2-(Allyloxyiminomethyl)phenyl | |
| 6.190 | 3-(Allyloxyiminomethyl)phenyl | |
| 6.191 | 4-(Allyloxyiminomethyl)phenyl | |
| 6.192 | 2-(Benzyloxyiminomethyl)phenyl | |
| 6.193 | 3-(Benzyloxyiminomethyl)phenyl | |

TABLE VI-continued

| | |
|---|---|
| 6.194 | 4-(Benzyloxyiminomethyl)phenyl |
| 6.195 | 2-(Methoxyimino-1'-ethyl)phenyl |
| 6.196 | 3-(Methoxyimino-1'-ethyl)phenyl |
| 6.197 | 4-(Methoxyimino-1'-ethyl)phenyl |
| 6.198 | 3-Phenoxyphenyl |
| 6.199 | 4-Phenoxyphenyl |
| 6.200 | 2-Benzyloxyphenyl |
| 6.201 | 3-Benzyloxyphenyl |
| 6.202 | 4-Benzyloxyphenyl |
| 6.203 | 4-(Imidazol-1'-yl)phenyl |
| 6.204 | 4-(Piperazin-1'-yl)phenyl |
| 6.205 | 4-(Morpholin-1'-yl)phenyl |
| 6.206 | 4-(Piperidin-1'-yl)phenyl |
| 6.207 | 4-Pyridyl-2'-oxy)phenyl |
| 6.208 | 2-Cyclopropylphenyl |
| 6.209 | 3-Cyclopropylphenyl |
| 6.210 | 4-Cyclopropylphenyl |
| 6.211 | 3-Cyclohexylphenyl |
| 6.212 | 4-Cyclohexylphenyl |
| 6.213 | 4-Oxiranylphenyl |
| 6.214 | 6-F-Pyridin-3-yl |
| 6.215 | 6-Cl-Pyridin-3-yl |
| 6.216 | 6-Br-Pyridin-3-yl |
| 6.217 | 6-$CH_3$-Pyridin-3-yl |
| 6.218 | 6-$CF_3$-Pyridin-3-yl |
| 6.219 | 6-$CH_3O$-Pyridin-3-yl |
| 6.220 | 2-F-Pyridin-4-yl |
| 6.221 | 2-Cl-Pyridin-4-yl |
| 6.222 | 2-Br-Pyridin-4-yl |
| 6.223 | 2-$CH_3$-Pyridin-4-yl |
| 6.224 | 2-$CF_3$-Pyridin-4-yl |
| 6.225 | 2-$CH_3O$-Pyridin-4-yl |
| 6.226 | 3-F-Pyridin-4-yl |
| 6.227 | 3-Cl-Pyridin-4-yl |
| 6.228 | 3-Br-Pyridin-4-yl |
| 6.229 | 3-$CH_3$-Pyridin-4-yl |
| 6.230 | 3-$CF_3$-Pyridin-4-yl |
| 6.231 | 3-$CH_3O$-Pyridin-3-yl |
| 6.232 | 5-F-Pyridin-4-yl |
| 6.233 | 5-Cl-Pyridin-4-yl |
| 6.234 | 5-Br-Pyridin-4-yl |
| 6.235 | 5-$CH_3$-Pyridin-4-yl |
| 6.236 | 5-$CF_3$-Pyridin-4-yl |
| 6.237 | 5-$CH_3O$-Pyridin-4-yl |
| 6.238 | 6-F-Pyridin-4-yl |
| 6.239 | 6-Cl-Pyridin-4-yl |
| 6.240 | 6-Br-Pyridin-4-yl |
| 6.241 | 6-$CH_3$-Pyridin-4-yl |
| 6.242 | 6-$CF_3$-Pyridin-4-yl |
| 6.243 | 6-$CH_3O$-Pyridin-4-yl |
| 6.244 | 2-F-Pyridin-5-yl |
| 6.245 | 2-Cl-Pyridin-5-yl |
| 6.246 | 2-Br-Pyridin-5-yl |
| 6.247 | 2-$CH_3$-Pyridin-5-yl |
| 6.248 | 2-$CF_3$-Pyridin-5-y |
| 6.249 | 2-$CH_3O$-Pyridin-5-yl |
| 6.250 | 4-F-Pyridin-5-yl |
| 6.251 | 4-Cl-Pyridin-5-yl |
| 6.252 | 4-Br-Pyridin-5-yl |
| 6.253 | 4-$CH_3$-Pyridin-5-yl |
| 6.254 | 4-$CF_3$-Pyridin-5-yl |
| 6.255 | 4-$CH_3O$-Pyridin-5-yl |
| 6.256 | 3-F-Pyridin-2-yl |
| 6.257 | 3-Cl-Pyridin-2-yl |
| 6.258 | 3-Br-Pyridin-2-yl |
| 6.259 | 3-$CH_3$-Pyridin-2-yl |
| 6.260 | 3-$CF_3$-Pyridin-2-yl |
| 6.261 | 3-$CH_3O$-Pyridin-2-yl |
| 6.262 | 4-F-Pyridin-2-yl |
| 6.263 | 4-Br-Pyridin-2-yl |
| 6.264 | 4-$CF_3$-Pyridin-2-yl |
| 6.265 | 4-$CH_3O$-Pyridin-2-yl |
| 6.266 | 5-F-Pyridin-2-yl |
| 6.267 | 5-Cl-Pyridin-2-yl |
| 6.268 | 5-Br-Pyridin-2-yl |
| 6.269 | 5-$CF_3$-Pyridin-2-yl |
| 6.270 | 5-$CH_3$-Pyridin-2-yl |
| 6.271 | 5-$CH_3O$-Pyridin-2-yl |
| 6.272 | 6-F-Pyridin-2-yl |
| 6.273 | 6-Cl-Pyridin-2-yl |
| 6.274 | 6-Br-Pyridin-2-yl |
| 6.275 | 6-$CH_3$-Pyridin-2-yl |

TABLE VI-continued

| | |
|---|---|
| 6.276 | 6-CF$_3$-Pyridin-2-yl |
| 6.277 | 6-CH$_3$O-Pyridin-2-yl |
| 6.278 | 2-F-Pyridin-3-yl |
| 6.279 | 4-Cl-Pyridin-2-yl |
| 6.280 | 2-Br-Pyridin-3-yl |
| 6.281 | 2-CH$_3$-Pyridin-3-yl |
| 6.282 | 2-CF$_3$-Pyridin-3-yl |
| 6.283 | 2-CH$_3$O-Pyridin-3-yl |
| 6.284 | 4-F-Pyridin-3-yl |
| 6.285 | 4-Cl-Pyridin-3-yl |
| 6.286 | 4-Br-Pyridin-3-yl |
| 6.287 | 4-CH$_3$-Pyridin-3-yl |
| 6.288 | 4-CF$_3$-Pyridin-3-yl |
| 6.289 | 4-CH$_3$O-Pyridin-3-yl |
| 6.290 | 5-F-Pyridin-3-yl |
| 6.291 | 5-Cl-Pyridin-3-yl |
| 6.292 | 5-Br-Pyridin-3-yl |
| 6.293 | 5-CH$_3$-Pyridin-3-yl |
| 6.294 | 5-CF$_3$-Pyridin-3-yl |
| 6.295 | 5-CH$_3$O-Pyridin-3-yl |
| 6.296 | 3-F-5-CF$_3$-Pyridin-2-yl |
| 6.297 | 3,6-Cl$_2$-5-CF$_3$-Pyridin-2-yl |
| 6.298 | 6-Cl-4-CN-Pyridin-2-yl |
| 6.299 | 3-CN-5-NO$_2$-Pyridin-2-yl |
| 6.300 | 2-Cl-6-F-Pyridin-2-yl |
| 6.301 | 6-Cl-4-F-Pyridin-2-yl |
| 6.302 | 4,6-F$_2$-Pyridin-2-yl |
| 6.303 | 3,5-Cl$_2$-6-F-Pyridin-2-yl |
| 6.304 | 6-CH$_3$O-3-NO$_2$-Pyridin-2-yl |
| 6.305 | 4-CN-6-F-Pyridin-2-yl |
| 6.306 | 6-Cl-5-CN-Pyridin-2-yl |
| 6.307 | 6-Cl-3-CN-Pyridin-2-yl |
| 6.308 | 6-Cl-5-NO$_2$-Pyridin-2-yl |
| 6.309 | 6-Cl-3-NO$_2$-Pyridin-2-yl |
| 6.310 | 5-CN-6-F-Pyridin-2-yl |
| 6.311 | 3-CN-6-F-Pyridin-2-yl |
| 6.312 | 4,6-(CN)$_2$-Pyridin-2-yl |
| 6.313 | 5-Br-4-CF$_3$-Pyridin-2-yl |
| 6.314 | 3-NO$_2$-5-CF$_3$-Pyridin-2-yl |
| 6.315 | 5-NH$_2$-Pyridin-2-yl |
| 6.316 | 5-NO$_2$-Pyridin-2-yl |
| 6.317 | 4-CH$_3$-5-NO$_2$-Pyridin-2-yl |
| 6.318 | 2,6-Cl$_2$-Pyridin-4-yl |
| 6.319 | 5-(CH$_3$OCO)-Pyridin-2-yl |
| 6.320 | 5-Cl-6-F-Pyridin-2-yl |
| 6.321 | 5-Cl-6-OH-Pyridin-2-yl |
| 6.322 | 5-Cl-6-CH$_3$O-Pyridin-2-yl |
| 6.323 | 5-Cl-6-CN-Pyridin-2-yl |
| 6.324 | 5,6-Cl$_2$-Pyridin-2-yl |
| 6.325 | 6-Br-5-Cl-Pyridin-2-yl |
| 6.326 | 5-Br-6-F-Pyridin-2-yl |
| 6.327 | 5-Br-6-Cl-Pyridin-2-yl |
| 6.328 | 5-Br-6-CN-Pyridin-2-yl |
| 6.329 | 5-Br-6-OH-Pyridin-2-yl |
| 6.330 | 5-Br-6-CH$_3$O-Pyridin-2-yl |
| 6.331 | 4-CN-Pyridin-2-yl |
| 6.332 | 6-CN-Pyridin-2-yl |
| 6.333 | 5-Cl-Pyridin-2-yl |
| 6.334 | 5-F-Pyridin-2-yl |
| 6.335 | 5-CF$_3$-1,3,4-Thiadiazol-2-yl |
| 6.336 | 4-Cl-1,2,5-Thiadiazol-3-yl |
| 6.337 | 4-Cl-Pyrimidin-2-yl |
| 6.338 | 4-Br-Pyrimidin-2-yl |
| 6.339 | 4-F-Pyrimidin-2-yl |
| 6.340 | 4-CH$_3$-Pyrimidin-2-yl |
| 6.341 | 4-CH$_3$O-Pyrimidin-2-yl |
| 6.342 | 4-CH$_3$CH$_2$O-Pyrimidin-2-yl |
| 6.343 | 4-NO$_2$-Pyrimidin-2-yl |
| 6.344 | 4-CN-Pyrimidin-2-yl |
| 6.345 | 4-CF$_3$-Pyrimidin-2-yl |
| 6.346 | 4-C$_6$H$_5$-Pyrimidin-2-yl |
| 6.347 | 4-C$_6$H$_5$O-Pyrimidin-2-yl |
| 6.348 | 5-F-Pyrimidin-2-yl |
| 6.349 | 5-CH$_3$-Pyrimidin-2-yl |
| 6.350 | 5-CH$_3$O-Pyrimidin-2-yl |
| 6.351 | 5-CH$_3$CH$_2$O-Pyrimidin-2-yl |
| 6.352 | 5-NO$_2$-Pyrimidin-2-yl |
| 6.353 | 5-CN-Pyrimidin-2-yl |
| 6.354 | 5-CF$_3$-Pyrimidin-2-yl |
| 6.355 | 5-C$_6$H$_5$-Pyrimidin-2-yl |
| 6.356 | 5-C$_6$H$_5$O-Pyrimidin-2-yl |
| 6.357 | 4,5-Cl$_2$-Pyrimidin-2-yl |

TABLE VI-continued

| | | |
|---|---|---|
| 6.358 | 4,6-Cl$_2$-Pyrimidin-2-yl | |
| 6.359 | 4-Cl-5-CH$_3$O-Pyrimidin-2-yl | |
| 6.360 | 2-F-Pyrimidin-4-yl | |
| 6.361 | 2-Cl-Pyrimidin-4-yl | |
| 6.362 | 2-F-Pyrimidin-4-yl | |
| 6.363 | 2-Br-Pyrimidin-4-yl | |
| 6.364 | 2-CH$_3$-Pyrimidin-4-yl | |
| 6.365 | 2-CH$_3$O-Pyrimidin-4-yl | |
| 6.366 | 2-CH$_3$CH$_2$O-Pyrimidin-4-yl | |
| 6.367 | 2-NO$_2$-Pyrimidin-4-yl | |
| 6.368 | 2-CH$_3$S-Pyrimidin-4-yl | |
| 6.369 | 2-Cyano-Pyrimidin-4-yl | |
| 6.370 | 2-CF$_3$-Pyrimidin-4-yl | |
| 6.371 | 2-C$_6$H$_5$O-Pyrimidin-4-yl | |
| 6.372 | 2-C$_6$H$_5$-Pyrimidin-4-yl | |
| 6.373 | 6-NO$_2$-Pyrimidin-4-yl | |
| 6.374 | 6-Cyano-Pyrimidin-4-yl | |
| 6.375 | 6-CF$_3$-Pyrimidin-4-yl | |
| 6.376 | 6-C$_6$H$_5$O-Pyrimidin-4-yl | |
| 6.377 | 6-C$_6$H$_5$-Pyrimidin-4-yl | |
| 6.378 | 5-F-Pyrimidin-4-yl | |
| 6.379 | 5-Cl-Pyrimidin-4-yl | |
| 6.380 | 5-Br-Pyrimidin-4-yl | |
| 6.381 | 5-CH$_3$-Pyrimidin-4-yl | |
| 6.382 | 5-CH$_3$O-Pyrimidin-4-yl | |
| 6.383 | 5-CH$_3$CH$_2$O-Pyrimidin-4-yl | |
| 6.384 | 5-NO$_2$-Pyrimidin-4-yl | |
| 6.385 | 5-Cyano-Pyrimidin-4-yl | |
| 6.386 | 5-CF$_3$-Pyrimidin-4-yl | |
| 6.387 | 5-C$_6$H$_5$O-Pyrimidin-4-yl | |
| 6.388 | 5-C$_6$H$_5$-Pyrimidin-4-yl | |
| 6.389 | 2-Cl-Pyrimidin-5-yl | |
| 6.390 | 2-CH$_3$-Pyrimidin-5-yl | |
| 6.391 | 2-F-Pyrimidin-5-yl | |
| 6.392 | 2-CH$_3$O-Pyrimidin-5-yl | |
| 6.393 | 2-Cyano-Pyrimidin-5-yl | |
| 6.394 | 4-CH$_3$-Pyrimidin-5-yl | |
| 6.395 | 4-CH$_3$O-Pyrimidin-5-yl | |
| 6.396 | 4-CF$_3$-Pyrimidin-5-yl | |
| 6.397 | 2,4-(CH$_3$)$_2$-Pyrimidin-5-yl | |
| 6.398 | 2-CH$_3$S-4-CH$_3$O-Pyrimidin-5-yl | |
| 6.399 | Pyrrol-2-yl-6-Cl-3-NO$_2$-Pyridin-2-yl | |
| 6.400 | 6-Cl-3-NO$_2$-Pyridin-2-yl | |
| 6.401 | 6-Cl-5-NO$_2$-Pyridin-2-yl | |
| 6.402 | 3,6-(CH$_3$)$_2$-Pyrazin-2-yl | |
| 6.403 | 6-F-Pyrimidin-4-yl | |
| 6.404 | 6-Br-Pyrimidin-4-yl | |
| 6.405 | 6-CH$_3$-Pyrimidin-4-yl | |
| 6.406 | 6-CH$_3$O-Pyrimidin-4-yl | |
| 6.407 | 6-CH$_3$CH$_2$O-Pyrimidin-4-yl | |
| 6.408 | 4,6-(CH$_3$)$_2$-Pyrimidin-2-yl | 1745, 1594, 1561, 1459, 1446, 1339, 1210, 1067, 1011 |
| 6.409 | 2-CH$_3$S-6-CH$_3$-Pyrimidin-4-yl | |
| 6.410 | 2-CH$_3$S-Pyrimidin-4-yl | |
| 6.411 | 4-C$_6$H$_5$O-Pyridin-2-yl | |
| 6.412 | 5.-C$_6$H$_5$O-Pyridin-2-yl | |
| 6.413 | 6-C$_6$H$_5$O-Pyridin-2-yl | |
| 6.414 | 6-Cl-Pyridin-3-yl | |
| 6.415 | 3,6-(CH$_3$)$_2$-Pyridin-2-yl | |
| 6.416 | 4,6-(CH$_3$)$_2$-Pyridin-2-yl | |
| 6.417 | 5,6-(CH$_3$)$_2$-Pyridin-2-yl | |
| 6.418 | 4-C$_6$H$_5$-6-CH$_3$-Pyridin-2-yl | |
| 6.419 | 4,6-(C$_6$H$_5$)$_2$-Pyridin-2-yl | |
| 6.420 | 3,4-Cl$_2$-6-CH$_3$-Pyridin-2-yl | |
| 6.421 | 3,4,5-Cl$_3$-Pyridin-2-yl | |
| 6.422 | 3-CH$_3$CO-4-CH$_3$-Pyridin-2-yl | |
| 6.423 | 3-CH$_3$CO-4,6-(CH$_3$)-Pyridin-2-yl | |
| 6.424 | 3-CH$_3$OCO-Pyridin-2-yl | |
| 6.425 | 3-CH$_3$OCO-4-CH$_3$-Pyridin-2-yl | |
| 6.426 | 3-CH$_3$-4-Cl-Pyridin-2-yl | |
| 6.427 | 3-CH$_3$-5-Cl-Pyridin-2-yl | |
| 6.428 | 3-CH$_3$-6-Cl-Pyridin-2-yl | |
| 6.429 | 4-CH$_3$-5-Cl-Pyridin-2-yl | |
| 6.430 | 4-CH$_3$-6-Cl-Pyridin-2-yl | |
| 6.431 | Pyridin-2-yl | 1733, 1599, 1583, 1462, 1441, 1314, 1070 |
| 6.432 | Pyridin-3-yl | |
| 6.433 | Pyridin-4-yl | |
| 6.434 | Pyridin-5-yl | |
| 6.435 | Pyrimidin-4-yl | |

TABLE VI-continued

| | | |
|---|---|---|
| 6.436 | 2-Cl-6-CH$_3$-Pyrimidin-4-yl | |
| 6.437 | 2,6-Cl$_2$-Pyrimidin-4 yl | |
| 6.438 | 2,4,6-Cl$_3$-Pyrimidin-4-yl | |
| 6.439 | 2-Cl-Pyrimidin-4-yl | |
| 6.440 | 2-CH$_3$-Thiazol-4-yl | |
| 6.441 | 1,2,4-Triazin-3-yl | |
| 6.442 | 1,3,5-Triazin-2-yl | |
| 6.443 | Pyrazin-2-yl | |
| 6.444 | Quinolin-2-yl | |
| 6.445 | Quinolin-3-yl | |
| 6.446 | Pyridazin-3-yl | |
| 6.447 | 6-Cl-Pyrazin-2-yl | |
| 6.448 | 6-CH$_3$O-Pyridazin-3-yl | |
| 6.449 | 6-Cl-4-CH$_3$-Pyridazin-3-yl | |
| 6.450 | 6-Cl-5-CH$_3$-Pyridazin-3-yl | |
| 6.451 | 1,3-Benzthiazol-2-yl | |
| 6.452 | Isoquinolin-1-yl | |
| 6.453 | Quinolin-4-yl | |
| 6.454 | 6-Cl-Pyridazin-3-yl | |
| 6.455 | Pyridazin-4-yl | |
| 6.456 | Quinazolin-4-yl | |
| 6.457 | 7-Cl-Quinolin-4-yl | |
| 6.458 | Purin-7-yl | |
| 6.459 | 2-Cl-Purin-7-yl | |
| 6.460 | 5-NO$_2$-Thien-2-yl | |
| 6.461 | Thiazol-2-yl | |
| 6.462 | Thiazol-4-yl | |
| 6.463 | Thiazol-5-yl | |
| 6.464 | Oxazol-2-yl | |
| 6.465 | Oxazol-4-yl | |
| 6.466 | Oxazol-5-yl | |
| 6.467 | 1,2,4-Triazin-5-yl | |
| 6.468 | 1,2,4-Triazin-6-yl | |
| 6.469 | 6-Cl-Pyrazin-2-yl | |
| 6.470 | 6-Cl-Pyrazin-3-yl | |
| 6.471 | 6-Cl-Pyridazin-3-yl | 1723, 1608, 1593, 1529, 1409, 1204, 1069, 1013 |
| 6.472 | 1,2,4-Triazol-2-yl | |
| 6.473 | 1,2,3-Triazol-1-yl | |
| 6.474 | 2-Cl-1,2,4-Oxadiazol-5-yl | |
| 6.475 | 3-Cl-1,2,4-Oxadiazol-5-yl | |
| 6.476 | Furan-2-yl | |
| 6.477 | N-CH$_3$-Pyrrol-2-yl | |
| 6.478 | 3-CH$_3$-Quinolin-2-yl | |
| 6.479 | 4-CH$_3$-Quinolin-2-yl | |
| 6.480 | 4-C$_6$H$_5$-Quinolin-2-yl | |
| 6.481 | 3-Cl-4-CH$_3$-Quinolin-2-yl | |
| 6.482 | 6-Cl-Quinolin-2-yl | |
| 6.483 | 8-CH$_3$-Quinolin-2-yl | |
| 6.484 | 8-Cl-Quinolin-2-yl | |
| 6.485 | 3,4-(CH$_3$)$_2$-Quinolin-2-yl | |
| 6.486 | 4-CH$_3$-8-CH$_3$O-Quinolin-2-yl | |
| 6.487 | 4-CH$_3$-8-Cl-Quinolin-2-yl | |
| 6.488 | 2-CH$_3$-Quinolin-4-yl | |
| 6.489 | 2-Cl-Quinolin-4-yl | |
| 6.490 | Quinolin-8-yl | |
| 6.491 | 2-CH$_3$-Quinolin-8-yl | |
| 6.492 | 2-Cl-Quinolin-8-yl | |
| 6.493 | 2-CH$_3$-6-Cl-Quinolin-8-yl | |
| 6.494 | 2-Thiophenyl | |
| 6.495 | 3-Thiophenyl | |
| 6.496 | 4-Cl-3-Thiophenyl | |
| 6.497 | 2-Quinooxazinyl | |
| 6.498 | 2-Furyl | |
| 6.499 | 3-Furyl | |
| 6.500 | 1-Pyrrolyl | |
| 6.501 | 1-Imidazolyl | |
| 6.502 | Oxiranyl | |
| 6.503 | 1-Acetidinyl | |
| 6.504 | 1-Pyrrolidinyl | |
| 6.505 | 2-Tetrahydrofuryl | |
| 6.506 | 2-Tetrahydropyranyl | |
| 6.507 | 3-Tetrahydropyranyl | |
| 6.508 | 1-Piperidinyl | |
| 6.509 | 1-Morpholidinyl | |
| 6.510 | 1-Piperazinyl | |
| 6.511 | 1,3-Dioxan-2-yl | |
| 6.512 | CH$_3$—CO | |
| 6.513 | CH$_3$CH$_2$—CO | |
| 6.514 | n-C$_3$H$_7$—CO | |
| 6.515 | iso-C$_3$H$_7$—CO | |

TABLE VI-continued

| | |
|---|---|
| 6.516 | n-$C_4H_9$—CO |
| 6.517 | sec.-$C_4H_9$—CO |
| 6.518 | tert.-$C_4H_9$—CO |
| 6.519 | iso-$C_4$—$H_9$—CO |
| 6.520 | $CH_3O$—CO |
| 6.521 | $CH_3CH_2O$—CO |
| 6.522 | n-$C_3H_7O$—CO |
| 6.523 | iso-$C_3H_7O$—CO |
| 6.524 | n-$C_4H_9O$—CO |
| 6.525 | sec.-$C_4H_9O$—CO |
| 6.526 | tert.-$C_4H_9O$—CO |
| 6.527 | iso-$C_4H_9O$—CO |
| 6.528 | Phenyl-CO |
| 6.529 | 2-Fluorophenyl-CO |
| 6.530 | 3-Fluorophenyl-CO |
| 6.531 | 4-Fluorophenyl-CO |
| 6.532 | Pentafluorophenyl-CO |
| 6.533 | 2-Chlorophenyl-CO |
| 6.534 | 3-Chlorophenyl-CO |
| 6.535 | 4-Chlorophenyl-CO |
| 6.536 | Pentachlorophenyl-CO |
| 6.537 | 2,3-Dichlorophenyl-CO |
| 6.538 | 2,4-Dichlorophenyl-CO |
| 6.539 | 2,5-Dichlorophenyl-CO |
| 6.540 | 2,6-Dichlorophenyl-CO |
| 6.541 | 3,4-Dichlorophenyl-CO |
| 6.542 | 3,5-Dichlorophenyl-CO |
| 6.543 | 2,3,4-Trichlorophenyl-CO |
| 6.544 | 2,3,5-Trichlorophenyl-CO |
| 6.545 | 2,3,6-Trichlorophenyl-CO |
| 6.546 | 2,4,5-Trichlorophenyl-CO |
| 6.547 | 2,4,6-Trichlorophenyl-CO |
| 6.548 | 3,4,5-Trichlorophenyl-CO |
| 6.549 | 2,3,4,6-Tetrachlorophenyl-CO |
| 6.550 | 2,3,5,6-Tetrachlorophenyl-CO |
| 6.551 | 2-Bromophenyl-CO |
| 6.552 | 3-Bromophenyl-CO |
| 6.553 | 4-Bromophenyl-CO |
| 6.554 | 2,4-Dibromophenyl-CO |
| 6.555 | 3-Bromo-4-Fluorophenyl-CO |
| 6.556 | 3-Bromo-4-Methoxyphenyl-CO |
| 6.557 | 2-Iodophenyl-CO |
| 6.558 | 3-Iodophenyl-CO |
| 6.559 | 4-Iodophenyl-CO |
| 6.560 | 2-Chloro-4-Fluorophenyl-CO |
| 6.561 | 2-Chloro-5-Fluorophenyl-CO |
| 6.562 | 2-Chloro-6-Fluorophenyl-CO |
| 6.563 | 2-Chloro-4-Bromophenyl-CO |
| 6.564 | 2-Bromo-4-Chlorophenyl-CO |
| 6.565 | 2-Bromo-4-Fluorophenyl-CO |
| 6.566 | 3-Bromo-4-Chlorophenyl-CO |
| 6.567 | 3-Chloro-4-Fluorophenyl-CO |
| 6.568 | 3-Fluoro-4-Chlorophenyl-CO |
| 6.569 | 2-Cyanophenyl-CO |
| 6.570 | 3-Cyanophenyl-CO |
| 6.571 | 4-Cyanophenyl-CO |
| 6.572 | 2-Nitrophenyl-CO |
| 6.573 | 3-Nitrophenyl-CO |
| 6.574 | 4-Nitrophenyl-CO |
| 6.575 | 2-Methylphenyl-CO |
| 6.576 | 3-Methylphenyl-CO |
| 6.577 | 4-Methylphenyl-CO |
| 6.578 | 2,4-Dimethylphenyl-CO |
| 6.579 | 2,6-Dimethylphenyl-CO |
| 6.580 | 3,4-Dimethylphenyl-CO |
| 6.581 | 3,5-Dimethylphenyl-CO |
| 6.582 | 2,3,4-Trimethylphenyl-CO |
| 6.583 | 2,3,5-Trimethylphenyl-CO |
| 6.584 | 2,3,6-Trimethylphenyl-CO |
| 6.585 | 2,4,5-Trimethylphenyl-CO |
| 6.586 | 2,4,6-Trimethylphenyl-CO |
| 6.587 | 3,4,5-Trimethylphenyl-CO |
| 6.588 | 6-F-Pyridin-3-yl-CO |
| 6.589 | 6-Cl-Pyridin-3-yl-CO |
| 6.590 | 6-Br-Pyridin-3-yl-CO |
| 6.591 | 6-$CH_3$-Pyridin-3-yl-CO |
| 6.592 | 6-$CF_3$-Pyridin-3-yl-CO |
| 6.593 | 6-$CH_3$-Pyridin-3-yl-CO |
| 6.594 | 2-F-Pyridin-4-yl-CO |
| 6.595 | 2-Cl-Pyridin-4-yl-CO |
| 6.596 | 2-Br-Pyridin-4-yl-CO |
| 6.597 | 2-$CH_3$-Pyridin-4-yl-CO |

TABLE VI-continued

| | |
|---|---|
| 6.598 | 2-CF$_3$-Pyridin-4-yl-CO |
| 6.599 | 2-CH$_3$O-Pyridin-4-yl-CO |
| 6.600 | 3-F-Pyridin-4-yl-CO |
| 6.601 | 3-Cl-Pyridin-4-yl-CO |
| 6.602 | 3-Br-Pyridin-4-yl-CO |
| 6.603 | 3-CH$_3$-Pyridin-4-yl-CO |
| 6.604 | 3-CF$_3$-Pyridin-4-yl-CO |
| 6.605 | 3-CH$_3$O-Pyridin-4-yl-CO |
| 6.606 | 5-F-Pyridin-4-yl-CO |
| 6.607 | 5-Cl-Pyridin-4-yl-CO |
| 6.608 | 5-Br-Pyridin-4-yl-CO |
| 6.609 | 5-CH$_3$-Pyridin-4-yl-CO |
| 6.610 | 5-CF$_3$-Pyridin-4-yl-CO |
| 6.611 | 5-CH$_3$O-Pyridin-4-yl-CO |
| 6.612 | 6-F-Pyridin-4-yl-CO |
| 6.613 | 6-Cl-Pyridin-yl-CO |
| 6.614 | 6-Br-Pyridin-4-yl-CO |
| 6.615 | 6-CH$_3$-Pyridin-4-yl-CO |
| 6.616 | 6-CF$_3$-Pyridin-4-yl-CO |
| 6.617 | 6-CH$_3$O-Pyridin-4-yl-CO |
| 6.618 | 2-F-Pyridin-5-yl-CO |
| 6.619 | 2-Cl-Pyridin-5-yl-CO |
| 6.620 | 2-Br-Pyridin-5-yl-CO |
| 6.621 | 2-CH$_3$-Pyridin-5-yl-CO |
| 6.622 | 2-CF$_3$-Pyridin-5-yl-CO |
| 6.623 | 2-CH$_3$O-Pyridin-5-yl-CO |
| 6.624 | 4-F-Pyridin-5-yl-CO |
| 6.625 | 4-Cl-Pyridin-5-yl-CO |
| 6.626 | 4-Br-Pyridin-5-yl-CO |
| 6.627 | 4-CH$_3$-Pyridin-5-yl-CO |
| 6.628 | 4-CF$_3$-Pyridin-5-yl-CO |
| 6.629 | 4-CH$_3$O-Pyridin-5-yl-CO |
| 6.630 | 3-F-Pyridin-2-yl-CO |
| 6.631 | 3-Cl-Pyridin-2-yl-CO |
| 6.632 | 3-Br-Pyridin-2-yl-CO |
| 6.633 | 3-CH$_3$-Pyridin-2-yl-CO |
| 6.634 | 3-CF$_3$-Pyridin-2-yl-CO |
| 6.635 | 3-CH$_3$O-Pyridin-2-yl-CO |
| 6.636 | 4-F-Pyridin-2-yl-CO |
| 6.637 | 4-Br-Pyridin-2-yl-CO |
| 6.638 | 4-CF$_3$-Pyridin-2-yl-CO |
| 6.639 | 4-CH$_3$O-Pyridin-2-yl-CO |
| 6.640 | 5-F-Pyridin-2-yl-CO |
| 6.641 | 5-Cl-Pyridin-2-yl-CO |
| 6.642 | 5-Br-Pyridin-2-yl-CO |
| 6.643 | 5-CF$_3$-Pyridin-2-yl-CO |
| 6.644 | 5-CH$_3$-Pyridin-2-yl-CO |
| 6.645 | 5-CH$_3$O-Pyridin-2-yl-CO |
| 6.646 | 6-F-Pyridin-2-yl-CO |
| 6.647 | 6-Cl-Pyridin-2-yl-CO |
| 6.648 | 6-Br-Pyridin-2-yl-CO |
| 6.649 | 6-CH$_3$-Pyridin-2-yl-CO |
| 6.650 | 6-CF$_3$-Pyridin-2-yl-CO |
| 6.651 | 6-CH$_3$O-Pyridin-2-yl-CO |
| 6.652 | 2-F-Pyridin-3-yl-CO |
| 6.653 | 2-Cl-Pyridin-3-yl-CO |
| 6.654 | 2-Br-Pyridin-3-yl-CO |
| 6.655 | 2-CH$_3$-Pyidin-3-yl-CO |
| 6.656 | 2-CF$_3$-Pyridin-3-yl-CO |
| 6.657 | 2-CH$_3$O-Pyridin-3-yl-CO |
| 6.658 | 4-F-Pyridin-3-yl-CO |
| 6.659 | 4-Cl-Pyridin-3-yl-CO |
| 6.660 | 4-Br-Pyridin-3-yl-CO |
| 6.661 | 4-CH$_3$-Pyridin-3-yl-CO |
| 6.662 | 4-CF$_3$-Pyridin-3-yl-CO |
| 6.663 | 4-CH$_3$O-Pyridin-3-yl-CO |
| 6.664 | 5-F-Pyridin-3-yl-CO |
| 6.665 | 5-Cl-Pyridin-3-yl-CO |
| 6.666 | 5-Br-Pyridin-3-yl-CO |
| 6.667 | 5-CH$_3$-Pyridin-3-yl-CO |
| 6.668 | 5-CF$_3$-Pyridin-3-yl-CO |
| 6.669 | 5-CH$_3$O-Pyridin-3-yl-CO |

TABELLE VII

| Verb.-Nr. | R² | IR (cm⁻¹) |
|---|---|---|
| 7.1 |  | 1729, 1598, 1502, 1492, 1329, 1210, 1069, 1023, 960, 760 |

The novel compounds are suitable as fungicides.

The fungicidal compounds according to the invention, or agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

Usually, the plants are sprayed or dusted with the active ingredients or the seeds of the plants are treated with the active ingredients.

The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as ligninsulfite waste liquors and methylcellulose.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

Examples of formulations are given below.

I. A solution of 90 parts by weight of compound no. 1.35 and 10 parts by weight of N-methyl-α-pyrrolidone, which is suitable for application in the form of very fine drops.

II. A mixture of 20 parts by weight of compound no. 1.36, 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By finely dispersing the mixture in water, an aqueous dispersion is obtained.

III. An aqueous dispersion of 20 parts by weight of compound no. 1.115, 40 parts by weight of cyclohexanone, 30 parts by weight of isobutanol, 20 parts by weight of the adduct of 40 moles of ethylene oxide and 1 mole of castor oil.

IV. An aqueous dispersion of 20 parts by weight of compound no. 1.341, 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil.

V. A hammer-milled mixture of 80 parts by weight of compound no. 1.347, 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel. By finely dispersing the mixture in water, a spray liquor is obtained.

VI. An intimate mixture of 3 parts by weight of compound no. 1.457 and 97 parts by weight of particulate kaolin. The dust contains 3wt % of the active ingredient.

VII. An intimate mixture of 30 parts by weight of compound no. 1.35 92 parts by weight of powdered silica gel and 8 parts by weight of paraffin oil sprayed onto the surface of this silica gel. This formulation of the active ingredient exhibits good adherence.

VIII. A stable aqueous dispersion of 40 parts by weight of compound no. 1.36, 10 parts of the sodium salt of a phenolsulfonic acid-ureaformaldehyde condensate, 2 parts of silica gel and 48 parts of water, which dispersion can be further diluted.

IX. A stable oily dispersion of 20 parts by weight of compound no. 1.115, 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil.

The novel compounds are extremely effective on a broad spectrum of phytopathogenic fungi, in particular those from the class consisting of the Ascomycetes and Basidiomycetes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits, or in the seeds of these plants.

The compounds are applied by treating the fungi, or the seeds, plants, materials or the soil to be protected against fungus attack with a fungicidally effective amount of the active ingredients.

The active ingredients are applied before or after infection of the materials, plants or seed by the fungi.

The compounds I are particularly useful for controlling the following plant diseases:
*Erysiphe graminis* in cereals,
*Erysiphe cichoracearum* and *Sphaerotheca fuliginea* in cucurbits,
*Podosphaera leucotricha* in apples,
*Uncinula necator* in vines,
Puccinia species in cereals,
*Rhizoctonia solani* in cotton,
Ustilago species in cereals and sugar cane,
*Venturia inaequalis* (scab) in apples,
Helminthosporium species in cereals,
*Septoria nodorum* in wheat,
*Botrytis cinerea* (gray mold) in strawberries and grapes,
*Cercospora arachidicola* in groundnuts,
*Pseudocercosporella herpotrichoides* in wheat and barley,
*Pyricularia oryzae* in rice,
*Phytophthora infestans* in potatoes and tomatoes,
Fusarium and Verticillium species in various plants,
*Plasmopara viticola* in grapes,
Alternaria species in fruit and vegetables.

The novel compounds may also be used for protecting materials (timber), e.g., against Paecilomyces variotii.

Generally, the fungicidal agents contain from 0.1 to 95, and preferably from 0.5 to 90, % by weight of active ingredient.

Application rates vary, depending on the effect desired, and are from 0.02 to 3 kg of active ingredient per hectare.

When the active ingredients are used for treating seed, amounts of from 0.001 to 50, and preferably from 0.01 to 10, g per kg of seed are generally required.

When the agents according to the invention are used as fungicides, they may also be present together with, for example, herbicides, insecticides, growth regulators, other fungicides and fertilizers.

When mixed with other fungicides, the spectrum of fungicidal action is often increased.

The following list of fungicides with which the novel compounds may be combined is intended to illustrate possible combinations but not to impose any restrictions:
sulfur,
dithiocarbamates and their derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate,
armnonia complex of zinc N,N'-propylenebisdithiocarbamate,
zinc N,N'-propylenebisdithiocarbamate and
N,N'-polypropylenebis(thiocarbamyl) disulfide;
nitro derivatives, such as
dinitro(l-methylheptyl)-phenyl crotonate,
2-sec-butyl-4,6-dinitrophenyl 3,3-dimethylacrylate,
2-sec-butyl-4,6-dinitrophenyl isopropylcarbonate and
diisopropyl 5-nitroisophthalate;
heterocyclic substances, such as
2-heptadecylimidazol-2-yl acetate,
2,4-dichloro-6-(o-chloroanilino)-s-triazine,
O,O-diethyl phthalimidophosphonothioate,
5-amino-1-[-bis-(dimethylamino)-phosphinyll-3-phenyl-1,2,4-triazole
2,3-dicyano-1,4-dithioanthraquinone,
2-thio-1,3-dithio[4,5-b]quinoxaline,
methyl 1-(butylcarbamyl)-2-benzimidazolecarbamate,
2-methoxycarbonylaminobenzimidazole,
2-(fur-2-yl)-benzimidazole,
2-(thiazol-4-yl)benzimidazole,
N-(1,1,2,2-tetrachloroethylthio)-tetrahydrophthalimide,
N-trichloromethylthiotetrahydrophthalimide,
N-trichloromethylthiophthalimide,
N-dichlorofluoromethylthio-N',N'-dimethyl-N-phenyl-sulfuric acid diamide,
5-ethoxy-3-trichloromethyl-1,2,3-thiadiazole,
2-thiocyanatomethylthiobenzothiazole,
1,4-dichloro-2,5-dimethoxybenzene,
2-methylfuran-3-carboxanilide,
2,5-dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-diethylfuran-3-carboxamide,
2-methylbenzanilide,
2-iodobenzanilide,
N-formyl-N-morpholine-2,2,2-trichloroethylacetal,
piperazine-1,4-diylbis-(l-(2,2,2-trichloroethyl)-formamide),
1-(3,4-dichloroanilino)-1-formylamino-2,2,2-trichloroethane,
2,6-dimethyl-N-tridecylmorpholine and its salts,
2,6-dimethyl-N-cyclododecylmorpholine and its salts,
N-[3-(p-tert.-butylphenyl)-2-methylpropyl]-cis-2,6-dimethylmorpholine,
N-[3-(p-tert.-butylphenyl)-2-methylpropyll-piperidine,
1-[2-(2,4-dichlorophenyl)-4-ethyl-1,3-dioxolan-2-ylethyl]-1H-1,2,4--triazole, -[2-(2,4-dichlorophenyl)-4-n-propyl-1,3-dioxolan-2-ylethyl]-1H-1,2,4-triazole,
N-(n-propyl)-N-(2,4,6-trichlorophenoxyethyl)-N'-imidazolyl-urea,
1-(4-chlorophenoxy)-3,3-dimethyl-1-(1H-1,2,4-triazol-1-yl)-butan-2-one,
1-(4-chlorophenoxy)-3,3-dimethyl-1-(1H-1,2,4-triazol-1-yl)-butan-2-ol,
α-(2-chlorophenyl)-a-(4-chlorophenyl)-5-pyrimidinemethanol,
5-butyl-(2-dimethylamino-4-hydroxy-6-methylpyrimidine,
bis-(p-chlorophenyl)-3-pyridinemethanol,
1,2-bis-(3-ethoxycarbonyl-2-thioureido)-benzene,
1,2-bis-(3-methoxycarbonyl-2-thioureido)-benzene,
and various fungicides, such as
dodecylguanidine acetate,
3-[3-(3,5-dimethyl-2-oxycyclohexyl)-2-hydroxyethyll-glutaramide,
hexachlorobenzene
DL-methyl-N-(2,6-dimethylphenyl)-N-fur-2-yl alanate,
methyl DL-N-(2,6-dimethylphenyl)-N-(2'-methoxyacetyl)-alanate,
N-(2,6-dimethylphenyl)-N-chloroacetyl-DL-2-aminobutyrolactone,
methyl DL-N-(2,6-dimethylphenyl)-N-(phenylacetyl)-alanate,
5-methyl-5-vinyl-3-(3,5-dichlorophenyl)-2,4-dioxo-1,3-oxazolidine,
3-[3,5-dichlorophenyll-5-methyl-5-methoxymethyl-1,3-oxazolidine-2,4-dione,
3-(3,5-dichlorophenyl)-1-isopropylcarbamylhydantoin,
N-(3,5-dichlorophenyl)-1,2-dimethylcyclopropane-1,2-dicarboximide,
2-cyano-[N-(ethylaminocarbonyl)-2-methoximino]-acetamide
1-[2-(2,4-dichlorophenyl)-pentyll-1H-1,2,4-triazole,
2,4-difluoro-a-(1H-1,2,4-triazol-1-ylmethyl)-benzhydryl alcohol,
N-(3-chloro-2,6-dinitro-4-trifluoromethylphenyl)-5-trifluoromethyl-3-chloro-2-aminopyridine, and
1-((bis-(4-fluorophenyl)-methylsilyl)-methyl)-1H-1,2,4-triazole.

USE EXAMPLES

For comparison purposes, compound no. 4 from EP 370,629 (A) and compound no. 5 from EP 370,629 (B) were used.

USE EXAMPLE 1

Action on wheat brown rust

Leaves of pot-grown wheat seedlings of the "Frühgold" variety were dusted with spores of brown rust (Puccinia recondite). The pots were then placed for 24 hours at 20° to 22° C. in a high-humidity (90–95%) chamber. During this period the spores germinated and the germ tubes penetrated the leaf tissue. The infected plants were then sprayed to runoff with aqueous liquors containing (dry basis) 80% of active ingredient and 20% of emulsifier. After the sprayed-on layer had dried, the plants were set up in the greenhouse at 20° to 22° C. and a relative humidity of 65 to 70 l/,. The extent of rust fungus spread on the leaves was assessed after 8 days.

The results obtained show that active ingredient 1.35, applied as a 0.025wt % spray liquor, has a better fungicidal action (80%) than prior art comparative agent A (30%).

USE EXAMPLE 2.

Action on wheat mildew

Leaves of pot-grown wheat seedlings of the "Frühgold" variety were sprayed with aqueous liquors containing (dry basis) 80% of active ingredient and 20% of emulsifier, and dusted, 24 hours after the sprayed-on layer had dried, with spores of wheat mildew (Erysiphe graminis var. tritici). The plants were then set up in the greenhouse at from 20° to 22° C. and a relative humidity of from 75 to 80%. The extent of mildew spread was assessed after 7 days.

The results obtained show that active ingredient 1.36, applied as a 0.0015wt % spray liquor, has a better fungicidal action (90%) than prior art comparative agent B (55%).

USE EXAMPLE 3

Action on Plasmopara viticola

Leaves of potted vines of the Müller-Thurgau variety were sprayed with aqueous liquors containing (dry basis) 80% of active ingredient and 20% of emulsifier. To assess the duration of action, the plants were set up, after the sprayed-on layer had dried, for 8 days in the greenhouse. Then the leaves were infected with a zoospore suspension of Plasmopara viticola. The plants were first placed for 48 hours in a water vapor-saturated chamber at 24° C. and then in a greenhouse for 5 days at from 20° to 30° C. To accelerate and intensify the sporangiophore discharge, the plants were then again placed in the moist chamber for 16 hours. The extent of fungus attack was then assessed on the undersides of the leaves.

The results obtained show that active ingredients 1.35, 1.36, 1.115, 1.341, 1.347 and 1.457, applied as 0.025wt% spray liquors, have a very good fungicidal action (95%).

We claim:

1. A compound of the formula I

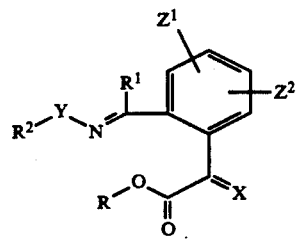

where
R is hydrogen or $C_1-C_6$-alkyl;
$R^1$ is hydrogen, $C_1-C_4$-alkyl, $C_1-C_4$-haloalkyl or unsubstituted or substituted aryl;
$Z^1$ and $Z^2$ are identical or different and each is hydrogen, halogen, $C_1-C_4$-alkoxy, $C_2-C_4$-alkenyloxy, cyano, nitro, $C_1-C_4$-haloalkyl, $C_2-C_4$-haloalkenyloxy, $C_2-C_4$-alkenyl, $C_1-C_4$-haloalkoxy, $C_1-C_6$alkyl or $C_2-C_4$-alkynyl;

Y is oxygen (—O—), nitrogen, (—NH—) or $C_1$–$C_6$-alkyl ($R^3$)-substituted nitrogen (—N($R^3$)—), where $R^3$ is hydrogen or $C_1$–$C_6$ alkyl;

$R^2$ is hydrogen, unsubstituted or substituted alkyl, unsubstituted or substituted cycloalkyl, unsubstituted or substituted alkenyl, unsubstituted or substituted aryl, unsubstituted or substituted alkynyl, unsubstituted or substituted cycloalkenyl, unsubstituted or substituted arylalkyl, unsubstituted or substituted aryloxyalkyl, unsubstituted or substituted hetaryl, unsubstituted or substituted hetarylalkyl, unsubstituted or substituted hetaryloxyalkyl, unsubstituted or substituted acyl, unsubstituted or substituted arylalkenyl, unsubstituted or substituted hetarylalkenyl, unsubstituted or substituted heterocyclyl, unsubstituted or substituted heterocyclyloxy, unsubstituted or substituted arylcarbonyl, unsubstituted or substituted hetarylcarbonyl or $C_1$–$C_4$-alkoxycarbonyl-$C_1$–$C_4$-alkyl, where Y and $R^2$ may form a ring which may be substituted if Y is —NH— or —N$R^3$—;

X is $CH_2$, CH—$C_1$–$C_4$-alkyl, CH—$C_1$–$C_4$-alkoxy, CH—$C_1$–$C_4$-alkylthio, N—$C_1$–$C_4$-alkoxy or NOH, wherein in the above substituted groups the substituent is selected from the group consisting of halogen, $C_1$–$C_6$-alkyl, $C_1$–$C_6$- alkyloxy, $C_1$–$C_6$- alkylthio, $C_1$–$C_4$-haloalkyl, $C_1$–$C_4$-haloalkoxy, $C_2$–$C_6$-alkenyloxy, cyano, cyanato, thiocyanato, nitro, amino, hydroxyl, carboxyl, $C_1$–$C_6$-alkylamino, di-$C_1$–$C_6$-alkylamino, phenyl, phenoxy, phenylthio, phenylamino, $C_1$–$C_6$-alkoxyiminoalkyl, $C_1$–$C_4$-alkyliminoalkyl and $C_3$–$C_6$- cycloalkyl.

2. A compound of the formula I as claimed in claim 1, where X is $CHCH_3$, $CHC_3H_5$, $CHOCH_3$ or $CHSCH_3$.

3. A compound of the formula I as claimed in claim 1, where X is NOH or $NOCH_3$.

4. A fungicidal composition containing an inert carrier and a fungicidal amount of a compound of the formula I

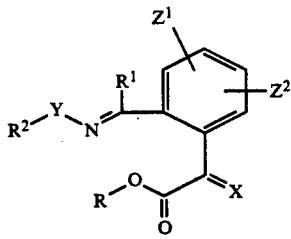

where

R is hydrogen or $C_1$–$C_6$-alkyl;

$R^1$ is hydrogen, $C_1$–$C_4$-alkyl, $C_1$–$C_4$-haloalkyl or unsubstituted or substituted aryl;

$Z^1$ and $Z^2$ are identical or different and each is hydrogen, halogen, $C_1$–$C_4$-alkoxy, $C_2$–$C_4$-alkenyloxy, cyano, nitro, $C_1$–$C_4$-haloalkyl, $C_2$–$C_4$-haloalkenyloxy, $C_2$–$C_4$-alkenyl, $C_1$–$C_4$-haloalkoxy, $C_1$–$C_6$-alkyl or $C_2$–$C_4$-alkynyl;

Y is oxygen (—O—), nitrogen, (—NH—) or $C_1$–$C_6$-alkyl ($R^3$)-substituted nitrogen (—N($R^3$)—) wherein $R^3$ is hydrogen or $C_1$–$C_6$-alkyl;

$R^2$ is hydrogen, unsubstituted or substituted alkyl, unsubstituted or substituted cycloalkyl, unsubstituted or substituted alkenyl, unsubstituted or substituted aryl, unsubstituted or substituted alkynyl, unsubstituted or substituted cycloalkenyl, unsubstituted or substituted arylalkyl, unsubstituted or substituted aryloxyalkyl, unsubstituted or substituted hetaryl, unsubstituted or substituted hetarylalkyl, unsubstituted or substituted hetaryloxyalkyl, unsubstituted or substituted acyl, unsubstituted or substituted arylalkenyl, unsubstituted or substituted hetarylalkenyl, unsubstituted or substituted heterocyclyl, unsubstituted or substituted heterocyclyloxy, unsubstituted or substituted arylcarbonyl, unsubstituted or substituted hetarylcarbonyl or $C_1$–$C_4$-alkoxycarbonyl-$C_1$–$C_4$-alkyl, where Y and $R^2$ may form a ring which may be substituted if Y is —NH— or —N$R^3$—;

X is $CH_2$, CH—$C_1$–$C_4$-alkyl, CH—$C_1$–$C_4$-alkoxy, CH—$C_1$–$C_4$-alkylthio, N—$C_1$–$C_4$-alkoxy or NOH, wherein in the above substituted groups the substituent is selected from the group consisting of halogen, $C_1$–$C_6$-alkyl, $C_1$–$C_6$- alkyloxy, $C_1$–$C_6$- alkylthio, $C_1$–$C_4$-haloalkyl, $C_1$–$C_4$-haloalkoxy, $C_2$–$C_6$-alkenyloxy, cyano, cyanato, thiocyanato, nitro, amino, hydroxyl, carboxyl, $C_1$–$C_6$-alkylamino, di-$C_1$–$C_6$-alkylamino, phenyl, phenoxy, phenylthio, phenylamino, $C_1$–$C_6$-alkoxyiminoalkyl, $C_1$–$C_4$-alkyliminoalkyl and $C_3$–$C_6$- cycloalkyl.

5. A method for controlling fungi, which comprises treating the fungi or the materials, plants, seeds or soil threatened by fungal attack with a fungicidal amount of a compound of the formula I

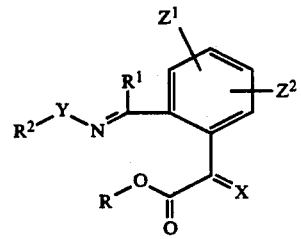

where

R is hydrogen or $C_1$–$C_6$-alkyl;

$R^1$ is hydrogen, $C_1$–$C_4$-alkyl, $C_1$–$C_4$-haloalkyl or unsubstituted or substituted aryl;

$Z^1$ and $Z^2$ are identical or different and each is hydrogen, halogen, $C_1$–$C_4$-alkoxy, $C_2$–$C_4$-alkenyloxy, cyano, nitro, $C_1$–$C_4$-haloalkyl, $C_2$–$C_4$-haloalkenyloxy, $C_2$–$C_4$-alkenyl, $C_1$–$C_4$-haloalkoxy, $C_1$–$C_6$-alkyl or $C_2$–$C_4$-alkynyl;

Y is oxygen (—O—), nitrogen, (—NH—) or $C_1$–$C_6$-alkyl ($R^3$)-substituted nitrogen (—N($R^3$)—) wherein $R^3$ is hydrogen or $C_1$–$C_6$-alkyl;

$R^2$ is hydrogen, unsubstituted or substituted alkyl, unsubstituted or substituted cycloalkyl, unsubstituted or substituted alkenyl, unsubstituted or substituted aryl, unsubstituted or substituted alkynyl, unsubstituted or substituted cycloalkenyl, unsubstituted or substituted arylalkyl, unsubstituted or substituted aryloxyalkyl, unsubstituted or substituted hetaryl, unsubstituted or substituted hetarylalkyl, unsubstituted or substituted hetaryloxyalkyl, unsubstituted or substituted acyl, unsubstituted or substituted arylalkenyl, unsubstituted or substituted hetarylalkenyl, unsubstituted or substituted heterocyclyl, unsubstituted or substituted heterocyclyloxy, unsubstituted or substituted arylcarbonyl, unsubstituted or substituted hetarylcarbonyl or $C_1$–$C_4$-alkoxycarbonyl-$C_1$–$C_4$-alkyl, where Y and $R^2$ may form a ring which may be substituted if Y is —NH— or —$NR^3$—;

X is $CH_2$, CH—$C_1$–$C_4$-alkyl, CH—$C_1$–$C_4$-alkoxy, CH—$C_1$–$C_4$-alkylthio, N—$C_1$–$C_4$-alkoxy or NOH, wherein in the above substituted groups the substituent is selected from the group consisting of halogen, $C_1$–$C_6$-alkyl, $C_1$–$C_6$-alkyloxy, $C_1$–$C_6$-alkylthio, $C_1$–$C_4$-haloalkyl, $C_1$–$C_4$-haloalkoxy, $C_2$–$C_6$-alkenyloxy, cyano, cyanato, thiocyanato, nitro, amino, hydroxyl, carboxyl, $C_1$–$C_6$-alkylamino, di-$C_1$–$C_6$-alkylamino, phenyl, phenoxy, phenylthio, phenylamino, $C_1$–$C_6$-alkoxyiminoalkyl, $C_1$–$C_4$-alkyliminoalkyl and $C_3$–$C_6$-cycloalkyl.

6. A compound of the formula I as claimed in claim 1, wherein $R^1$ is hydrogen, $R^2$ is 2-methylbenzyl, Y is O, R is methyl, $Z^1$ and $Z^2$ are each hydrogen and X is $NOCH_3$.

7. A compound of the formula I as claimed in claim 1, wherein $R^1$, $Z^1$ and $Z^2$ are each hydrogen, $R^2$ is 3-methylbenzyl, Y is O, R is methyl and X is $NOCH_3$.

* * * * *

UNITED STATES PATENT AND TRADEMARK OFFICE
CERTIFICATE OF CORRECTION

PATENT NO. : 5,254,717
DATED : October 19, 1993
INVENTOR(S) : Wassilios Grammenos et al.

It is certified that error appears in the above-indentified patent and that said Letters Patent is hereby corrected as shown below:

On the title page, Item [30],

The Foreign Application Priority Data, should read:

--Feb. 20, 1991  [DE]  Fed. Rep. of Germany........4105160--

Signed and Sealed this

Twenty-ninth Day of March, 1994

Attest:

BRUCE LEHMAN

*Attesting Officer*  *Commissioner of Patents and Trademarks*